United States Patent
Shen et al.

(10) Patent No.: US 11,096,383 B2
(45) Date of Patent: *Aug. 24, 2021

(54) METHOD OF USING A GENETICALLY MODIFIED MOUSE THAT EXPRESSES A HUMANIZED CTLA-4 GENE

(71) Applicant: Biocytogen Pharmaceuticals (Beijing) Co., Ltd., Beijing (CN)

(72) Inventors: Yuelei Shen, Beijing (CN); Yanan Guo, Beijing (CN); Yang Bai, Beijing (CN); Jiawei Yao, Beijing (CN); Chengzhang Shang, Beijing (CN); Rui Huang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/329,275

(22) PCT Filed: Aug. 30, 2017

(86) PCT No.: PCT/CN2017/099577
§ 371 (c)(1),
(2) Date: Feb. 28, 2019

(87) PCT Pub. No.: WO2018/041121
PCT Pub. Date: Mar. 8, 2018

(65) Prior Publication Data
US 2019/0373864 A1    Dec. 12, 2019

(30) Foreign Application Priority Data

Aug. 31, 2016 (CN) .......................... 201610784999.2
Aug. 29, 2017 (CN) ......................... 201710757917.X

(51) Int. Cl.
*A01K 67/027* (2006.01)
*A61K 49/00* (2006.01)
*C07K 14/705* (2006.01)
*C07K 16/28* (2006.01)
*C12N 15/85* (2006.01)

(52) U.S. Cl.
CPC ...... *A01K 67/0278* (2013.01); *A01K 67/0276* (2013.01); *A61K 49/0008* (2013.01); *C07K 14/70521* (2013.01); *C07K 16/2818* (2013.01); *C12N 15/8509* (2013.01); *A01K 2217/072* (2013.01); *A01K 2217/075* (2013.01); *A01K 2227/105* (2013.01); *A01K 2267/0331* (2013.01); *C07K 2317/21* (2013.01); *C07K 2317/76* (2013.01)

(58) Field of Classification Search
CPC ............. A01K 67/028; A01K 2207/15; A01K 2217/072; A01K 2227/105
USPC .......................................... 800/3, 8, 18, 21
See application file for complete search history.

(56) References Cited

U.S. PATENT DOCUMENTS

| | | | |
|---|---|---|---|
| 4,683,195 A | 7/1987 | Mullis et al. | |
| 5,714,667 A | 2/1998 | Waterhouse et al. | |
| 6,875,904 B2 * | 4/2005 | Liu .................... | A01K 67/0271 800/13 |
| 7,161,058 B2 * | 1/2007 | Liu .................... | A01K 67/0271 800/13 |
| 7,504,544 B2 | 3/2009 | Puentener et al. | |
| 7,504,554 B2 * | 3/2009 | Liu .................... | A01K 67/0271 800/13 |
| 10,314,297 B2 | 6/2019 | Shen | |
| 2002/0115209 A1 | 8/2002 | Liu et al. | |
| 2006/0179501 A1 | 8/2006 | Chan | |
| 2007/0111962 A1 | 5/2007 | Mourich | |
| 2015/0106961 A1 | 4/2015 | Rojas et al. | |
| 2016/0157470 A1 | 6/2016 | Cagan et al. | |

FOREIGN PATENT DOCUMENTS

| | | |
|---|---|---|
| CN | 101998965 | 3/2011 |
| CN | 104561095 | 4/2015 |
| CN | 104904661 A | 9/2015 |
| CN | 107815465 A | 3/2018 |
| CN | 107815466 A | 3/2018 |
| CN | 107815467 A | 3/2018 |
| WO | WO 2006/096491 | 9/2006 |
| WO | wo 2012/120125 | 9/2012 |
| WO | WO 2016/196237 | 12/2016 |
| WO | WO 2017/087780 | 5/2017 |
| WO | WO 2018/001241 | 1/2018 |

OTHER PUBLICATIONS

GenBank, "*Homo sapiens* cytotoxic T-lymphocyte-associated protein 4, mRNA (cDNA clone MDC: 97034 Image: 7262243), complete cds" GenBank: BC069566.1, Apr. 29, 2004, 3 pages.
GenBank, "*Mus musculus* cytotoxic T-lymphocyte-associated protein 4, mRNA (cDNA clone MGC: 60618 Image: 30072821), complete cds)," GenBank: BC062683.1, May 16, 2003, 4 pages.
Extended European Search Report in EP Appln. No. 17845423, dated Jan. 21, 2020, 8 pages.
Garanto et al., "Unexpected CEP290 mRNA splicing in a humanized knock-in mouse model for Leber congenital amaurosis," PLoS, 2013, 8(11):e79369.
Tong et al., "Production of p53 gene knockout rats by homologous recombination in embryonic stem cells," Nature Letters, 2010, 467:211-213.
Auerbach et al., "Establishment and Chimera Analysis of 129/SvEv- and C57BL/6-Derived Mouse Embryonic Stem Cell Lines," BioTechniques, 2000. 29:1024-1032.
Festing et al. "Revised nomenclature for strain 129 mice," Mammalian Genome, 1999, 10:836.
GenBank "cytotoxic T-Iymphocyte proetin 4 precursor [Papio ailubis]," GenBank: NP_001106104.1, Aug. 26, 2016.

(Continued)

*Primary Examiner* — Michael C Wilson
(74) *Attorney, Agent, or Firm* — Fish & Richardson P.C.

(57) ABSTRACT

The present disclosure relates to the genetically modified non-human animals that express a human or chimeric CTLA-4, and methods of use thereof.

13 Claims, 25 Drawing Sheets

Specification includes a Sequence Listing.

(56) References Cited

OTHER PUBLICATIONS

GenBank, "Mus musculus cytotoxic T-lymphocyte-associated protein 4 (Ctla4), transcript variant 1, mRNA," GenBank: NM_009843. 4, Feb. 15, 2015, 4 pages.
GenBank, "Synthetic construct clone shicr90-1 cytotoxic T-lymphocyte-associated protein 4 gene, complete cds," GenBank: KP271012.1, Jan. 11, 2015, 2 pages.
Ito, M. et al, "NOD/SCID/ycnull mouse: an excellent recipient mouse model for engraftment of human cells," Blood, 2002, 100(9):3175-3182.
Jiang et al., "The production of skin specifically expression human CTLA-4 Ig transgenic bama miniature pig and its function in xenotransplantation," Chinese Doctoral Dissertations Full-Text Database Agriculture Sciences and Technology, 2012, 12:1-155 (with English abstract).
Lute et al., "Human CTLA4 knock-in mice unravel the quantitative link between tumor immunity and autoimmunity induced by anti-CTLA04 antibodies," Blood. 106(9):3127-3133.
Masteller et al., "Structural analysis of CTLA-4 function," The Journal of Immunology, 2000, 164:5319-5327.
PCT International Preliminary Report on Patentability in International Appln. No. PCT/CN2017/099577, dated Mar. 5, 2019, 6 pages.
PCT International Search Report and Written Opinion in International Appln. No. PCT/CN2017/099577, dated Nov. 27, 2017, 12 pages.
Yin et al., "Delivery technologies for genome editing," Nature Reviews Drug Discovery, 2017, 16(6):387-399.
GenBank Accession No. AF486806, "Homo sapiens CTLA4 mRNA, partial cds," Mar. 27, 2002, 1 page.
GenBank Accession No. BC052683.1, "Mus musculus cytotoxic T-lymphocyte-associated protein 4, mRNA (cDNA clone MGC:60618 IMAGE:30072821), complete cds," May 19, 2003, 2 pages.
Harms et al., "Mouse Genome Editing Using the CRISPR/Cas System," Curr Protoc Hum Genetics, Oct. 2014, 83(1):15.7.1-15.7.27.
Schilit et al., "Pronuclear Injection-Based Targeted Transgenesis," Curr Protoc Hum Genet., Oct. 2016,91(1):15,10.1-15.10.28.

\* cited by examiner

| Score | Expect | Method | Identities | Positives | Gaps |
|---|---|---|---|---|---|
| 349 bits(896) | 1e-128 | Compositional matrix adjust. | 167/223(75%) | 189/223(84%) | 0/223(0%) |

```
Mouse    1  MACLGLRRYKAQLQLPSRTWPFVALLTLLFIPVFSEAIQVTQPSVVLASSHGVASFPCEY   60
            MACLG +R+KAQL L +RTWP   L  LLFIPVF +A+ V QP+VVLASS G+ASF CEY
Human    1  MACLGFQRHKAQLNLATRTWPCTLLFFLLFIPVFCKAMHVAQPAVVLASSRGIASFVCEY   60

Mouse   61  SPSHNTDEVRVTVLRQTNDQMTEVCATTFTEKNTVGFLDYPFCSGTFNESRVNLTIQGLR  120
            +    EVRVTVLRQ + Q+TEVCA T+    N + FLD   C+GT + ++VNLTIQGLR
Human   61  ASPGKATEVRVTVLRQADSQVTEVCAATYMGNELTFLDDSTCTGTSSGNQVNLTIQGLR  120

Mouse  121  AVDTGLYLCKVELMYPPPYFVGMGNGTQIYVIDPEPCPDSDFLLWIIVAVSLGLFFYSFL  180
            A+DTGLY +CKVELMYPPPY ++G+GNGTQIYVIDPEPCPDSDFLLWIL AVS GLFFYSFL
Human  121  AMDTGLYICKVELMYPPPYYLGIGNGTQIYVIDPEPCPDSDFLLWILAAVSSGLFFYSFL  180

Mouse  181  VTAVSLSKMLKKRSPLTTGVYVKMPPTEPECEKQFQPYFIPIN  223
            +TAVSLSKMLKKRSPLTTGVYVKMPPTEPECEKQFQPYFIPIN
Human  181  LTAVSLSKMLKKRSPLTTGVYVKMPPTEPECEKQFQPYFIPIN  223
```

FIG. 25

SEQUENCE LISTING

```
<160> NUMBER OF SEQ ID NOS: 71

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1
ggtcacctgt atggctgaca tgg                                              23

<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2
tgaaggttgg gtcacctgta tgg                                              23

<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3
acaggtgacc caaccttcag tgg                                              23
```

```
<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4
gacccaacct tcagtggtgt tgg                                              23

<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5
agccaacacc actgaaggtt ggg                                              23

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
ctgctagcca acaccactga agg                                              23

<210> SEQ ID NO 7
<211> LENGTH: 23
<212> TYPE: DNA
<213> ORGANISM: Artificial
<220> FEATURE:
<223> OTHER INFORMATION: sgRNA target sequence

<400> SEQUENCE: 7
gtggtgttgg ctagcagcca tgg                                              23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
atggaaagct ggcgacacca tgg                                              23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
tgtgatggtg aatattcaca tgg                                              23

<210> SEQ ID NO 10
<211> LENGTH: 23
<212> TYPE: DNA
<213> ORGANISM: Artificial
<220> FEATURE:
<223> OTHER INFORMATION: sgRNA target sequence
```

```
<400> SEQUENCE: 10
accatcacac aaacactgatg agg                                          23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
acctcatcag tgttgtgtga tgg                                           23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
acacaacact gatgaggtcc ggg                                           23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
aggtccgggt gactgtgctg cgg                                           23

<210> SEQ ID NO 14
<211> LENGTH: 23
<212> TYPE: DNA
<213> ORGANISM: Artificial
<220> FEATURE:
<223> OTHER INFORMATION: sgRNA target sequence

<400> SEQUENCE: 14
tctgccgcag cacagtcacc cgg                                           23

<210> SEQ ID NO 15
<211> LENGTH: 23
<212> TYPE: DNA
<213> ORGANISM: Artificial
<220> FEATURE:
<223> OTHER INFORMATION: sgRNA target sequence

<400> SEQUENCE: 15
tggcacagac ctcagtcatt tgg                                           23

<210> SEQ ID NO 16
<211> LENGTH: 23
<212> TYPE: DNA
<213> ORGANISM: Artificial
<220> FEATURE:
<223> OTHER INFORMATION: sgRNA target sequence

<400> SEQUENCE: 16
actttgtggg catgggcaac ggg                                           23

<210> SEQ ID NO 17
```

```
<211> LENGTH: 23
<212> TYPE: DNA
<213> ORGANISM: Artificial
<220> FEATURE:
<223> OTHER INFORMATION: sgRNA target sequence

<400> SEQUENCE: 17
ttgcccatgc ccacaaagta tgg                                            23

<210> SEQ ID NO 18
<211> LENGTH: 23
<212> TYPE: DNA
<213> ORGANISM: Artificial
<220> FEATURE:
<223> OTHER INFORMATION: sgRNA target sequence

<400> SEQUENCE: 18
ccgccatact ttgtgggcat ggg                                            23

<210> SEQ ID NO 19
<211> LENGTH: 23
<212> TYPE: DNA
<213> ORGANISM: Artificial
<220> FEATURE:
<223> OTHER INFORMATION: sgRNA target sequence

<400> SEQUENCE: 19
atgcccacaa agtatggcgg tgg                                            23

<210> SEQ ID NO 20
<211> LENGTH: 23
<212> TYPE: DNA
<213> ORGANISM: Artificial
<220> FEATURE:
<223> OTHER INFORMATION: sgRNA target sequence

<400> SEQUENCE: 20
tacccaccgc catactttgt ggg                                            23

<210> SEQ ID NO 21
<211> LENGTH: 23
<212> TYPE: DNA
<213> ORGANISM: Artificial
<220> FEATURE:
<223> OTHER INFORMATION: sgRNA target sequence

<400> SEQUENCE: 21
ggactgagag ctgttgacac ggg                                            23

<210> SEQ ID NO 22
<211> LENGTH: 23
<212> TYPE: DNA
<213> ORGANISM: Artificial
<220> FEATURE:
<223> OTHER INFORMATION: sgRNA target sequence

<400> SEQUENCE: 22
tgtcaacagc tctcagtcct tgg                                            23

<210> SEQ ID NO 23
<211> LENGTH: 23
<212> TYPE: DNA
<213> ORGANISM: Artificial
<220> FEATURE:
<223> OTHER INFORMATION: sgRNA target sequence

<400> SEQUENCE: 23
```
gttcactctg ctttcattaa agg                                              23

<210> SEQ ID NO 24
<211> LENGTH: 23
<212> TYPE: DNA
<213> ORGANISM: Artificial
<220> FEATURE:
<223> OTHER INFORMATION: sgRNA target sequence

<400> SEQUENCE: 24
attaaaggta ccactgcaga agg                                              23

<210> SEQ ID NO 25
<211> LENGTH: 16
<212> TYPE: DNA
<213> ORGANISM: Artificial
<220> FEATURE:
<223> OTHER INFORMATION: sgRNA sequence

<400> SEQUENCE: 25
tgttggctag cagcca                                                      16

<210> SEQ ID NO 26
<211> LENGTH: 20
<212> TYPE: DNA
<213> ORGANISM: Artificial
<220> FEATURE:
<223> OTHER INFORMATION: sgRNA sequence

<400> SEQUENCE: 26
taggtgttgg ctagcagcca                                                  20

<210> SEQ ID NO 27
<211> LENGTH: 16
<212> TYPE: DNA
<213> ORGANISM: Artificial
<220> FEATURE:
<223> OTHER INFORMATION: sgRNA sequence

<400> SEQUENCE: 27
tggctgctag ccaaca                                                      16

<210> SEQ ID NO 28
<211> LENGTH: 20
<212> TYPE: DNA
<213> ORGANISM: Artificial
<220> FEATURE:
<223> OTHER INFORMATION: sgRNA sequence

<400> SEQUENCE: 28
aaactggctg ctagccaaca                                                  20

<210> SEQ ID NO 29
<211> LENGTH: 17
<212> TYPE: DNA
<213> ORGANISM: Artificial
<220> FEATURE:
<223> OTHER INFORMATION: sgRNA sequence

<400> SEQUENCE: 29
ccatactttg tgggcat                                                     17

<210> SEQ ID NO 30
<211> LENGTH: 21
<212> TYPE: DNA

```
<213> ORGANISM: Artificial
<220> FEATURE:
<223> OTHER INFORMATION: sgRNA sequence

<400> SEQUENCE: 30
taggccatac tttgtgggca t                                              21

<210> SEQ ID NO 31
<211> LENGTH: 17
<212> TYPE: DNA
<213> ORGANISM: Artificial
<220> FEATURE:
<223> OTHER INFORMATION: sgRNA sequence

<400> SEQUENCE: 31
atgcccacaa agtatgg                                                   17

<210> SEQ ID NO 32
<211> LENGTH: 21
<212> TYPE: DNA
<213> ORGANISM: Artificial
<220> FEATURE:
<223> OTHER INFORMATION: sgRNA sequence

<400> SEQUENCE: 32
aaacatgccc acaaagtatg g                                              21

<210> SEQ ID NO 33
<211> LENGTH: 132
<212> TYPE: DNA
<213> ORGANISM: Artificial
<220> FEATURE:
<223> OTHER INFORMATION: Synthesized sequence

<400> SEQUENCE: 33
gaattctaat acgactcact ataggggtc ttcgagaaga cctgttttag agctagaaat      60
agcaagttaa aataaggcta gtccgttatc aacttgaaaa agtggcaccg agtcggtgct    120
tttaaaggat cc                                                       132

<210> SEQ ID NO 34
<211> LENGTH: 1933
<212> TYPE: DNA
<213> ORGANISM: Mus musculus

<400> SEQUENCE: 34
ctacacatat gtagcacgta ccttggatca aagctgtcta tataaagtcc ccgagtctgt     60
gtgggttcaa acacatctca aggcttctgg atcctgttgg gttttactct gctccctgag    120
gacctcagca catttgcccc ccagccatgg cttgtcttgg actccggagg tacaaagctc    180
aactgcagct gccttctagg acttggcctt ttgtagccct gctcactctt cttttcatcc    240
cagtcttctc tgaagccata caggtgaccc aaccttcagt ggtgttggct agcagccatg    300
gtgtcgccag ctttccatgt gaatattcac catcacacaa cactgatgag gtccgggtga    360
ctgtgctgcg gcagacaaat gaccaaatga ctgaggtctg tgccacgaca ttcacagaga    420
agaatacagt gggcttccta gattacccct tctgcagtgg tacctttaat gaaagcagag    480
tgaacctcac catccaagga ctgagagctg ttgacacggg actgtacctc tgcaaggtgg    540
aactcatgta cccaccgcca tactttgtgg gcatgggcaa cgggacgcag atttatgtca    600
ttgatccaga accatgcccg gattctgact tcctcctttg gatccttgtc gcagttagct    660
tggggttgtt ttttacagt ttcctggtca ctgctgtttc tttgagcaag atgctaaaga    720
```

-continued

```
aaagaagtcc tcttacaaca ggggtctatg tgaaaatgcc cccaacagag ccagaatgtg    780
aaaagcaatt tcagccttat tttattccca tcaactgaaa ggccgtttat gaagaagaag    840
gagcatactt cagtctctaa aagctgaggc aatttcaact ttccttttct ctccagctat    900
ttttacctgt ttgtatattt taaggagagt atgcctctct ttaatagaaa gctggatgca    960
aaattccaat taagcatact acaatttaaa gctaaggagc atgaacagag agctgggata   1020
tttctgttgt gtcagaacca ttttactaaa agcatcactt ggaagcagca taaggatata   1080
gcattatggt gtggggtcaa gggaacatta ggaatggca cagcccaaag aaaggaaggg    1140
ggtgaaggaa gagattatat tgtacacatc ttgtatttac ctgagagatg tttatgactt   1200
aaataatttt taaatttttc atgctgttat tttcttaac aatgtataat tacacgaagg    1260
tttaaacatt tattcacaga gctatgtgac atagccagtg gttccaaagg ttgtagtgtt   1320
ccaagatgta ttttaagta atattgtaca tgggtgtttc atgtgctgtt gtgtatttgc    1380
tggtggtttg aatataaaca ctatgtatca gtgtcgtccc acagtgggtc ctggggaggt   1440
ttggctgggg agcttaggac actaatccat caggttggac tcgaggtcct gcaccaactg   1500
gcttggaaac tagatgaggc tgtcacaggg ctcagttgca taaaccgatg gtgatggagt   1560
gtaaactggg tctttacact cattttattt tttgtttctg cttttgtttt cttcaatgat   1620
ttgcaaggaa accaaaagct ggcagtgttt gtatgaacct gacagaacac tgtcttcaag   1680
gaaatgcctc attcctgaga ccagtaggtt tgtttttta ggaagttcca atactaggac    1740
cccctacaag tactatggct cctcgaaaac acaaagttaa tgccacagga agcagcagat   1800
ggtaggatgg gatgcacaag agttcctgaa aactaacact gttagtgttt tttttttaac   1860
tcaatatttt ccatgaaaat gcaaccacat gtataatatt tttaattaaa taaaagtttc   1920
ttgtgattgt ttt                                                       1933
```

<210> SEQ ID NO 35
<211> LENGTH: 223
<212> TYPE: PRT
<213> ORGANISM: Mus musculus

<400> SEQUENCE: 35

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
    130                 135                 140

Asn Gly Thr Gln Ile Tyr Val Ile Asp Pro Glu Pro Cys Pro Asp Ser
```

| 145 | | | 150 | | | | 155 | | | | 160 | | |

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
            180                 185                 190

Arg Ser Pro Leu Thr Thr Gly Val Tyr Val Lys Met Pro Thr Glu
            195                 200                 205

Pro Glu Cys Glu Lys Gln Phe Gln Pro Tyr Phe Ile Pro Ile Asn
   210                 215                 220

<210> SEQ ID NO 36
<211> LENGTH: 2033
<212> TYPE: DNA
<213> ORGANISM: Homo sapiens

<400> SEQUENCE: 36

| | | | | | |
|---|---|---|---|---|---|
| cttctgtgtg | tgcacatgtg | taatacatat | ctgggatcaa | agctatctat | ataaagtcct | 60 |
| tgattctgtg | tgggttcaaa | cacatttcaa | agcttcagga | tcctgaaagg | ttttgctcta | 120 |
| cttcctgaag | acctgaacac | cgctcccata | aagccatggc | ttgccttgga | tttcagcggc | 180 |
| acaaggctca | gctgaacctg | gctaccagga | cctggccctg | cactctcctg | ttttttcttc | 240 |
| tcttcatccc | tgtcttctgc | aaagcaatgc | acgtggccca | gcctgctgtg | gtactggcca | 300 |
| gcagccgagg | catcgccagc | tttgtgtgtg | agtatgcatc | tccaggcaaa | gccactgagg | 360 |
| tccgggtgac | agtgcttcgg | caggctgaca | gccaggtgac | tgaagtctgt | gcggcaacct | 420 |
| acatgatggg | gaatgagttg | accttcctag | atgattccat | ctgcacgggc | acctccagtg | 480 |
| gaaatcaagt | gaacctcact | atccaaggac | tgagggccat | ggacacggga | ctctacatct | 540 |
| gcaaggtgga | gctcatgtac | ccaccgccat | actacctggg | cataggcaac | ggaacccaga | 600 |
| tttatgtaat | tgatccagaa | ccgtgcccag | attctgactt | cctcctctgg | atccttgcag | 660 |
| cagttagttc | ggggttgttt | ttttatagct | ttctcctcac | agctgtttct | ttgagcaaaa | 720 |
| tgctaaagaa | aagaagccct | cttacaacag | gggtctatgt | gaaaatgccc | ccaacagagc | 780 |
| cagaatgtga | aaagcaattt | cagccttatt | ttattcccat | caattgagaa | accattatga | 840 |
| agaagagagt | ccatatttca | atttccaaga | gctgaggcaa | ttctaacttt | tttgctatcc | 900 |
| agctattttt | atttgtttgt | gcatttgggg | ggaattcatc | tctctttaat | ataaagttgg | 960 |
| atgcggaacc | caaattacgt | gtactacaat | ttaaagcaaa | ggagtagaaa | gacagagctg | 1020 |
| ggatgttttct | gtcacatcag | ctccactttc | agtgaaagca | tcacttggga | ttaatatggg | 1080 |
| gatgcagcat | tatgatgtgg | gtcaaggaat | taagttaggg | aatggcacag | cccaaagaag | 1140 |
| gaaaaggcag | ggagcgaggg | agaagactat | attgtacaca | ccttatattt | acgtatgaga | 1200 |
| cgtttatagc | cgaaatgatc | ttttcaagtt | aaattttatg | cctttattt | cttaaacaaa | 1260 |
| tgtatgatta | catcaaggct | tcaaaaatac | tcacatggct | atgttttagc | cagtgatgct | 1320 |
| aaaggttgta | ttgcatatat | acatatatat | atatatatat | atatatatat | atatatatat | 1380 |
| atatatatat | atatatattt | taatttgata | gtattgtgca | tagagccacg | tatgtttttg | 1440 |
| tgtatttgtt | aatggtttga | atataaacac | tatatgcag | tgtctttcca | ccttgggtcc | 1500 |
| cagggaagtt | ttgtggagga | gctcaggaca | ctaatacacc | aggtagaaca | caaggtcatt | 1560 |
| tgctaactag | cttggaaact | ggatgaggtc | atagcagtgc | ttgattgcgt | ggaattgtgc | 1620 |
| tgagttggtg | ttgacatgtg | ctttgggggct | tttacaccag | ttcctttcaa | tggtttgcaa | 1680 |
| ggaagccaca | gctggtggta | tctgagttga | cttgacagaa | cactgtcttg | aagacaatgg | 1740 |

```
cttactccag gagacccaca ggtatgacct tctaggaagc tccagttcga tgggcccaat    1800
tcttacaaac atgtggttaa tgccatggac agaagaaggc agcaggtggc agaatggggt    1860
gcatgaaggt ttctgaaaat taacactgct tgtgttttta actcaatatt ttccatgaaa    1920
atgcaacaac atgtataata tttttaatta aataaaaatc tgtggtggtc gttttaaaaa    1980
aaaaaaaaaa aaaaaaaaaa aaaaaaaaaa aaaaaaaaaa aaaaaaaaaa aaa           2033
```

<210> SEQ ID NO 37
<211> LENGTH: 223
<212> TYPE: PRT
<213> ORGANISM: Homo sapiens

<400> SEQUENCE: 37

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 38
<211> LENGTH: 361
<212> TYPE: DNA
<213> ORGANISM: Artificial
<220> FEATURE:
<223> OTHER INFORMATION: Homo sapiens and Mus musculus

<400> SEQUENCE: 38

```
ccatgtcagc catacaggtg gcccagcctg ctgtggtact ggccagcagc cgaggcatcg    60
ccagctttgt gtgtgagtat gcatctccag gcaaagccac tgaggtccgg gtgacagtgc    120
ttcggcaggc tgacagccag gtgactgaag tctgtgcggc aacctacatg atggggaatg    180
agttgacctt cctagatgat ccatctgca cgggcacctc cagtggaaat caagtgaacc    240
```
tcactatcca aggactgagg gccatggaca cgggactcta catctgcaag gtggagctca    300
tgtacccacc gccatactac ctgggcatag gcaacgggac gcagatttat gtcattggtg    360
a                                                                   361

<210> SEQ ID NO 39
<211> LENGTH: 671
<212> TYPE: DNA
<213> ORGANISM: Artificial
<220> FEATURE:
<223> OTHER INFORMATION: Homo sapiens and Mus musculus

<400> SEQUENCE: 39
tggcttgtct tggactccgg aggtacaaag ctcaactgca gctgccttct aggacttggc     60
cttttgtagc cctgctcact cttcttttca tcccagtctt ctctgaagcc atacaggtgg    120
cccagcctgc tgtggtactg gccagcagcc gaggcatcgc cagctttgtg tgtgagtatg    180
catctccagg caaagccact gaggtccggg tgacagtgct tcggcaggct gacagccagg    240
tgactgaagt ctgtgcggca acctacatga tggggaatga gttgaccttc ctagatgatt    300
ccatctgcac gggcacctcc agtggaaatc aagtgaacct cactatccaa ggactgaggg    360
ccatggacac gggactctac atctgcaagg tggagctcat gtacccaccg ccatactacc    420
tgggcatagg caacgggacg cagatttatg tcattgatcc agaaccatgc ccggattctg    480
acttcctcct ttgatccctt gtcgcagtta gcttgggggtt gttttttttac agttcctgg     540 tcactgctgt ttctttgagc aagatgctaa agaaaagaag tcctcttaca cagggtct    600 atgtgaaaat gccccaaca gagccagaat gtgaaaagca atttcagcct tattttattc    660
ccatcaactg a                                                          671

<210> SEQ ID NO 40
<211> LENGTH: 1933
<212> TYPE: DNA
<213> ORGANISM: Artificial
<220> FEATURE:
<223> OTHER INFORMATION: Homo sapiens and Mus musculus

<400> SEQUENCE: 40
ctacacatat gtagcacgta ccttggatca agctgtcta tataaagtcc ccgagtctgt      60
gtgggttcaa acacatctca aggcttctgg atcctgttgg gttttactct gctccctgag    120
gacctcagca catttgcccc ccagccatgg cttgtcttgg actccggagg tacaaagctc    180
aactgcagct gccttctagg acttggcctt ttgtagccct gctcactctt cttttcatcc    240
cagtcttctc tgaagccata caggtggccc agcctgctgt ggtactggcc agcagccgag    300
gcatcgccag ctttgtgtgt gagtatgcat ctccaggcaa agccactgag gtccgggtga    360
cagtgcttcg gcaggctgac agccaggtga ctgaagtctg tgcggcaacc tacatgatgg    420
ggaatgagtt gaccttccta gatgattcca tctgcacggg cacctccagt ggaaatcaag    480
tgaacctcac tatccaagga ctgagggcca tggacacggg actctacatc tgcaaggtgg    540
agctcatgta cccaccgcca tactacctgg gcataggcaa cgggacgcag atttatgtca    600
ttgatccaga accatgcccg gattctgact tcctcctttg atccttgtc gcagttagct    660 tgggggttgtt ttttacagt ttcctggtca ctgctgtttc tttgagcaag atgctaaaga    720
aaagaagtcc tcttacaaca ggggtctatg tgaaaatgcc cccaacagag ccagaatgtg    780
aaaagcaatt tcagccttat tttattccca tcaactgaaa ggccgttat gaagaagaag    840 gagcatactt cagtctctaa aagctgaggc aatttcaact ttccttttct ctccagctat    900

-continued

```
ttttacctgt tgtatattt taaggagagt atgcctctct ttaatagaaa gctggatgca      960
aaattccaat taagcatact acaatttaaa gctaaggagc atgaacagag agctgggata     1020
tttctgttgt gtcagaacca ttttactaaa agcatcactt ggaagcagca taaggatata    1080
gcattatggt gtggggtcaa gggaacatta gggaatggca cagcccaaag aaaggaaggg    1140
ggtgaaggaa gagattatat tgtacacatc ttgtatttac ctgagagatg tttatgactt    1200
aaataatttt taaattttc atgctgttat tttctttaac aatgtataat tacacgaagg     1260
tttaaacatt tattcacaga gctatgtgac atagccagtg gttccaaagg ttgtagtgtt    1320
ccaagatgta tttttaagta atattgtaca tgggtgtttc atgtgctgtt gtgtatttgc    1380
tggtggtttg aatataaaca ctatgtatca gtgtcgtccc acagtgggtc ctggggaggt    1440
ttggctgggg agcttaggac actaatccat caggttggac tcgaggtcct gcaccaactg    1500
gcttggaaac tagatgaggc tgtcacaggg ctcagttgca taaaccgatg gtgatggagt    1560
gtaaactggg tctttacact cattttattt tttgtttctg cttttgtttt cttcaatgat    1620
ttgcaaggaa accaaaagct ggcagtgttt gtatgaacct gacagaacac tgtcttcaag    1680
gaaatgcctc attcctgaga ccagtaggtt tgttttttta ggaagttcca atactaggac    1740 ccctacaag tactatggct cctcgaaaac acaaagttaa tgccacagga agcagcagat     1800
ggtaggatgg gatgcacaag agttcctgaa aactaacact gttagtgttt ttttttaac    1860 tcaatatttt ccatgaaaat gcaaccacat gtataatatt tttaattaaa taaagtttc    1920 ttgtgattgt ttt                                                       1933
```

<210> SEQ ID NO 41
<211> LENGTH: 223
<212> TYPE: PRT
<213> ORGANISM: Artificial
<220> FEATURE:
<223> OTHER INFORMATION: Homo sapiens and Mus musculus

<400> SEQUENCE: 41

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175
```

Tyr Ser Phe Leu Val Thr Ala Val Ser Leu Ser Lys Met Leu Lys Lys
            180                 185                 190

Arg Ser Pro Leu Thr Thr Gly Val Tyr Val Lys Met Pro Thr Glu
        195                 200                 205

Pro Glu Cys Glu Lys Gln Phe Gln Pro Tyr Phe Ile Pro Ile Asn
    210                 215                 220

<210> SEQ ID NO 42
<211> LENGTH: 1518
<212> TYPE: DNA
<213> ORGANISM: Mus musculus

<400> SEQUENCE: 42

| | | | | | |
|---|---|---|---|---|---|
| atgagcaaag | ggtgcttgca | gaaagtctct | gatagtagag | atgaaggcta | ggcagacacc | 60 |
| tgctgtttca | cccgctaagc | tgatggagta | accatggcaa | ctgccaccat | attgttctct | 120 |
| tttctgagga | cagatgctaa | tcagtacagg | tgctttcaga | agagactagg | gtatctatat | 180 |
| agcctggttt | atggatagga | gaggtggtct | tggaaactaa | gcctgggta | gtattcaaga | 240 |
| ttgcaataca | ctgaaaacta | attattgtct | tgttttaca | atctatgtta | gtaaactacc | 300 |
| aatgacattg | ttcagtttaa | gttttgggtg | taatcttcaa | tactgaccgg | aaaacatcca | 360 |
| ggttagttat | gaaaaggcaa | tatgacagaa | agccactttt | gtgtgctgag | agtacaaccc | 420 |
| gagatcgtgt | gtattctagg | caagcactct | accaccgacc | tacatctcca | gcccttctgc | 480 |
| ctgtggttct | tgtcttgta | aagcaatgtc | ttgttgttta | gctgatgctg | gccttgcact | 540 |
| tgctatgtag | ccttcatctg | ctggctgcta | ggactgcaga | tttgtaccac | caataccgga | 600 |
| ctgcaaaccc | actaatttct | aatgatgaag | gcatgtttgt | atagagagct | ggactccttt | 660 |
| cttctgtagt | atacagggag | gaaagagaaa | acaacaaaaa | cagcagcagc | agcagcagca | 720 |
| acaacaacaa | caacaaaaac | cccaaggaca | aggaaagtgt | taagtgaagg | aaagaaggga | 780 |
| ggcagaagag | gtggcaggga | agcaggggaa | gcccacagaa | gttaaagcag | ggttgtctca | 840 |
| acccagagag | gaaatgaccc | tggtgccctc | agctctgtgg | cttccttgac | tgatgtatac | 900 |
| accactctac | cacagtgatg | ccaggaaaag | ggtgaccaat | gcattgacct | gaggttcaac | 960 |
| tgctcctggt | tgacagaggt | acgcttataa | ataagtaggt | aggaaaattt | tgaagcttac | 1020 |
| tttgagagat | gaggcaaggt | tctgcacctc | aagctccagg | aatgtctcga | ctgccattca | 1080 |
| ctatgtttcc | tgcgtgatat | agttctatta | tcaccaaaga | aggcgctgta | ctgacatgta | 1140 |
| ggctaccccc | ttttcttact | gcaggggaga | taaatgaaa | ggaagaatta | tttgccaaaa | 1200 |
| tgacacattt | tatgagagcc | agatcttctt | tttgctatac | cagtattctc | cttgccatag | 1260 |
| ccaactgtct | tcaataaact | atcaataagg | ggatcttgga | gagtgactga | ctacagctga | 1320 |
| aagatgggaa | gtggagtgcc | agggtggatg | ggtggagagg | caaagggtga | agggagtgat | 1380 |
| gagtttgttg | aggggtgagc | ttgcaggagt | tcatccaaga | tgaacctccc | ctggcctcag | 1440 |
| gtgtggccta | atagttcaaa | ccgtggatga | tcatgagccc | actaagtgcc | ctttggactt | 1500 |
| tccatgtcag | ccatacag | | | | | 1518 |

<210> SEQ ID NO 43
<211> LENGTH: 53
<212> TYPE: DNA
<213> ORGANISM: Artificial
<220> FEATURE:
<223> OTHER INFORMATION: PCR primer

<400> SEQUENCE: 43

```
tttaagaagg agatatacat gctcgagatg agcaaagggt gcttgcagaa agt            53
```

<210> SEQ ID NO 44
<211> LENGTH: 45
<212> TYPE: DNA
<213> ORGANISM: Artificial
<220> FEATURE:
<223> OTHER INFORMATION: PCR primer

<400> SEQUENCE: 44

```
accacagcag gctgggccac ctgtatggct gacatggaaa gtcca                    45
```

<210> SEQ ID NO 45
<211> LENGTH: 312
<212> TYPE: DNA
<213> ORGANISM: Homo sapiens

<400> SEQUENCE: 45

```
gtggcccagc ctgctgtggt actggccagc agccgaggca tcgccagctt tgtgtgtgag    60
tatgcatctc caggcaaagc cactgaggtc cgggtgacag tgcttcggca ggctgacagc   120
caggtgacta agtctgtgc ggcaacctac atgatgggga atgagttgac cttcctagat    180
gattccatct gcacgggcac ctccagtgga aatcaagtga acctcactat ccaaggactg   240
agggccatgg acacgggact ctacatctgc aaggtggagc tcatgtaccc accgccatac   300
tacctgggca ta                                                       312
```

<210> SEQ ID NO 46
<211> LENGTH: 44
<212> TYPE: DNA
<213> ORGANISM: Artificial
<220> FEATURE:
<223> OTHER INFORMATION: PCR primer

<400> SEQUENCE: 46

```
tggactttcc atgtcagcca tacaggtggc ccagcctgct gtgg                     44
```

<210> SEQ ID NO 47
<211> LENGTH: 41
<212> TYPE: DNA
<213> ORGANISM: Artificial
<220> FEATURE:
<223> OTHER INFORMATION: PCR primer

<400> SEQUENCE: 47

```
taaatctgcg tcccgttgcc tatgcccagg tagtatggcg g                        41
```

<210> SEQ ID NO 48
<211> LENGTH: 973
<212> TYPE: DNA
<213> ORGANISM: Mus musculus

<400> SEQUENCE: 48

```
ggcaacggga cgcagattta tgtcattggt gagcaaagcc attccactaa gaacaagtct    60
gttgcattat tattgtcttt acaccagaat agttttgttc cttggtttgg agtccttcat   120
agttaggtct gtgatgcata gctaggaatt ccctagtaga tagtagtctt gcttatactg   180
agaagttaca taaccatcac tctgattgca atgaaacgca tttggggatg tgttttttat   240
actgcttgct gatagtctag gacacttgtt cttgaagttt agtcttgtcc ctttgatggc   300
actctgggaa agtcatgtat taaataagta gccagacttc cctatagttt accaatacaa   360
```

-continued

```
gttagggttg actagcaaaa cctggaacct ctaacttcct tttactaccc atgaggaact    420
aggaccccac aattggaaac tctctcagga ggttgatgct tcgtcttctg ttgcagatcc    480
agaaccatgc ccggattctg acttcctcct ttggatcctt gtcgcagtta gcttggggtt    540 gttttttttac agtttcctgg tcactgctgt ttctttgagc aagatggtga gtgtgatgtt   600
gacgtttccc cacagttaat ggggatactt ttagttgtac cctactgacc aattggtgtt    660
gagttgaagc aataaacaag gagcaggaag gatagggtaa agaacacgct agaaccccat    720
gcacttgcct tagaggtttc gggatgacta atactgtacg tgagcatgtt tgacagtgaa    780
tgtttgtgtg cttctgagca gggtttcagt ttgagtaact gtttgaacaa catggagcag    840
ctgttttggt tgtcactgtc atggcaatgt ccttaatcct aggacacaca gcagtctctg    900
ggcaaccctt tctagttaga accacctaga tggattttg tcctttacca agcaccatct     960
cttggtccct ctt                                                       973

<210> SEQ ID NO 49
<211> LENGTH: 42
<212> TYPE: DNA
<213> ORGANISM: Artificial
<220> FEATURE:
<223> OTHER INFORMATION: PCR primer

<400> SEQUENCE: 49
cgccatacta cctgggcata ggcaacggga cgcagattta tg                       42

<210> SEQ ID NO 50
<211> LENGTH: 52
<212> TYPE: DNA
<213> ORGANISM: Artificial
<220> FEATURE:
<223> OTHER INFORMATION: PCR primer

<400> SEQUENCE: 50
ttgttagcag ccggatctca ggcggccgca agagggacca agagatggtg ct            52

<210> SEQ ID NO 51
<211> LENGTH: 29
<212> TYPE: DNA
<213> ORGANISM: Artificial
<220> FEATURE:
<223> OTHER INFORMATION: PCR primer

<400> SEQUENCE: 51
gaaaggctaa taccaggctt gttatgtgc                                      29

<210> SEQ ID NO 52
<211> LENGTH: 28
<212> TYPE: DNA
<213> ORGANISM: Artificial
<220> FEATURE:
<223> OTHER INFORMATION: PCR primer

<400> SEQUENCE: 52
tcaactcatt ccccatcatg taggttgc                                       28

<210> SEQ ID NO 53
<211> LENGTH: 25
<212> TYPE: DNA
<213> ORGANISM: Artificial
<220> FEATURE:
<223> OTHER INFORMATION: PCR primer

<400> SEQUENCE: 53
```
gagtatgcat ctccaggcaa agcca                                          25

<210> SEQ ID NO 54
<211> LENGTH: 25
<212> TYPE: DNA
<213> ORGANISM: Artificial
<220> FEATURE:
<223> OTHER INFORMATION: PCR primer

<400> SEQUENCE: 54
cactgagcta gggagggcat caagg                                          25

<210> SEQ ID NO 55
<211> LENGTH: 25
<212> TYPE: DNA
<213> ORGANISM: Artificial
<220> FEATURE:
<223> OTHER INFORMATION: PCR primer

<400> SEQUENCE: 55
tgtgttaaag caacacagcg tggtc                                          25

<210> SEQ ID NO 56
<211> LENGTH: 25
<212> TYPE: DNA
<213> ORGANISM: Artificial
<220> FEATURE:
<223> OTHER INFORMATION: PCR primer

<400> SEQUENCE: 56
aactgttgtt gccgtttggt ccttg                                          25

<210> SEQ ID NO 57
<211> LENGTH: 25
<212> TYPE: DNA
<213> ORGANISM: Artificial
<220> FEATURE:
<223> OTHER INFORMATION: PCR primer

<400> SEQUENCE: 57
agaagaccat tgcttttggc tgttt                                          25

<210> SEQ ID NO 58
<211> LENGTH: 25
<212> TYPE: DNA
<213> ORGANISM: Artificial
<220> FEATURE:
<223> OTHER INFORMATION: PCR primer

<400> SEQUENCE: 58
acatggaaaa gtgcagaact aaaga                                          25

<210> SEQ ID NO 59
<211> LENGTH: 19
<212> TYPE: DNA
<213> ORGANISM: Artificial
<220> FEATURE:
<223> OTHER INFORMATION: PCR primer

<400> SEQUENCE: 59
accccttgag gttagccct                                                 19

<210> SEQ ID NO 60
<211> LENGTH: 23
<212> TYPE: DNA

<213> ORGANISM: Artificial
<220> FEATURE:
<223> OTHER INFORMATION: PCR primer

<400> SEQUENCE: 60
ttgtagaaca gctatacgac cca                                    23

<210> SEQ ID NO 61
<211> LENGTH: 21
<212> TYPE: DNA
<213> ORGANISM: Artificial
<220> FEATURE:
<223> OTHER INFORMATION: PCR primer

<400> SEQUENCE: 61
atactgtgct aacaggcctc a                                      21

<210> SEQ ID NO 62
<211> LENGTH: 23
<212> TYPE: DNA
<213> ORGANISM: Artificial
<220> FEATURE:
<223> OTHER INFORMATION: PCR primer

<400> SEQUENCE: 62
acccattgtc attaggaagc act                                    23

<210> SEQ ID NO 63
<211> LENGTH: 45
<212> TYPE: DNA
<213> ORGANISM: Artificial
<220> FEATURE:
<223> OTHER INFORMATION: PCR primer

<400> SEQUENCE: 63
gcatcaagct tggtaccgat acagctgaaa gatgggaagt ggagt            45

<210> SEQ ID NO 64
<211> LENGTH: 45
<212> TYPE: DNA
<213> ORGANISM: Artificial
<220> FEATURE:
<223> OTHER INFORMATION: PCR primer

<400> SEQUENCE: 64
acttaatcgt ggaggatgat cacatcccca aatgcgtttc attgc            45

<210> SEQ ID NO 65
<211> LENGTH: 25
<212> TYPE: DNA
<213> ORGANISM: Artificial
<220> FEATURE:
<223> OTHER INFORMATION: PCR primer

<400> SEQUENCE: 65
ccatcacaca acactgatga ggtcc                                  25

<210> SEQ ID NO 66
<211> LENGTH: 25
<212> TYPE: DNA
<213> ORGANISM: Artificial
<220> FEATURE:
<223> OTHER INFORMATION: PCR primer

<400> SEQUENCE: 66
cacatcccca aatgcgtttc attgc                                  25

```
<210> SEQ ID NO 67
<211> LENGTH: 25
<212> TYPE: DNA
<213> ORGANISM: Artificial
<220> FEATURE:
<223> OTHER INFORMATION: PCR primer

<400> SEQUENCE: 67
acagctgaaa gatgggaagt ggagt                                    25

<210> SEQ ID NO 68
<211> LENGTH: 25
<212> TYPE: DNA
<213> ORGANISM: Artificial
<220> FEATURE:
<223> OTHER INFORMATION: PCR primer

<400> SEQUENCE: 68
cttccacatg agcgtggtca gggcc                                    25

<210> SEQ ID NO 69
<211> LENGTH: 25
<212> TYPE: DNA
<213> ORGANISM: Artificial
<220> FEATURE:
<223> OTHER INFORMATION: PCR primer

<400> SEQUENCE: 69
ccaagggact attttagatg ggcag                                    25

<210> SEQ ID NO 70
<211> LENGTH: 26
<212> TYPE: DNA
<213> ORGANISM: Artificial
<220> FEATURE:
<223> OTHER INFORMATION: PCR primer

<400> SEQUENCE: 70
gaagctacaa gctcctaggt aggggg                                   26

<210> SEQ ID NO 71
<211> LENGTH: 23
<212> TYPE: DNA
<213> ORGANISM: Artificial
<220> FEATURE:
<223> OTHER INFORMATION: PCR primer

<400> SEQUENCE: 71
acgggttggc tcaaaccatt aca                                      23
```

METHOD OF USING A GENETICALLY MODIFIED MOUSE THAT EXPRESSES A HUMANIZED CTLA-4 GENE

CLAIM OF PRIORITY

This application claims priority to International Application No. PCT/CN2017/099577, filed on Aug. 30, 2017, which claims the benefit of Chinese Patent Application App. No. 201610784999.2, filed on Aug. 31, 2016, and App. No. 201710757917.X, filed on Aug. 29, 2017. The entire contents of the foregoing are incorporated herein by reference.

TECHNICAL FIELD

This disclosure relates to genetically modified animal expressing human or chimeric (e.g., humanized) Cytotoxic T lymphocyte antigen 4 (CTLA-4 or CTLA4), and methods of use thereof.

BACKGROUND

Cancer is currently one of the diseases that have the highest human mortality. According to the World Health Organization statistical data, in 2012 the number of global cancer incidence and death cases reached 14 million and 8.2 million, respectively. In China, the newly diagnosed cancer cases are 3.07 million, and the death toll is 2.2 million.

In recent years, antibody drug development for immunological checkpoints is considered to be a potential target for the treatment of various types of cancers. The traditional drug research and development typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to CTLA-4 humanized animal model. The animal model can express human CTLA-4 or chimeric CTLA-4 (e.g., humanized CTLA-4) protein in its body. It can be used in the studies on the function of CTLA-4 gene, and can be used in the screening and evaluation of anti-human CTLA-4 antibodies. In addition, the animal models prepared by the methods described herein can be used in drug screening, pharmacodynamics studies, treatments for immune-related diseases, and cancer therapy for human CTLA-4 target sites; in addition, they can be used to facilitate the development and design of new drugs, and save time and cost. In summary, this disclosure provides a powerful tool for studying the function of CTLA-4 protein and screening for cancer drugs.

Furthermore, the disclosure also provides CTLA-4 gene knockout mice. Moreover, the mice described in the present disclosure can be mated with the mice containing other human or chimeric genes (e.g., chimeric PD-1 or other immunomodulatory factors), so as to obtain a mouse having a human or chimeric protein at both alleles of the endogenous gene. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric cytotoxic T-lymphocyte-associated protein 4 (CTLA-4). In some embodiments, the sequence encoding the human or chimeric CTLA-4 is operably linked to an endogenous regulatory element at the endogenous CTLA-4 gene locus in the at least one chromosome. In some embodiments, the sequence encoding a human or chimeric CTLA-4 comprises a sequence encoding an amino acid sequence that is at least 70%, 75%, 80%, 85%, 90%, 95%, 99%, or 100% identical to human CTLA-4 (NP_005205.2) (SEQ ID NO: 37). In some embodiments, the sequence encoding a human or chimeric CTLA-4 comprises a sequence encoding an amino acid sequence that is at least 70%, 75%, 80%, 85%, 90%, 95%, 99%, or 100% identical to SEQ ID NO: 41. In some embodiments, the sequence encoding a human or chimeric CTLA-4 comprises a sequence encoding an amino acid sequence that corresponds to amino acids 42-145 of SEQ ID NO: 41.

In some embodiments, the animal is a mammal, e.g., a monkey, a rodent or a mouse. In some embodiments, the animal is a C57BL/6 mouse. In some embodiments, the animal does not express endogenous CTLA-4. In some embodiments, the animal has one or more cells expressing human or chimeric CTLA-4. In some embodiments, the animal has one or more cells expressing human or chimeric CTLA-4, and human or endogenous CD80 can bind to the expressed human or chimeric CTLA-4 and downregulate immune response in the animal. In some embodiments, the animal has one or more cells expressing human or chimeric CTLA-4, and human or endogenous CD86 can bind to the expressed human or chimeric CTLA-4 and downregulate immune response in the animal.

In another aspect, the disclosure relates to are genetically-modified, non-human animals, wherein the genome of the animal comprises a replacement, at an endogenous CTLA-4 gene locus, of a sequence encoding a region of endogenous CTLA-4 with a sequence encoding a corresponding region of human CTLA-4. In some embodiments, the sequence encoding the corresponding region of human CTLA-4 is operably linked to an endogenous regulatory element at the endogenous CTLA-4 locus, and one or more cells of the animal expresses a chimeric CTLA-4. In some embodiments, the animal does not express endogenous CTLA-4. In some embodiments, the region of endogenous CTLA-4 is the extracellular region of CTLA-4. In some embodiments, the animal has one or more cells expressing a chimeric CTLA-4 having an extracellular region, a transmembrane region, and a cytoplasmic region, wherein the extracellular region comprises a sequence that is at least 50%, 60%, 70%, 80%, 90%, 95%, or 99% identical to the extracellular region of human CTLA-4. In some embodiments, the extracellular region of the chimeric CTLA-4 has a sequence that has at least 10, 20, 30, 40, 50, 60, 70, 80, 90, or 100 contiguous amino acids that are identical to a contiguous sequence present in the extracellular region of human CTLA-4. In some embodiments, the animal is a mouse, and the sequence encoding the region of endogenous CTLA-4 is Exon 1, Exon 2, Exon 3, and/or Exon 4 of the endogenous mouse CTLA-4 gene. In some embodiments, the animal is heterozygous with respect to the replacement at the endogenous CTLA-4 gene locus. In some embodiments, the animal is homozygous with respect to the replacement at the endogenous CTLA-4 gene locus.

In another aspect, the disclosure relates to methods for making a genetically-modified, non-human animal, including: replacing in at least one cell of the animal, at an endogenous CTLA-4 gene locus, a sequence encoding a region of an endogenous CTLA-4 with a sequence encoding a corresponding region of human CTLA-4. In some embodiments, the sequence encoding the corresponding region of human CTLA-4 comprises exon 1, exon 2, exon 3, and/or exon 4 of a human CTLA-4 gene. In some embodiments, the sequence encoding the corresponding region of CTLA-4 comprises exon 2 of a human CTLA-4 gene. In some embodiments, the sequence encoding the corresponding region of human CTLA-4 encodes amino acids 42-145 of SEQ ID NO: 41. In some embodiments, the region is located within the extracellular region of CTLA-4. In some embodiments, the animal is a mouse, and the sequence encoding the region of the endogenous CTLA-4 locus is Exon 2 of mouse CTLA-4 gene.

In one aspect, the disclosure relates to are non-human animals including at least one cell comprising a nucleotide sequence encoding a chimeric CTLA-4 polypeptide, wherein the chimeric CTLA-4 polypeptide comprises at least 50 contiguous amino acid residues that are identical to the corresponding contiguous amino acid sequence of a human CTLA-4, wherein the animal expresses the chimeric CTLA-4. In some embodiments, the chimeric CTLA-4 polypeptide has at least 50 contiguous amino acid residues that are identical to the corresponding contiguous amino acid sequence of a human CTLA-4 extracellular region. In some embodiments, the chimeric CTLA-4 polypeptide comprises a sequence that is at least 90%, 95%, or 99% identical to amino acids 42-145 of SEQ ID NO: 41. In some embodiments, the nucleotide sequence is operably linked to an endogenous CTLA-4 regulatory element of the animal. In some embodiments, the chimeric CTLA-4 polypeptide comprises an endogenous CTLA-4 transmembrane region and/or an endogenous CTLA-4 cytoplasmic region. In some embodiments, the nucleotide sequence is integrated to an endogenous CTLA-4 gene locus of the animal. In some embodiments, the chimeric CTLA-4 has at least one mouse CTLA-4 activity and/or at least one human CTLA-4 activity.

In another aspect, the disclosure relates to methods of making a genetically-modified mouse cell that expresses a chimeric CTLA-4, the method including: replacing, at an endogenous mouse CTLA-4 gene locus, a nucleotide sequence encoding a region of mouse CTLA-4 with a nucleotide sequence encoding a corresponding region of human CTLA-4, thereby generating a genetically-modified mouse cell that includes a nucleotide sequence that encodes the chimeric CTLA-4, wherein the mouse cell expresses the chimeric CTLA-4. In some embodiments, the chimeric CTLA-4 includes an extracellular region of mouse CTLA-4 comprising a mouse signal peptide sequence, an extracellular region of human CTLA-4, a transmembrane and/or a cytoplasmic region of a mouse CTLA-4. In some embodiments, the nucleotide sequence encoding the chimeric CTLA-4 is operably linked to an endogenous CTLA-4 regulatory region, e.g., promoter.

In some embodiments, the animals provided herein further include a sequence encoding an additional human or chimeric protein. In some embodiments, the additional human or chimeric protein is programmed cell death protein 1 (PD-1), TNF Receptor Superfamily Member 4 (OX40), Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA). In some embodiments, the animal or mouse further comprises a sequence encoding an additional human or chimeric protein. In some embodiments, the additional human or chimeric protein is programmed cell death protein 1 (PD-1), OX40, LAG-3, TIM-3, PD-L1, 4-1BB, CD27, CD28, CD47, TIGIT, CD27, GITR, or BTLA.

In another aspect, the disclosure relates to methods of determining effectiveness of an anti-CTLA-4 antibody for the treatment of cancer, including: administering the anti-CTLA-4 antibody to the animal of any one of the embodiments described herein, wherein the animal has a tumor, and determining the inhibitory effects of the anti-CTLA-4 antibody to the tumor. In some embodiments, the tumor comprises one or more tumor cells that express CD80 or CD86. In some embodiments, the tumor comprises one or more cancer cells that are injected into the animal. In some embodiments, determining the inhibitory effects of the anti-CTLA-4 antibody to the tumor involves measuring the tumor volume in the animal. In some embodiments, the tumor cells are melanoma cells, non-small cell lung carcinoma (NSCLC) cells, small cell lung cancer (SCLC) cells, bladder cancer cells, and/or prostate cancer cells (e.g., metastatic hormone-refractory prostate cancer).

In another aspect, the disclosure relates to methods of determining effectiveness of an anti-CTLA-4 antibody and an additional therapeutic agent for the treatment of a tumor, including: administering the anti-CTLA-4 antibody and the additional therapeutic agent to the animal of any one of the embodiments described above, wherein the animal has a tumor, and determining the inhibitory effects on the tumor. In some embodiments, the animal further comprises a sequence encoding a human or chimeric programmed cell death protein 1 (PD-1). In some embodiments, the additional therapeutic agent is an anti-PD-1 antibody. In some embodiments, the tumor comprises one or more tumor cells that express CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells).

The disclosure relates to proteins comprising an amino acid sequence, wherein the amino acid sequence is one of the following: (a) an amino acid sequence set forth in SEQ ID NO: 41; (b) an amino acid sequence that is at least 90% identical to SEQ ID NO: 41; (c) an amino acid sequence that is at least 91%, 92%, 93%, 94%, 95%, 96%, 97%, 98%, or 99% identical to SEQ ID NO: 41; (d) an amino acid sequence that is different from the amino acid sequence set forth in SEQ ID NO: 41 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 41. In some embodiments, provided herein are cells comprising the proteins disclosed herein. In some embodiments, provided herein are animals having the proteins disclosed herein.

In another aspect, the disclosure relates to nucleic acids comprising a nucleotide sequence, wherein the nucleotide sequence is one of the following: (a) a sequence that encodes the protein of claim 54; (b) SEQ ID NO: 39; (c) SEQ ID NO: 40; (d) a sequence that is at least 90% identical to SEQ ID NO: 39 or SEQ ID NO: 40; (e) a sequence that is at least 91%, 92%, 93%, 94%, 95%, 96%, 97%, 98%, or 99% identical to SEQ ID NO: 39; and (f) a sequence that is at least 91%, 92%, 93%, 94%, 95%, 96%, 97%, 98%, or 99% identical to SEQ ID NO: 40. In some embodiments, provided herein are cells comprising the nucleic acids disclosed herein. In some embodiments, provided herein are animals having the nucleic acids disclosed herein.

In another aspect, the disclosure relates to a targeting vector, including a) a DNA fragment homologous to the 5' end of a region to be altered (5' arm), which is selected from the CTLA-4 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CTLA-4 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000067.6; c) the DNA fragment homologous to the 3' end of the region to be altered (3' arm/receptor) is selected from the nucleotide sequences that have at least 90% homology to the NCBI accession number NC_000067.6.

In some embodiments, a) the DNA fragment homologous to the 5' end of a region to be altered (5' arm/receptor) is selected from the nucleotides from the position 60910913 to the position 60912430 of the NCBI accession number NC_000067.6; c) the DNA fragment homologous to the 3' end of the region to be altered (3' arm/receptor) is selected from the nucleotides from the position 60912743 to the position 60913715 of the NCBI accession number NC_000067.6.

In some embodiments, a length of the selected genomic nucleotide sequence is 1.5 kb and 1 kb. In some embodiments, the region to be altered is exon 2 of CTLA-4 gene.

In some embodiments, the sequence of the 5' arm is shown in SEQ ID NO: 42. In some embodiments, the sequence of the 3' arm is shown in SEQ ID NO: 48.

In some embodiments, the targeting vector further includes a selectable gene marker.

In some embodiments, the target region is derived from human. In some embodiments, the target region is a part or entirety of the nucleotide sequence of a humanized CTLA-4. In some embodiments, the nucleotide sequence is shown as one or more of the first exon, the second exon, the third exon, and the fourth exon of the human CTLA-4.

In some embodiments, the nucleotide sequence of the human CTLA-4 encodes the human CTLA-4 protein with the NCBI accession number NP_005205.2. In some embodiments, the target region is shown in SEQ ID NO: 45.

The disclosure also relates to a cell including the targeting vector as described herein.

In another aspect, the disclosure relates to an sgRNA sequence for constructing a humanized animal model, wherein the sgRNA sequence targets the CTLA-4 gene, the sgRNA is unique on the target sequence of the CTLA-4 gene to be altered, and meets the sequence arrangement rule of 5'-NNN (20)-NGG3' or 5'-CCN-N(20)-3'. In some embodiments, the targeting site of the sgRNA in the mouse CTLA-4 gene is located on the exon 2 of the mouse CTLA-4 gene.

In another aspect, the disclosure relates to an sgRNA sequence for constructing a humanized animal model, wherein an upstream sequence thereof is shown as SEQ ID NO: 25, and a downstream sequence thereof is shown as SEQ ID NO: 27, and the sgRNA sequence recognizes a 5' targeting site.

The disclosure also relates to an sgRNA sequence for constructing a humanized animal model, wherein an upstream sequence thereof is shown as SEQ ID NO: 26, which is obtained by adding TAGG to the 5' end of SEQ ID NO: 25; a downstream sequence thereof is shown as SEQ ID NO: 28, which is obtained by adding AAAC to the 5' end of SEQ ID NO: 27, and the sgRNA sequence recognizes a 5' targeting site.

The disclosure also relates to an sgRNA sequence for constructing a humanized animal model, wherein an upstream sequence thereof is shown as SEQ ID NO: 29, and a downstream sequence thereof is shown as SEQ ID NO: 31, and the sgRNA sequence recognizes a 3' targeting site.

The disclosure further relates to an sgRNA sequence for constructing a humanized animal model, wherein an upstream sequence thereof is shown as SEQ ID NO: 30, which is obtained by adding TAGG to the 5' end of SEQ ID NO: 29; a downstream sequence thereof is shown as SEQ ID NO: 32, which is obtained by adding AAAC to the 5' end of SEQ ID NO: 31, and the sgRNA sequence recognizes a 3' targeting site.

In another aspect, the disclosure relates to a construct including the sgRNA sequence as described herein.

The disclosure also relates to a cell comprising the construct as described herein.

In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to a method for establishing a CTLA-4 gene humanized animal model. The methods include the steps of (a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of CTLA-4 gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a CTLA-4 gene humanized animal model to obtain a CTLA-4 gene genetically modified humanized mouse;

(b) mating the CTLA-4 gene genetically modified humanized mouse obtained in step (a) with another humanized mouse, and then screening to obtain a double humanized mouse model.

In some embodiments, in step (b), the CTLA-4 gene genetically modified humanized mouse obtained in step (a) is mated with a PD-1 humanized mouse to obtain a CTLA-4 and PD-1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CTLA-4 gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In another aspect, the disclosure relates to a CTLA-4 amino acid sequence of a humanized mouse, wherein the amino acid sequence is selected from the group consisting of:

a) an amino acid sequence shown in SEQ ID NO: 41;

b) an amino acid sequence having a homology of at least 90% with the amino acid sequence shown in SEQ ID NO: 41;

c) an amino acid sequence encoded by a nucleic acid sequence, wherein the nucleic acid sequence is able to hybridize to a nucleotide sequence encoding the amino acid shown in SEQ ID NO: 41 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 41;

e) an amino acid sequence that is different from the amino acid sequence shown in SEQ ID NO: 41 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 41.

The disclosure also relates to a CTLA-4 DNA sequence of a humanized mouse, wherein the DNA sequence is selected from the group consisting of:

a) a DNA sequence that encodes the CTLA-4 amino acid sequence of a humanized mouse;

b) a DNA sequence that is shown in SEQ ID NO: 40;

c) a DNA sequence having a CDS encoding sequence as shown in SEQ ID NO: 39;

d) a DNA sequence that is able to hybridize to the nucleotide sequence as shown in SEQ ID NO: 40 or SEQ ID NO: 39 under a low stringency condition;

e) a DNA sequence that has a homology of at least 90% with the nucleotide sequence as shown in SEQ ID NO: 40 or SEQ ID NO: 39;

f) a DNA sequence that encodes an amino acid sequence, wherein the amino acid sequence has a homology of at least 90% with the amino acid shown in SEQ ID NO: 41;

g) a DNA sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 41;

h) a DNA sequence that encodes an amino acid sequence, wherein the amino acid sequence is different from the amino acid sequence shown in SEQ ID NO: 41 by no more than 10, 9, 8, 7, 6, 5, 4, 3, 2 or no more than 1 amino acid; and/or i) a DNA sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 41.

The disclosure further relates to a CTLA-4 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CTLA-4 gene function, human CTLA-4 antibodies, the drugs or efficacies for human CTLA-4 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 20A and 20B show that the mice numbered D-1 to D-13 and D-15 to D-16 are homozygous for CTLA-4 gene. FIGS. 20C and 20D show that the mice numbered D-1 to D-16 are homozygous for PD-1 gene. The results of the two groups show that 15 mice numbered D-1 to D-13 and D-15 to D-16 are homozygous for double genes.

FIG. 25 shows the alignment between mouse CTLA-4 amino acid sequence (NP_033973.2; SEQ ID NO:35) and human CTLA-4 amino acid sequence (NP_005205.2; SEQ ID NO:37).

SEQUENCE LISTING

Figure 1B:
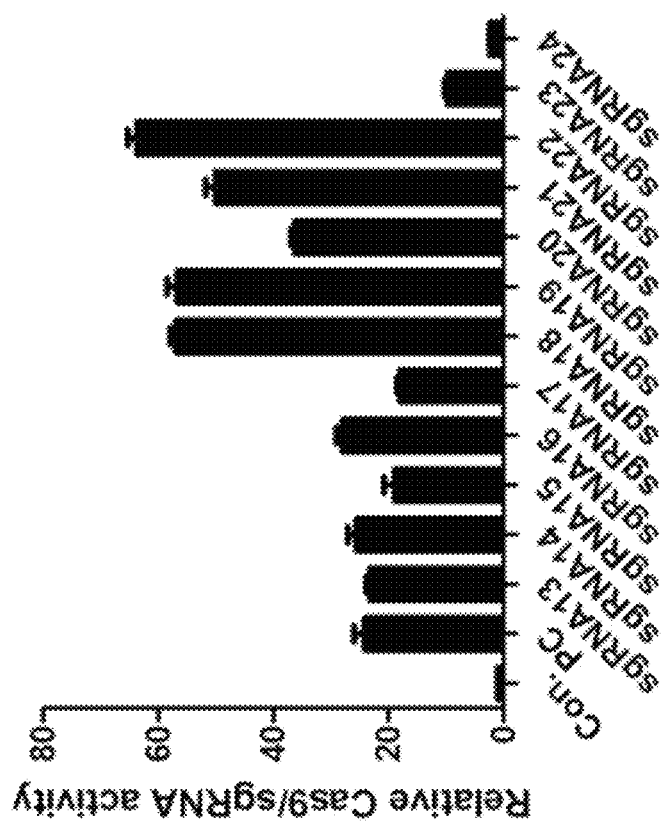
FIG. 1B is a graph showing 3' terminal target site sgRNA activity test results (sgRNA13-sgRNA24) (Con is a negative control; and PC is a positive control).

The instant application contains a Sequence Listing which has been submitted electronically in ASCII format and is hereby incorporated by reference in its entirety. Said ASCII copy, created on May 22, 2019, is named UPDATED SEQ.txt and is 31,062 bytes in size.

DETAILED DESCRIPTION

This disclosure relates to transgenic non-human animal with human or chimeric (e.g., humanized) Cytotoxic T lymphocyte antigen 4 (CTLA-4 or CTLA4), and methods of use thereof.

Cytotoxic T-lymphocyte-associated protein 4 (CTLA-4 or CTLA4), also known as CD152 (cluster of differentiation 152), is a protein receptor that, functioning as an immune checkpoint, downregulates immune responses. CTLA-4 is constitutively expressed in Tregs but is upregulated in conventional T cells after activation. It acts as an "off" switch when bound to CD80 or CD86 on the surface of antigen-presenting cells.

Experimental animal disease model is an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models not only have various important applications. Due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986), each of which is incorporated herein in its entirety by reference.

Cytotoxic T Lymphocyte Antigen 4 (CTLA-4)

Cytotoxic T lymphocyte antigen 4 (CTLA-4) is a transmembrane protein encoded by the CTLA-4 gene. It is expressed in activated CD4+ and CD8+ T cells. CTLA-4 binds to its ligand B7 molecule (CD80 or CD86) to produce inhibitory signals that inhibit T cell activation and protect tumor cells from the attacks from T lymphocytes. Thus, blocking the immune effect of CTLA-4 is able to stimulate the proliferation of immune cells, thereby inducing or enhancing the anti-tumor immune response.

Figure 3:
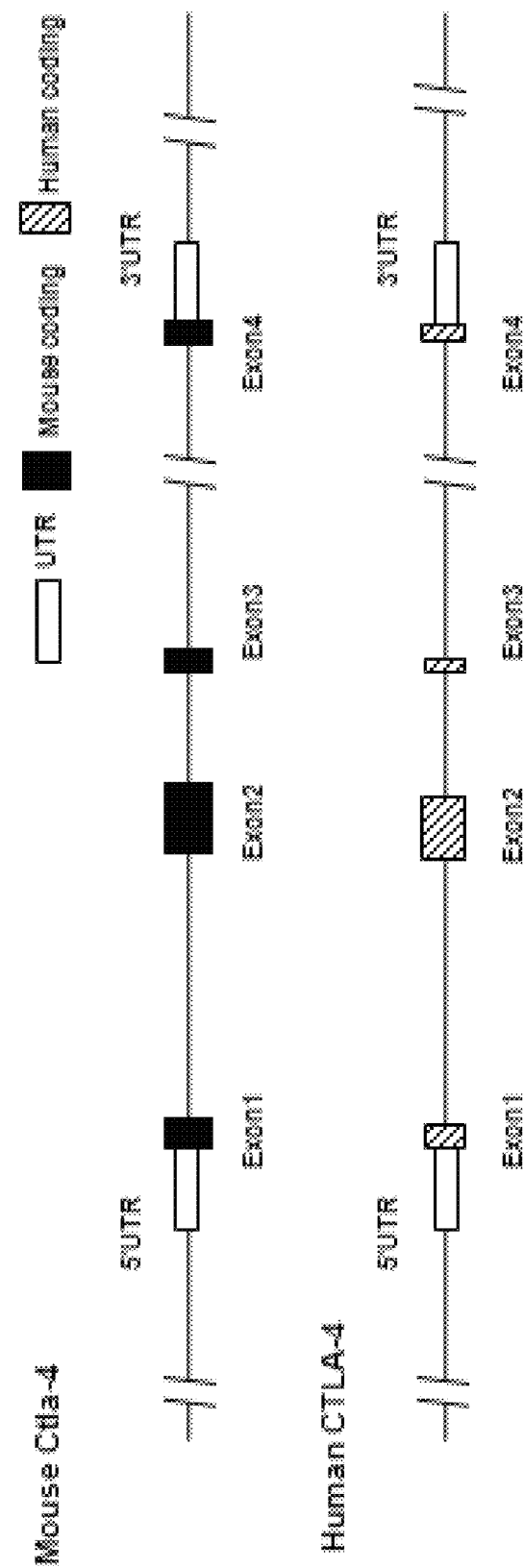
FIG. 3 is a schematic diagram showing comparison of human and mouse CTLA-4 genes.

In human genomes, CTLA-4 gene locus has 4 exons, exon 1, exon 2, exon 3, and exon 4 (FIG. 3). The CTLA-4 protein also has an extracellular region, a transmembrane region, and a cytoplasmic region, and the signal peptide is located at the extracellular region of CTLA-4. The nucleotide sequence for human CTLA-4 mRNA is NM_005214.4 (SEQ ID NO:36), the amino acid sequence for human CTLA-4 is NP_005205.2 (SEQ ID NO:37). The location for each exon and each region in human CTLA-4 nucleotide sequence and amino acid sequence is listed below:

TABLE 1

| Human CTLA-4 (approximate location) | NM_005214.4 (SEQ ID NO: 36) | NP_005205.2 (SEQ ID NO: 37) |
|---|---|---|
| Exon 1 | 1-264 | 1-36 |
| Exon 2 | 265-612 | 37-152 |
| Exon 3 | 613-722 | 153-189 |
| Exon 4 | 723-1975 | 190-223 |
| Signal peptide | 156-260 | 1-35 |
| Extracellular region (excluding signal peptide region) | 261-638 | 36-161 |
| Transmembrane region | 639-701 | 162-182 |
| Cytoplasmic region | 702-824 | 183-223 |
| Donor region in Example 2 | 273-584 | 40-143 |

Similarly, in mice, the CTLA-4 gene locus has 4 exons as well, exon 1, exon 2, exon 3, and exon 4 (FIG. 3). The CTLA-4 protein also has an extracellular region, a transmembrane region, and a cytoplasmic region, and the signal peptide is located at the extracellular region of CTLA-4. The nucleotide sequence for mouse CTLA-4 mRNA is NM_009843.4 (SEQ ID NO: 34), the amino acid sequence for mouse CTLA-4 is NP_033973.2 (SEQ ID NO:35). The location for each exon and each region in the CTLA-4 nucleotide sequence and amino acid sequence is listed below:

TABLE 2

| Mouse CTLA-4 (approximate location) | NM_009843.4 (SEQ ID NO: 34) | NP_033973.2 (SEQ ID NO: 35) |
|---|---|---|
| Exon 1 | 1-255 | 1-36 |
| Exon 2 | 256-603 | 37-152 |
| Exon 3 | 604-713 | 153-189 |
| Exon 4 | 714-1933 | 190-223 |
| Signal peptide | 147-257 | 1-37 |
| Extracellular region (excluding signal peptide region) | 258-629 | 38-161 |
| Transmembrane region | 630-704 | 162-186 |
| Cytoplasmic region | 705-815 | 187-223 |
| Replaced region in Example 2 | 264-575 | 40-143 |

The mouse CTLA-4 gene (Gene ID: 12477) is located in Chromosome 1 of the mouse genome, which is located from 60/909,025 to 60/915,832 of NC_000067.6 (GRCm38.p4 (GCF_000001635.24)). The 5'-UTR is from 60/909,025 to 60/909,170, exon 1 is from 60/909,171 to 60/909,279, the first intron is from 60/909,280 to 60/912,422, exon 2 is from 60/912,423 to 60/912,770, the second intron is from 60/912,771 to 60/913,218, exon 3 is from 60/913,219 to 60/913,328, the third intron is from 60/913,329 to 60/914,612, exon 4 is from 60/914,613 to 60/914,717, the 3'-UTR is from 60/914,718 to 60/915,832, base on transcript NM_009843.4. All relevant information for mouse CTLA-4 locus can be found in the NCBI website with Gene ID: 12477, which is incorporated by reference herein in its entirety.

FIG. 25 shows the alignment between mouse CTLA-4 amino acid sequence (NP_033973.2; SEQ ID NO:35) and human CTLA-4 amino acid sequence (NP_005205.2; SEQ ID NO:37). Thus, the corresponding amino acid residue or region between human and mouse CTLA-4 can also be found in FIG. 25.

CTLA-4 genes, proteins, and locus of the other species are also known in the art. For example, the gene ID for CTLA-4 in *Rattus norvegicus* is 63835, the gene ID for CTLA-4 in *Macaca mulatta* (Rhesus monkey) is 705673, the gene ID for CTLA-4 in *Sus scrofa* (pig) is 397286. The relevant information for these genes (e.g., intron sequences, exon sequences, amino acid residues of these proteins) can be found, e.g., in NCBI database.

The present disclosure provides human or chimeric (e.g., humanized) CTLA-4 nucleotide sequence and/or amino acid sequences. In some embodiments, the entire sequence of mouse exon 1, exon 2, exon 3, exon 4, signal peptide, extracellular region, transmembrane region, and/or cytoplasmic region are replaced by the corresponding human sequence. In some embodiments, a "region" or "portion" of mouse exon 1, exon 2, exon 3, exon 4, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, signal peptide, extracellular region, transmembrane region, or cytoplasmic region. In some embodiments, a region, a portion, or the entire sequence of mouse exon 2 and/or exon 3 are replaced by the human exon 2 and/or exon 3.

In some embodiments, the present disclosure also provides a chimeric (e.g., humanized) CTLA-4 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CTLA-4 mRNA sequence (e.g., SEQ ID NO: 34), or mouse CTLA-4 amino acid sequence (e.g., SEQ ID NO: 35); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CTLA-4 mRNA sequence (e.g., SEQ ID NO: 36), or human CTLA-4 amino acid sequence (e.g., SEQ ID NO: 37).

In some embodiments, the sequence encoding amino acids 40-143 of mouse CTLA-4 (SEQ ID NO:35) is replaced. In some embodiments, the sequence is replaced by a sequence encoding a corresponding region of human CTLA-4 (e.g., amino acids 40-143 of human CTLA-4 (SEQ ID NO: 37)).

In some embodiments, the nucleic acids as described herein are operably linked to a promoter or regulatory element, e.g., an endogenous mouse CTLA-4 promoter, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CTLA-4 nucleotide sequence (e.g., NM_009843.4 (SEQ ID NO: 34)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CTLA-4 nucleotide sequence (e.g., NM_009843.4 (SEQ ID NO: 34)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CTLA-4 nucleotide sequence (e.g., NM_005214.4 (SEQ ID NO:36)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CTLA-4 nucleotide sequence (e.g., NM_005214.4 (SEQ ID NO:36)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CTLA-4 amino acid sequence (e.g., NP_033973.2 (SEQ ID NO:35)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CTLA-4 amino acid sequence (e.g., NP_033973.2 (SEQ ID NO:35)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CTLA-4 amino acid sequence (e.g., NP_005205.2 (SEQ ID NO:37)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CTLA-4 amino acid sequence (e.g., NP_005205.2 (SEQ ID NO:37)).

The present disclosure also provides a humanized CTLA-4 mouse amino acid sequence, wherein the amino acid sequence is selected from the group consisting of:
a) an amino acid sequence shown in SEQ ID NO: 41;
b) an amino acid sequence having a homology of at least 90% with or at least 90% identical to the amino acid sequence shown in SEQ ID NO: 41;
c) an amino acid sequence encoded by a nucleic acid sequence, wherein the nucleic acid sequence is able to hybridize to a nucleotide sequence encoding the amino acid shown in SEQ ID NO: 41 under a low stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 41;
e) an amino acid sequence that is different from the amino acid sequence shown in SEQ ID NO: 41 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 41.

The present disclosure also relates to a CTLA-4 DNA sequence, wherein the DNA sequence can be selected from the group consisting of:
a) a DNA sequence as shown in SEQ ID NO: 39, or a DNA sequence encoding a homologous CTLA-4 amino acid sequence of a humanized mouse;
b) a DNA sequence that is shown in SEQ ID NO: 40;
c) a DNA sequence that is able to hybridize to the nucleotide sequence as shown in SEQ ID NO: 39 or SEQ ID NO: 40 under a low stringency condition;
d) a DNA sequence that has a homology of at least 90% or at least 90% identical to the nucleotide sequence as shown in SEQ ID NO: 39 or SEQ ID NO: 40;
e) a DNA sequence that encodes an amino acid sequence, wherein the amino acid sequence has a homology of at least 90% with or at least 90% identical to the amino acid sequence shown in SEQ ID NO: 41;
f) a DNA sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 41;
g) a DNA sequence that encodes an amino acid sequence, wherein the amino acid sequence is different from the amino acid sequence shown in SEQ ID NO: 41 by no more than 10, 9, 8, 7, 6, 5, 4, 3, 2 or no more than 1 amino acid; and/or
h) a DNA sequence that encodes an amino acid sequence, wherein the amino acid sequence comprises a substitution, a deletion and/or insertion of one or more amino acids to the amino acid sequence shown in SEQ ID NO: 41.

The present disclosure further relates to a CTLA-4 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 40 or SEQ ID NO: 39.

The disclosure also provides an amino acid sequence that has a homology of at least 90% with, or at least 90% identical to the sequence shown in SEQ ID NO: 41, and has protein activity. In some embodiments, the homology with the sequence shown in SEQ ID NO: 41 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 41 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

In some embodiments, the amino acid sequence (i) comprises an amino acid sequence; or (ii) consists of an amino acid sequence, wherein the amino acid sequence comprises any one of the sequences mentioned above.

The disclosure also provides a nucleotide sequence that has a homology of at least 90%, or at least 90% identical to the sequence shown in SEQ ID NO: 40, and encodes a polypeptide that has protein activity. In some embodiments, the homology with the sequence shown in SEQ ID NO: 40 is at least about 90%, 91%, 92%, 93%, 94%, 95%, 96%, 97%, 98%, or at least 99%. In some embodiments, the foregoing homology is at least bout 50%, 51%, 52%, 53%, 54%, 55%, 56%, 57%, 58%, or at least about 59%.

In some embodiments, the percentage identity with the sequence shown in SEQ ID NO: 40 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or humanized CTLA-4 from an endogenous non-human CTLA-4 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous CTLA-4 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiment, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CTLA-4 gene or a humanized CTLA-4 nucleic acid. In some embodiments, at least one or more portions of the gene or the nucleic acid is from the human CTLA-4 gene, at least one or more portions of the gene or the nucleic acid is from a non-human CTLA-4 gene. In some embodiments, the gene or the nucleic acid comprises a sequence that encodes a CTLA-4 protein. The encoded CTLA-4 protein is functional or has at least one activity of the human CTLA-4 protein or the non-human CTLA-4 protein, e.g., binding to human or non-human CD80 and/or CD86, regulate immune response, and/or downregulate immune response when bound to CD80 or CD86.

In some embodiments, the chimeric protein or the chimeric polypeptide is a humanized CTLA-4 protein or a humanized CTLA-4 polypeptide. In some embodiments, at least one or more portions of the amino acid sequence of the protein or the polypeptide is from a human CTLA-4 protein, and at least one or more portions of the amino acid sequence of the protein or the polypeptide is from a non-human CTLA-4 protein. The humanized CTLA-4 protein or the humanized CTLA-4 polypeptide is functional or has at least one activity of the human CTLA-4 protein or the non-human CTLA-4 protein The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In another aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), which is incorporated by reference in its entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CTLA-4 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CTLA-4 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. In some embodiments, the mouse can include a replacement of all or part of mature CTLA-4 coding sequence with human mature CTLA-4 coding sequence. These genetically modified animals are described, e.g., in US20150106961, which is incorporated by reference in its entirety.

Genetically modified non-human animals that comprise a modification of an endogenous non-human CTLA-4 locus. In some embodiments, the modification can comprise a human nucleic acid sequence encoding at least a portion of a mature CTLA-4 protein (e.g., at least 10%, 20%, 30%, 40%, 50%, 60%, 70%, 80%, 90%, 95%, 96%, 97%, 98%, or 99% identical to the mature CTLA-4 protein sequence). Although genetically modified cells are also provided that can comprise the modifications described herein (e.g., ES cells, somatic cells), in many embodiments, the genetically modified non-human animals comprise the modification of the endogenous CTLA-4 locus in the germline of the animal.

Genetically modified animals can express a human CTLA-4 and/or a chimeric (e.g., humanized) CTLA-4 from endogenous mouse loci, wherein the endogenous mouse CTLA-4 gene has been replaced with a human CTLA-4 gene and/or a nucleotide sequence that encodes a region of human CTLA-4 sequence or an amino acid sequence that is at least 10%, 20%, 30%, 40%, 50%, 60%, 70&, 80%, 90%, 95%, 96%, 97%, 98%, or 99% identical to the human CTLA-4 sequence. In various embodiments, an endogenous non-human CTLA-4 locus is modified in whole or in part to comprise human nucleic acid sequence encoding at least one protein-coding sequence of a mature CTLA-4 protein.

In some embodiments, the genetically modified mice express the human CTLA-4 and/or chimeric CTLA-4 (e.g., humanized CTLA-4) from endogenous loci that are under control of mouse promoters and/or mouse regulatory elements. The replacement(s) at the endogenous mouse loci provide non-human animals that express human CTLA-4 or chimeric CTLA-4 (e.g., humanized CTLA-4) in appropriate cell types and in a manner that does not result in the potential pathologies observed in some other transgenic mice known in the art. The human CTLA-4 or the chimeric CTLA-4 (e.g., humanized CTLA-4) expressed in animal can maintain one or more functions of the wildtype mouse or human CTLA-4 in the animal. For example, human or non-human CD80 and/or CD86 can bind to the expressed CTLA-4 and downregulate immune response, e.g., downregulate immune response by at least 10%, 20%, 30%, 40%, or 50%. Furthermore, in some embodiments, the animal does not express endogenous CTLA-4. As used herein, the term "endogenous CTLA-4" refers to CTLA-4 protein that is expressed from an endogenous CTLA-4 nucleotide sequence of a non-human animal (e.g., mouse) without the genetic modification.

The genome of the animal can comprise a sequence encoding an amino acid sequence that is at least 70%, 75%, 80%, 85%, 90%, 95%, 99%, or 100% identical to human CTLA-4 (NP_005205.2) (SEQ ID NO: 37). In some embodiments, the genome comprises a sequence encoding an amino acid sequence that is at least 70%, 75%, 80%, 85%, 90%, 95%, 99%, or 100% identical to SEQ ID NO: 41.

The genome of the genetically modified animal can comprise a replacement at an endogenous CTLA-4 gene locus of a sequence encoding a region of endogenous CTLA-4 with a sequence encoding a corresponding region of human CTLA-4. In some embodiments, the sequence that is replaced is any sequence within the endogenous CTLA-4 gene locus, e.g., exon 1, exon 2, exon 3, exon 4, 5'-UTR, 3'UTR, the first intron, the second intron, and the third intron, etc. In some embodiments, the sequence that is replaced is within the regulatory region of the endogenous CTLA-4 gene. In some embodiments, the sequence that is replaced is exon 1, exon 2, exon 3, and/or exon 4 of an endogenous mouse CTLA-4 gene locus.

The genetically modified animal can have one or more cells expressing a human or chimeric CTLA-4 (e.g., humanized CTLA-4) having an extracellular region and a cytoplasmic region, wherein the extracellular region comprises a sequence that is at least 50%, 60%, 70%, 80%, 90%, 95%, 99% identical to the extracellular region of human CTLA-4. In some embodiments, the extracellular region of the humanized CTLA-4 has a sequence that has at least 10, 20, 30, 40, 50, 60, 70, 80, 90, or 100 amino acids (e.g., contiguously or non-contiguously) that are identical to human CTLA-4. Because human CTLA-4 and non-human CTLA-4 (e.g., mouse CTLA-4) sequences, in many cases, are different, antibodies that bind to human CTLA-4 will not necessarily have the same binding affinity with mouse CTLA-4 or have the same effects to mouse CTLA-4. Therefore, the genetically modified animal having a human or a humanized extracellular region can be used to better evaluate the effects of anti-human CTLA-4 antibodies in an animal model. In some embodiments, the genome of the genetically modified animal comprises a sequence encoding an amino acid sequence that corresponds to part or the entire sequence of exon 2 of human CTLA-4, part or the entire sequence of extracellular region of human CTLA-4 (with or without signal peptide), or part or the entire sequence of amino acids 42-145 of SEQ ID NO: 41.

In some embodiments, the non-human animal can have, at an endogenous CTLA-4 gene locus, a nucleotide sequence encoding a chimeric human/non-human CTLA-4 polypeptide, wherein a human portion of the chimeric human/non-human CTLA-4 polypeptide comprises a portion of human CTLA-4 extracellular domain, and wherein the animal expresses a functional CTLA-4 on a surface of a cell of the animal. The human portion of the chimeric human/non-human CTLA-4 polypeptide can comprise a portion of exon 2 of human CTLA-4. In some embodiments, the human portion of the chimeric human/non-human CTLA-4 polypeptide can comprise a sequence that is at least 80%, 85%, 90%, 95%, or 99% identical to amino acids 42-145 of SEQ ID NO: 41.

In some embodiments, the non-human portion of the chimeric human/non-human CTLA-4 polypeptide comprises transmembrane and/or cytoplasmic regions of an endogenous non-human CTLA-4 polypeptide. There may be several advantages that are associated with the transmembrane and/or cytoplasmic regions of an endogenous non-human CTLA-4 polypeptide. For example, once CD80 or CD86 binds to CTLA-4, they can properly transmit extracellular signals into the cells and regulate the downstream pathway. The intracellular domain of CTLA-4 is similar to that of CD28, in that it has no intrinsic catalytic activity and contains one YVKM motif able to bind PI3K, PP2A and SHP-2 and one proline-rich motif able to bind SH3 containing proteins. The first role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 can also bind PI3K. A human or humanized transmembrane and/or cytoplasmic regions may not function properly in non-human animal cells. In some embodiments, a few extracellular amino acids that are close to the transmembrane region of CTLA-4 are also derived from endogenous sequence.

Furthermore, the genetically modified animal can be heterozygous with respect to the replacement at the endogenous CTLA-4 locus, or homozygous with respect to the replacement at the endogenous CTLA-4 locus.

In some embodiments, the humanized CTLA-4 locus lacks a human CTLA-4 5'-UTR. In some embodiment, the humanized CTLA-4 locus comprises a rodent (e.g., mouse) 5'-UTR. In some embodiments, the humanization comprises a human 3'-UTR. In appropriate cases, it may be reasonable to presume that the mouse and human CTLA-4 genes appear to be similarly regulated based on the similarity of their 5'-flanking sequence. As shown in the present disclosure, humanized CTLA-4 mice that comprise a replacement at an endogenous mouse CTLA-4 locus, which retain mouse regulatory elements but comprise a humanization of CTLA-4 encoding sequence, do not exhibit pathologies. Both genetically modified mice that are heterozygous or homozygous for human CTLA-4 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CTLA-4 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human CTLA-4 in the genome of the animal.

Figure 2:
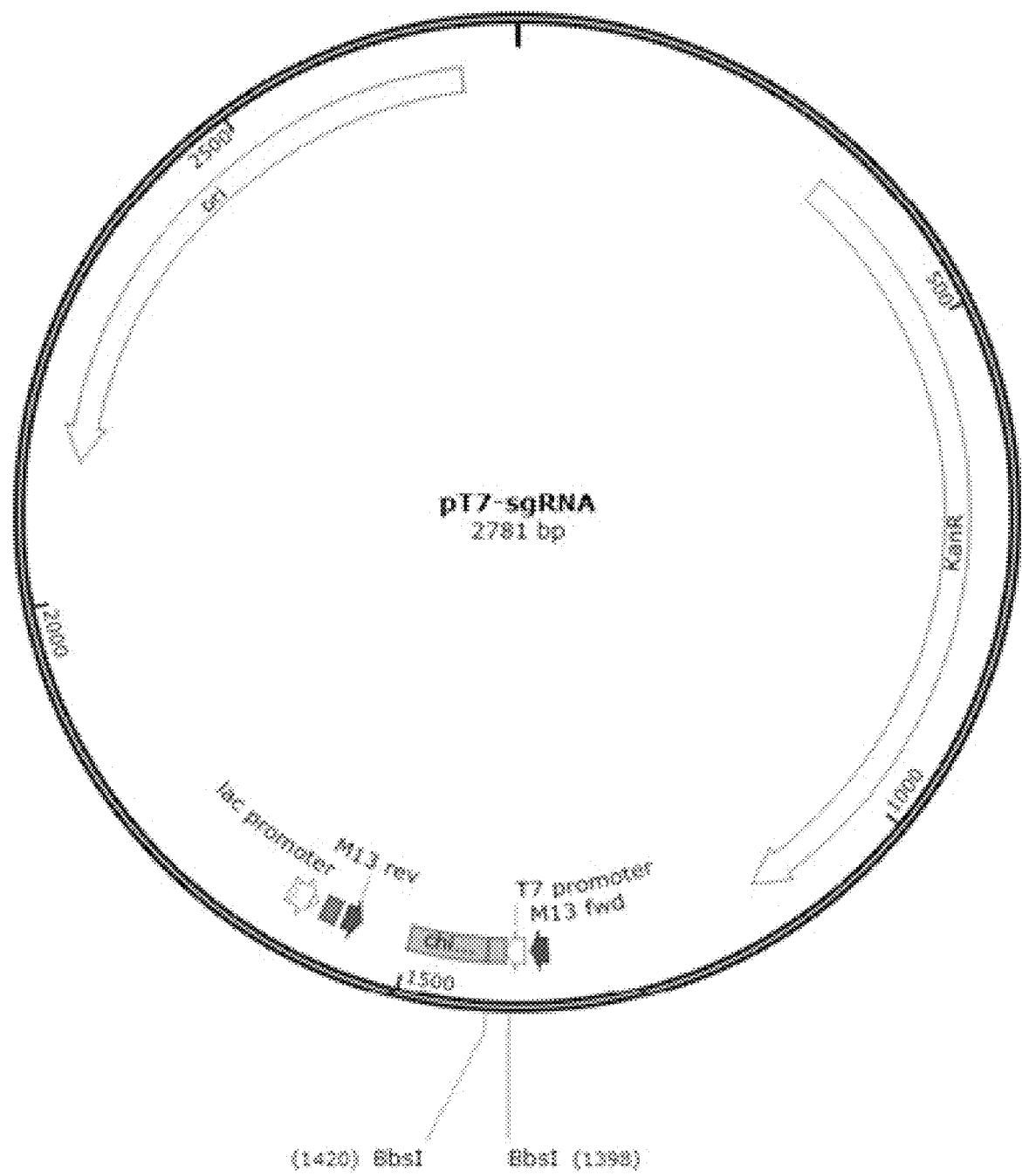
FIG. 2 is a schematic diagram showing pT7-sgRNA plasmid map.

In some embodiments, the non-human mammal comprises the genetic construct as shown in FIG. 2. In some embodiments, a non-human mammal expressing human CTLA-4 is provided. In some embodiments, the tissue-specific expression of human CTLA-4 protein is provided.

In some embodiments, the expression of human CTLA-4 in a genetically modified animal is controllable, as by the addition of a specific inducer or repressor sub stance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CTLA-4 protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human CTLA-4 protein.

Vectors

The present disclosure relates to a targeting vector, comprising: a) a DNA fragment homologous to the 5' end of a region to be altered (5' arm), which is selected from the CTLA-4 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CTLA-4 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000067.6; c) the DNA fragment homologous to the 3' end of the region to be altered (3' arm) is selected from the nucleotide sequences that have at least 90% homology to the NCBI accession number NC_000067.6.

In some embodiments, a) the DNA fragment homologous to the 5' end of a region to be altered (5' arm) is selected from the nucleotides from the position 60910913 to the position 60912430 of the NCBI accession number NC_000067.6; c) the DNA fragment homologous to the 3' end of the region to be altered (3' arm) is selected from the nucleotides from the position 60912743 to the position 60913715 of the NCBI accession number NC_000067.6.

In some embodiments, the length of the selected genomic nucleotide sequence in the targeting vector can be 1.5 kb and 1 kb.

In some embodiments, the region to be altered is exon 1, exon 2, exon 3, or exon 4 of CTLA-4 gene (e.g., exon 2 of CTLA-4 gene).

The targeting vector can further include a selected gene marker.

In some embodiments, the sequence of the 5' arm is shown in SEQ ID NO: 42; and the sequence of the 3' arm is shown in SEQ ID NO: 48.

In some embodiments, the target region is derived from human. For example, the target region in the targeting vector is a part or entirety of the nucleotide sequence of a human CTLA-4, preferably the nucleotide sequence is shown as a first exon, a second exon, a third exon, or a fourth exon of the DNA sequence of the human CTLA-4. In some embodiments, the nucleotide sequence of the humanized CTLA-4 encodes the humanized CTLA-4 protein with the NCBI accession number NP_005205.2. For example, the sequence of the target region can have the sequence as shown in SEQ ID NO: 48.

The disclosure also relates to a cell comprising the targeting vectors as described above.

Moreover, the disclosure also relates to an sgRNA sequence for constructing a humanized animal model, wherein the sgRNA sequence targets the CTLA-4 gene, the sgRNA is unique on the target sequence of the CTLA-4 gene to be altered, and meets the sequence arrangement rule of 5'-NNN (20)-NGG3' or 5'-CCN-N(20)-3'; and in some embodiments, the targeting site of the sgRNA in the mouse CTLA-4 gene is located on the exon 1, exon 2, exon 3, or exon 4 of the mouse CTLA-4 gene (e.g., exon 2 of the mouse CTLA-4 gene).

In some embodiments, an upstream sequence thereof is shown as SEQ ID NO: 25, and a downstream sequence thereof is shown as SEQ ID NO: 27, and the sgRNA sequence recognizes a 5' targeting site. In some embodiments, the forward oligonucleotide sequence is obtained by adding TAGG to the 5' end of SEQ ID NO: 25; and the reverse oligonucleotide sequence is obtained by adding AAAC to the 5' end of SEQ ID NO: 27.

In some embodiments, the disclosure provides an sgRNA sequence for constructing a humanized animal model, wherein an upstream sequence thereof is shown as SEQ ID NO: 29, and a downstream sequence thereof is shown as SEQ ID NO: 31, and the sgRNA sequence recognizes a 3' targeting site. In some embodiments, the forward oligonucleotide sequence is obtained by adding TAGG to the 5' end of SEQ ID NO: 29; and the reverse oligonucleotide sequence is obtained by adding AAAC to the 5' end of SEQ ID NO: 31.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin, Hao, Kevin J. Kauffman, and Daniel G. Anderson. "Delivery technologies for genome editing." Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CTLA-4 gene locus, a sequence encoding a region of an endogenous CTLA-4 with a sequence encoding a corresponding region of human or chimeric CTLA-4. In some embodiments, the replacement occurs in a germ cell, a somatic cell, a blastocyst, or a fibroblast, etc. The nucleus of a somatic cell or the fibroblast can be inserted into an enucleated oocyte.

Figure 5:
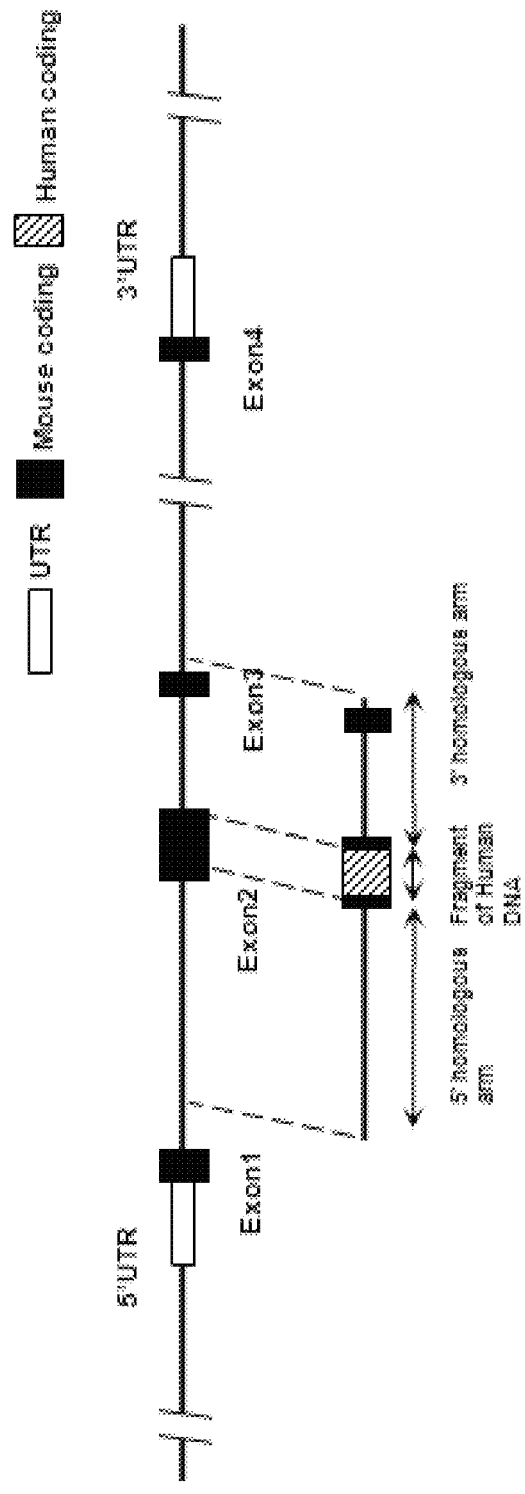
FIG. 5 is a schematic diagram showing mouse CTLA-4 gene targeting strategy.

FIG. 5 shows a humanization strategy for a mouse CTLA-4 locus. In FIG. 5, the targeting strategy involves a vector comprising the 5' end homologous arm, human CTLA-4 gene fragment, 3' homologous arm. The process can involve replacing endogenous CTLA-4 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CTLA-4 sequence with human CTLA-4 sequence.

Thus, in some embodiments, the methods for making a genetically modified, humanized animal, can include the step of replacing at an endogenous CTLA-4 locus (or site), a nucleic acid encoding a sequence encoding a region of endogenous CTLA-4 with a sequence encoding a corresponding region of human CTLA-4. The sequence can include a region (e.g., a part or the entire region) of exon 1, exon 2, exon 3, and/or exon 4 of a human CTLA-4 gene. In some embodiments, the sequence includes a region of exon 2 of a human CTLA-4 gene (e.g., amino acids 42-145 of SEQ ID NO: 41). In some embodiments, the region is located within the extracellular region of CTLA-4. In some embodiments, the endogenous CTLA-4 locus is Exon 2 of mouse CTLA-4.

In some embodiments, the methods of modifying a CTLA-4 locus of a mouse to express a chimeric human/mouse CTLA-4 peptide can include the steps of replacing at the endogenous mouse CTLA-4 locus a nucleotide sequence encoding a mouse CTLA-4 with a nucleotide sequence encoding a human CTLA-4, thereby generating a sequence encoding a chimeric human/mouse CTLA-4.

In some embodiments, the nucleotide sequence encoding the chimeric human/mouse CTLA-4 can include a first nucleotide sequence encoding an extracellular region of mouse CTLA-4 (with or without the mouse signal peptide sequence); a second nucleotide sequence encoding an extracellular region of human CTLA-4; a third nucleotide sequence encoding a transmembrane and a cytoplasmic region of a mouse CTLA-4.

In some embodiments, the nucleotide sequences as described herein do not overlap with each other (e.g., the first nucleic tide sequence, the second nucleotide sequence, and/or the third nucleotide sequence do not overlap). In some embodiments, the amino acid sequences as described herein do not overlap with each other.

The present disclosure further provides a method for establishing a CTLA-4 gene humanized animal model, comprising the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate and context of the humanized animal's physiology.

Genetically modified animals that express human or humanized CTLA-4 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized CTLA-4, which are useful for testing agents that can decrease or block the interaction between CTLA-4 and CD80 and/or the interaction between CTLA-4 and CD86, testing whether an agent can increase or decrease the immune response, and/or determining whether an agent is a CTLA-4 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CTLA-4 antibody for the treatment of cancer. The methods involving administering the anti-CTLA-4 antibody to the animal as described herein, wherein the animal has a tumor; and determining the inhibitory effects of the anti-CTLA-4 antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more tumor cells that express CD80 or CD86. In some embodiments, the tumor comprises one or more cancer cells (e.g., human or mouse cancer cells) that are injected into the animal.

In some embodiments, the genetically modified animals can be used for determining whether an anti-CTLA-4 antibody is a CTLA-4 agonist or antagonist. In some embodiments, the methods as described herein are also designed to determine the effects of the agent (e.g., anti-CTLA-4 antibodies) on CTLA-4, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer.

The inhibitory effects can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CTLA-4 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CTLA-4 antibody is designed for the treating melanoma, non-small cell lung carcinoma (NSCLC), small cell lung cancer (SCLC), bladder cancer, and/or prostate cancer (e.g., metastatic hormone-refractory prostate cancer). Anti-CTLA-4 antibodies are known in the art, and they include, e.g., ipilimumab (Yervoy) and tremelimumab, and some of them are described in, e.g., WO/2006/096491, WO/2012/120125A1, and WO/2016/196237A1, each of which is incorporated by reference in its entirety.

The present disclosure also relates to the use of the animal model generated through the method as described herein in the development of a product related to an immunization processes of human cells, the manufacturing of a human antibody, or the model system for a research in pharmacology, immunology, microbiology and medicine.

In some embodiments, the disclosure provides the use of the animal model generated through the method as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the method mentioned above in the screening, verifying, evaluating or studying the CTLA-4 gene function, human CTLA-4 antibodies, drugs for human CTLA-4 targeting sites, the drugs or efficacies for human CTLA-4 targeting sites, the drugs for immune-related diseases and antitumor drugs.

Genetically Modified Animal Model with Two or More Human or Chimeric Genes

The present disclosure further relates to methods for genetically modified animal model with two or more human or chimeric genes. The animal can comprise a human or chimeric CTLA-4 gene and a sequence encoding an additional human or chimeric protein.

In some embodiments, the additional human or chimeric protein can be programmed cell death protein 1 (PD-1), TNF Receptor Superfamily Member 4 (OX40), Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA).

The methods of generating genetically modified animal model with two or more human or chimeric genes (e.g., humanized genes) can include the following steps:

(a) using the methods of introducing human CTLA-4 gene or chimeric CTLA-4 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method the genetically modified animal can be mated with a genetically modified non-human animal with human or chimeric PD-1, OX40, LAG-3, TIM-3, PD-L1, 4-1BB, CD27, CD28, CD47, TIGIT, CD27, GITR, or BTLA.

In some embodiments, the CTLA-4 humanization is directly performed on a genetically modified animal having a human or chimeric PD-1, OX40, LAG-3, TIM-3, PD-L1, 4-1BB, CD27, CD28, CD47, TIGIT, CD27, GITR, or BTLA gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CTLA-4 antibody and an additional therapeutic agent for the treatment of cancer. The methods include administering the anti-CTLA-4 antibody and the additional therapeutic agent to the animal, wherein the animal has a tumor; and determining the inhibitory effects of the combined treatment to the tumor.

In some embodiments, the animal further comprises a sequence encoding a human or humanized programmed cell death protein 1 (PD-1). In some embodiments, the additional therapeutic agent is an anti-PD-1 antibody (e.g., nivolumab, pembrolizumab, avelumab, durvalumab, atezolizumab). In some embodiments, the tumor comprises one or more tumor cells that express CD80, CD86, PD-L1 or PD-L2.

In some embodiments, the combination treatment is designed for treating various cancer as described herein, e.g., melanoma, non-small cell lung carcinoma (NSCLC), small cell lung cancer (SCLC), bladder cancer, and/or prostate cancer (e.g., metastatic hormone-refractory prostate cancer).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

Ambion™ in vitro transcription kit was purchased from Ambion. Catalog number is AM1354.

E. coli TOP10 competent cells were purchased from the Tiangen Biotech (Beijing) Co. Catalog number is CB104-02.

HindIII, BamHI, XhoI, EcoRI, SmaI, BbsI, SspI, EcoNI were purchased from NEB. Catalog numbers are R3104M, R3136M, R0146M, R3101M, R0141S, R0539L, R3132M, R3101M.

Kanamycin was purchased from Amresco. Catalog number is 0408.

Cas9 mRNA was obtained from SIGMA. Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

C57BL/6 mice were purchased from the China Food and Drugs Research Institute National Rodent Experimental Animal Center.

Reverse Transcription Kit was obtained from TakaRa. Catalog number is 6110A.

Mouse colon cancer cell line MC38 was purchased from Shanghai Enzyme Research Biotechnology Co., Ltd.

Mouse CD3 antibody was obtained from BD. Catalog number is 563123.

mTcRβ PerCP was obtained from Biolegend. Catalog number is 109228.

mPD-1_PE was obtained from Biolegend. Catalog number is 109104.

mCTLA-4 APC was obtained from Biolegend. Catalog number is 106310.

hCTLA-4 PE was obtained from Biolegend. Catalog number is 349906.

hPD-1 FITC was obtained from Biolegend. Catalog number is 329904.

Example 1: Construction of PT7-C-7 and pT7-C-18

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA12) and the 3'-terminal targeting sites (sgRNA13 to sgRNA24) were designed and synthesized. Both the 5'-terminal targeting sites and the 3'-terminal targeting sites are located on exon 2 of mouse Ctla-4 gene, and the targeting site sequence on Ctla-4 of each sgRNA is as follows:

```
sgRNA-1 targeting sequence (SEQ ID NO: 1):
5'-ggtcacctgtatggctgacatgg-3' sgRNA-2 targeting sequence (SEQ ID NO: 2):
5'-tgaaggttgggtcacctgtatgg-3' sgRNA-3 targeting sequence (SEQ ID NO: 3):
5'-acaggtgacccaaccttcagtgg-3' sgRNA-4 targeting sequence (SEQ ID NO: 4):
5'-gacccaaccttcagtggtgttgg-3' sgRNA-5 targeting sequence (SEQ ID NO: 5):
5'-agccaacaccactgaaggttggg-3' sgRNA-6 targeting sequence (SEQ ID NO: 6):
5'-ctgctagccaacaccactgaagg-3' sgRNA-7 targeting sequence (SEQ ID NO: 7):
5'-gtggtgttggctagcagccatgg-3' sgRNA-8 targeting sequence (SEQ ID NO: 8):
5'-atggaaagctggcgacaccatgg-3' sgRNA-9 targeting sequence (SEQ ID NO: 9):
5'-tgtgatggtgaatattcacatgg-3' sgRNA-10 targeting sequence (SEQ ID NO: 10):
5'-accatcacacaacactgatgagg-3' sgRNA-11 targeting sequence (SEQ ID NO: 11):
5'-acctcatcagtgttgtgtgatgg-3' sgRNA-12 targeting sequence (SEQ ID NO: 12):
5'-acacaacactgatgaggtccggg-3' sgRNA-13 targeting sequence (SEQ ID NO: 13):
5'-aggtccgggtgactgtgctgcgg-3' sgRNA-14 targeting sequence (SEQ ID NO: 14):
5'-tctgccgcagcacagtcacccgg-3' sgRNA-15 targeting sequence (SEQ ID NO: 15):
5'-tggcacagacctcagtcatttgg-3' sgRNA-16 targeting sequence (SEQ ID NO: 16):
5'-actttgtgggcatgggcaacggg-3' sgRNA-17 targeting sequence (SEQ ID NO: 17):
5'-ttgcccatgcccacaaagtatgg-3' sgRNA-18 targeting sequence (SEQ ID NO: 18):
5'-ccgccatactttgtgggcatggg-3' sgRNA-19 targeting sequence (SEQ ID NO: 19):
5'-atgcccacaaagtatggcggtgg-3' sgRNA-20 targeting sequence (SEQ ID NO: 20):
5'-tacccaccgccatactttgtggg-3' sgRNA-21 targeting sequence (SEQ ID NO: 21):
5'-ggactgagagctgttgacacggg-3' sgRNA-22 targeting sequence (SEQ ID NO: 22):
5'-tgtcaacagctctcagtccttgg-3' sgRNA-23 targeting sequence (SEQ ID NO: 23):
5'-gttcactctgctttcattaaagg-3' sgRNA-24 targeting sequence (SEQ ID NO: 24):
5'-attaaaggtaccactgcagaagg-3'
```

Figure 1A:
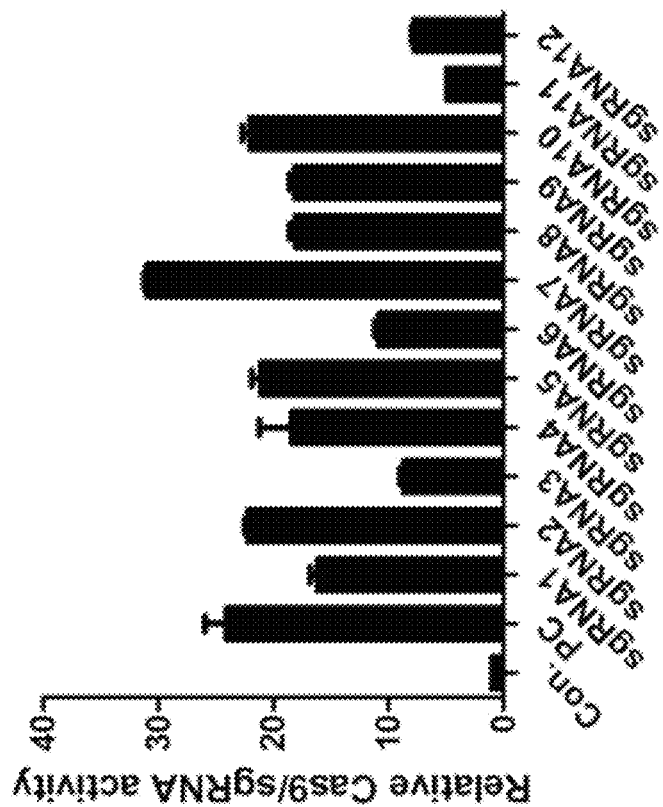
FIG. 1A is a graph showing the 5' terminal target site sgRNA activity test results (sgRNA1-sgRNA12)(Con is a negative control; and PC is a positive control).

The UCA kit was used to detect the activities of sgRNAs (FIGS. 1A and 1B). The results show that the guide sgRNAs have different activities. Two of them (sgRNA7 and sgRNA18, respectively) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-C-7 and pT7-C-18.

TABLE 3

| pT7-C-7 and pT7-C-18 sequences | |
|---|---|
| sgRNA7 sequences | |
| SEQ ID NO: 25 | Upstream:<br>5'-TGTTGGCTAGCAGCCA-3' |
| SEQ ID NO: 26<br>(adding TAGG to obtain a forward oligonucleotide sequence) | Upstream:<br>5'-TAGGTGTTGGCTAGCAGCCA-3' |
| SEQ ID NO: 27 | Downstream:<br>5'-TGGCTGCTAGCCAACA-3' |
| SEQ ID NO: 28<br>(complementary strand was added with AAAC to obtain a reverse oligonucleotide sequence) | Downstream:<br>5'-AAACTGGCTGCTAGCCAACA-3' |
| sgRNA18 | |
| SEQ ID NO: 29 | Upstream:<br>5'-CCATACTTTGTGGGCAT-3' |
| SEQ ID NO: 30<br>(adding TAGG to obtain a forward oligonucleotide sequence) | Upstream:<br>5'-TAGGCCATACTTTGTGGGCAT-3' |
| SEQ ID NO: 31 | Downstream:<br>5'-ATGCCCACAAAGTATGG-3' |
| SEQ ID NO: 32<br>(complementary strand was added with AAAC to obtain a reverse oligonucleotide sequence) | Downstream:<br>5'-AAACATGCCCACAAAGTATGG-3' |

TABLE 3-continued pT7-C-7 and pT7-C-18 sequences

The DNA fragment containing the T7
promoter and sgRNA scaffold (SEQ ID NO: 33):
GAATTCTAATACGACTCACTATAGGGGGTCTTCGAGAAGACCTGTTTTAG
AGCTAGAAATAGCAAGTTAAAATAAGGCTAGTCCGTTATCAACTTGAAAA
AGTGGCACCGAGTCGGTGCTTTTAAAGGATCC

TABLE 4

The ligation reaction conditions

| Double stranded fragment | 1 μL (0.5 μM) |
| pT7-sgRNA vector | 1 μL (10 ng) |
| T4 DNA Ligase | 1 μL (5U) |
| 10x T4 DNA Ligase buffer | 1 μL |
| 50% PEG4000 | 1 μL |
| H$_2$O | Add to 10 μL |

Reaction Conditions:

The ligation reaction was carried out at room temperature for 10 to 30 min. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-C-7 and pT7-C-18 were selected for subsequent experiments.

Source of pT7-sgRNA Plasmid

PT7-sgRNA vector map is shown in FIG. 2. The plasmid backbone was obtained from Takara (Catalog No. 3299). The DNA fragment containing T7 promoter and sgRNA scaffold was synthesized by a plasmid synthesis company, and linked to the backbone vector by restriction enzyme digestion (EcoRI and BamHI) and ligation. The target plasmid was confirmed by the sequencing results.

Example 2. Construction of Vector pClon-4G-CTLA-4

Figure 4:
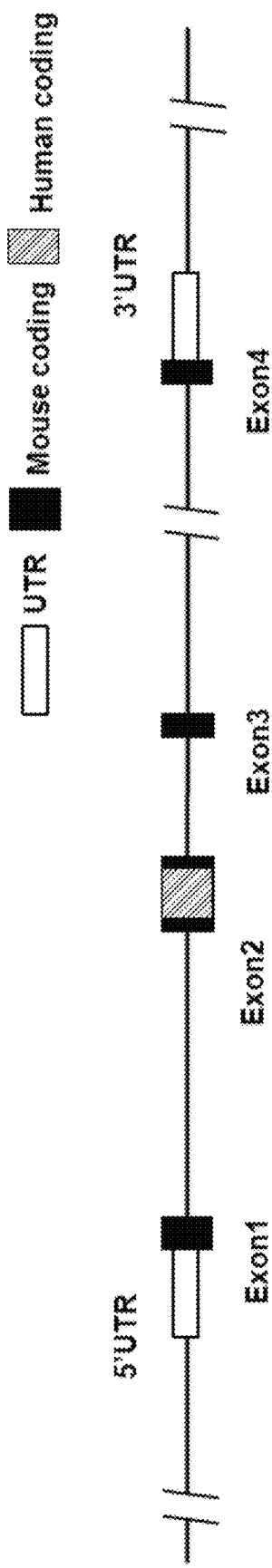
FIG. 4 is a schematic diagram showing humanized CTLA-4 mouse gene map.

A partial coding sequence of the mouse Ctla 4 gene (Gene ID: 12477) exon 2 (based on the transcript of NCBI accession number NM_009843.4→NP_033973.2, whose mRNA sequence is shown in SEQ ID NO: 34, and the corresponding protein sequence is shown in SEQ ID NO: 35) was replaced with a corresponding coding sequence of human homologous CTLA-4 gene (Gene ID: 1493) (based on the transcript of NCBI accession number NM_005214.4→NP_005205.2, whose mRNA sequence was shown in SEQ ID NO: 36, and the corresponding protein sequence is shown in SEQ ID NO: 37). The comparison between the mouse Ctla 4 and human CTLA-4 is shown in FIG. 3, and the finally obtained humanized CTLA-4 gene is shown in FIG. 4, the humanized mouse CTLA-4 gene DNA sequence (chimeric CTLA-4 gene DNA) is shown in SEQ ID NO: 38 (shown immediately below).

ccatgtcagccatacag*gtggcccagcctgagtggtactggccagcagcc*

*gaggcatcgccagctttgtgtgtgagtatgcatctccaggcaaagccact*

*gaggtccgggtgacagtgcttcggcaggctgacagccaggtgactgaagt*

*ctgtgcggcaacctacatgatggggaatgagttgaccttcctagatgatt*

*ccatctgcacgggcacctccagtggaaatcaagtgaacctcactatccaa*

*ggactgagggccatggacacgggactctacatctgcaaggtggagctcat*

*gtacccaccgccatactacctgggcata*ggcaacgggacgcagatttatg tcattggtga

SEQ ID NO: 38 lists only the portion of DNA sequence involved in the modification, wherein the italicized underlined region is the human CTLA-4 gene sequence fragment.

The coding region sequence, mRNA sequence and the encoded protein sequence thereof of the chimeric CTLA-4 (containing a portion of human CTLA-4 sequence) are respectively shown in SEQ ID NO: 39, SEQ ID NO: 40 and SEQ ID NO: 41.

A targeting strategy involving a vector comprising the 5' end homologous arm, human CTLA-4 gene fragment, 3' homologous arm as shown in FIG. 5 is also developed. The process is as follows:

(1). Design upstream primers of homologous recombination fragments, and downstream primers matching therewith, as well as other related sequences. Specifically:

5' end homologous arm (SEQ ID NO: 42), nucleotide sequence of the positions from 60/910,913 to 60/912,430 of the NCBI accession number NC_000067.6 as follows:

atgagcaaagggtgcttgcagaaagtctctgatagtagagatgaaggcta ggcagacacctgctgtttcacccgctaagctgatggagtaaccatggcaa ctgccaccatattgttctcttttctgaggacagatgctaatcagtacagg tgctttcagaagagactagggtatctatatagcctggtttatggatagga gaggtggtcttggaaactaagcctgggggtagtattcaagattgcaataca ctgaaaactaattattgtcttgttttacaatctatgttagtaaactacc aatgacattgttcagtttaagttttgggtgtaatcttcaatactgaccgg aaaacatccaggttagttatgaaaaggcaatatgacagaaagccacttt gtgtgctgagagtacaacccgagatcgtgtgtattctaggcaagcactct accaccgacctacatctccagcccttctgcctgtggttctttgtcttgta aagcaatgtcttgttgtttagctgatgctggccttgcacttgctatgtag ccttcatctgctggctgctaggactgcagatttgtaccaccaataccgga ctgcaaacccactaatttctaatgatgaaggcatgtttgtatagagagct ggactcctttcttctgtagtatacagggaggaaagagaaaacaacaaaaa cagcagcagcagcagcagcaacaacaacaacaacaaaaaccccaaggaca aggaaagtgttaagtgaaggaaagaagggaggcagaagaggtggcaggga agcaggggaagcccacagaagttaaagcagggttgtctcaacccagagag gaaatgaccctggtgccctcagctctgtggcttccttgactgatgtatac accactctaccacagtgatgccaggaaaagggtgaccaatgcattgacct gaggttcaactgctcctggttgacagaggtacgcttataaataagtaggt aggaaaattttgaagcttactttgagagatgaggcaaggttctgcacctc aagctccaggaatgtctcgactgccattcactatgtttcctgcgtgatat

```
agttctattatcaccaaagaaggcgctgtactgacatgtaggctacccc ttttcttactgcaggggagaataaatgaaaggaagaattatttgccaaaa tgacacattttatgagagccagatcttcttttttgctataccagtattctc cttgccatagccaactgtcttcaataaactatcaataaggggatcttgga gagtgactgactacagctgaaagatgggaagtggagtgccagggtggatg ggtggagaggcaaagggtgaagggagtgatgagtttgttgagggtgagc ttgcaggagttcatccaagatgaacctcccctggcctcaggtgtggccta atagttcaaaccgtggatgatcatgagcccactaagtgccctttggactt tccatgtcagccatacag Upstream primer (F):
                                          (SEQ ID NO: 43)
5'-TTTAAGAAGGAGATATACATGCTCGAGATGAGCAAAGGGTGCTTGCA

GAAAGTC-3'

Downstream primer (R):
                                          (SEQ ID NO: 44)
5'-ACCACAGCAGGCTGGGCCACCTGTATGGCTGACATGGAAAGTCCA-
3'
```

(2). Design the primers and related sequences of the target conversion region. The total length of the human DNA fragment was 312 bp, which was the nucleotide sequence from positions 203870594 to 203870905 of the NCBI accession number NC_000002.12:

```
                                          (SEQ ID NO: 45)
gtggcccagcctgctgtggtactggccagcagccgaggcatcgccagctt tgtgtgtgagtatgcatctccaggcaaagccactgaggtccgggtgacag tgcttcggcaggctgacagccaggtgactgaagtctgtgcggcaacctac atgatggggaatgagttgaccttcctagatgattccatctgcacgggcac ctccagtggaaatcaagtgaacctcactatccaaggactgagggccatgg acacgggactctacatctgcaaggtggagctcatgtacccaccgccatac tacctgggcata The amplification primers are:
F:
                                          (SEQ ID NO: 46)
5'-TGGACTTTCCATGTCAGCCATACAGGTGGCCCAGCCTGCTGTGG-3'

R:
                                          (SEQ ID NO: 47)
5'-TAAATCTGCGTCCCGTTGCCTATGCCCAGGTAGTATGGCGG-3'
```

(3). Design the upstream primers of the homologous recombination fragment and the downstream primers matching therewith, as well as other related sequences. Specifically:

3' homologous arm (SEQ ID NO: 48), which was the nucleotide sequence from positions 60912743 to 60/913,715 of the NCBI accession number NC_000067:

```
ggcaacgggacgcagatttatgtcattggtgagcaaagccattccactaa gaacaagtctgttgcattattattgtctttacaccagaatagttttgttc cttggtttggagtccttcatagttaggtctgtgatgcatagctaggaatt ccctagtagatagtagtcttgcttatactgagaagttacataaccatcac
```

```
tctgattgcaatgaaacgcatttggggatgtgttttttatactgcttgct gatagtctaggacacttgttcttgaagtttagtcttgtcccttttgatggc actctgggaaagtcatgtattaaataagtagccagacttccctatagttt accaatacaagttagggttgactagcaaaacctggaacctctaacttcct tttactacccatgaggaactaggacccacaattggaaactctctcagga ggttgatgcttcgtcttctgttgcagatccagaaccatgcccggattctg acttcctcctttggatccttgtcgcagttagcttggggttgttttttac agtttcctggtcactgctgtttctttgagcaagatggtgagtgtgatgtt gacgtttccccacagttaatggggatacttttagttgtaccctactgacc aattggtgttgagttgaagcaataaacaaggagcaggaaggatagggtaa agaacacgctagaacccatgcacttgccttagaggtttcgggatgacta atactgtacgtgagcatgtttgacagtgaatgtttgtgtgcttctgagca gggtttcagtttgagtaactgtttgaacaacatggagcagctgttttggt tgtcactgtcatggcaatgtccttaatcctaggacacacagcagtctctg ggcaaccctttctagttagaaccacctagatggattttttgtccttttacca agcaccatctcttggtccctctt Upstream primer:
F:
                                          (SEQ ID NO: 49)
5'-CGCCATACTACCTGGGCATAGGCAACGGGACGCAGATTTATG-3'

Downstream primer:
R:
                                          (SEQ ID NO: 50)
5'-TTGTTAGCAGCCGGATCTCAGGCGGCCGCAAGAGGGACCAAGAGATG
GTGCT-3'
```

C57BL/6 mouse DNA is used as the template to carry out PCR amplification for the 5'-terminal homologous arm fragment (SEQ ID NO: 42) and the 3'-terminal homologous arm fragment (SEQ ID NO: 48) of exon 2. Human DNA is used as the template to carry out PCR amplification for the DNA fragment (SEQ ID NO: 45), and the AIO kit is used to ligate the fragments to the pClon-4G plasmid provided by the kit, so as to obtain the vector pClon-4G-CTLA-4.

Example 3. Verification of Vector pClon-4G-CTLA-4

Figure 6:
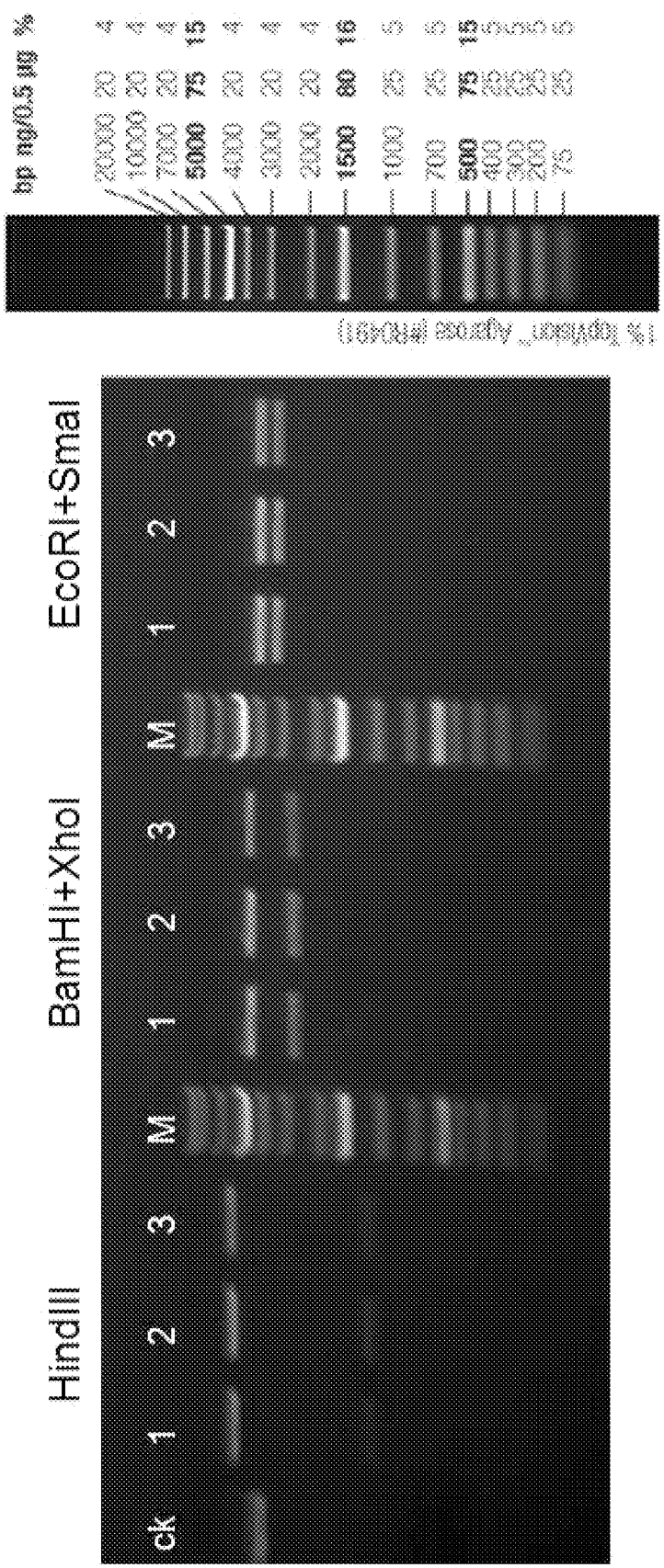
FIG. 6 shows pClon-4G-CTLA-4 plasmid digestion result (M is the Marker, ck is the undigested plasmid control).

Three pClon-4G-CTLA-4 clones were randomly selected and identified by three sets of enzymes. Among them, HindIII should generate 1070 bp+5250 bp fragments, BamHI+XhoI should generate 2348 bp+3972 bp fragments, EcoRI+SmaI should generate 2818 bp+3502 bp fragments. The results obtained were in line with the expectations (FIG. 6). The sequences of Plasmids 1 and 2 were verified by sequencing. Plasmid 1 was selected for subsequent experiments.

Example 4. Microinjection and Embryo Transfer

The pre-mixed in vitro transcription products of Cas9 mRNA, pClon-4G-CTLA-4 plasmid and pT7-C-7, pT7-C-18 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice. The mice population was further expanded by cross-mating and self-mating to establish stable mouse lines. The humanized mouse obtained was named B-hCTLA-4.

Example 5. Identification of Genetically Modified Humanized Mouse Model

1. Genotype Detection

PCR analysis was performed for mouse tail genomic DNA using 7 F0 generation mice. Primers was designed for exon 2 of CTLA-4 gene; the primers for PCR-1 were located on the left side of the 5' homologous arm, the primers for PCR-4 were located on the right side of the 3' homologous arm; in addition, the primers for PCR-2 and PCR-3 were located on the humanized fragment, which are shown below:

```
5' terminus primers:
PCR-1:
                                          (SEQ ID NO: 51)
5'-GAAAGGCTAATACCAGGCTTGTTATGTGC-3'

PCR-2:
                                          (SEQ ID NO: 52)
5'-TCAACTCATTCCCCATCATGTAGGTTGC-3'

3' terminus primers:
PCR-3:
                                          (SEQ ID NO: 53)
5'-GAGTATGCATCTCCAGGCAAAGCCA-3'

PCR-4:
                                          (SEQ ID NO: 54)
5'-CACTGAGCTAGGGAGGGCATCAAGG-3'
```

If the recombinant vector has the correct insertion, there should be only one PCR band. The length of the 5' terminus product should be 1924 bp, and the length of the 3' terminus product should be 1325 bp.

TABLE 5

| The PCR reaction system (20 μL) | |
|---|---|
| 10x buffer | 2 μL |
| dNTP (2 mM) | 2 μL |
| MgSO₄ (25 mM) | 0.8 μL |
| Upstream primer (10 μM) | 0.6 μL |
| Downstream primer (10 μM) | 0.6 μL |
| C57BL/6 gDNA | 200 ng |
| KOD-Plus-(1 U/μL) | 0.6 μL |

TABLE 6

| The PCR reaction conditions | | |
|---|---|---|
| Temperature | Time | Cycles |
| 94° C. | 5 min | 1 |
| 94° C. | 30 sec | 15 |
| 67° C.* | 30 sec | |
| 68° C. | 1 kb/min | |
| 94° C. | 30 sec | 25 |
| 56° C. | 30 sec | |
| 68° C. | 1 kb/min | |

TABLE 6-continued

| The PCR reaction conditions | | |
|---|---|---|
| Temperature | Time | Cycles |
| 68° C. | 10 min | 1 |
| 4° C. | 10 min | 1 |

(*each cycle has a temperature drop of 0.7° C.)

Figures 7A, 7B:
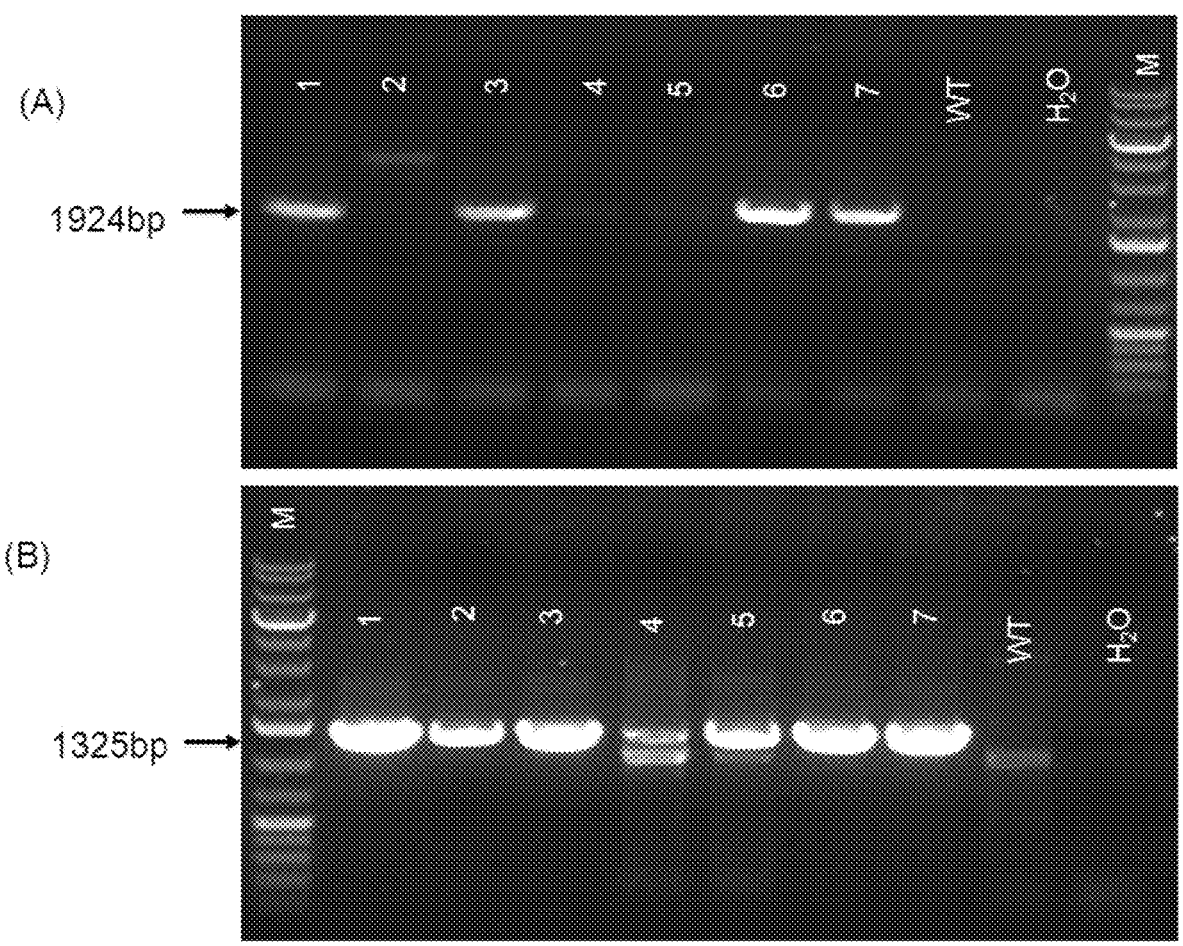
FIG. 7A shows PCR identification result (5' terminus) of samples from mouse tails (WT is wild type, M is Marker, no. 1, 3, 6 and 7 are positive mice).
FIG. 7B shows mouse tail PCR identification result (3' terminus) (WT is wild type, M is Marker).

Among the 4 mice, 5 of them were identified as positive mice. The identification results of the 4 mice are provided in FIG. 7.

Figures 8A, 8B:
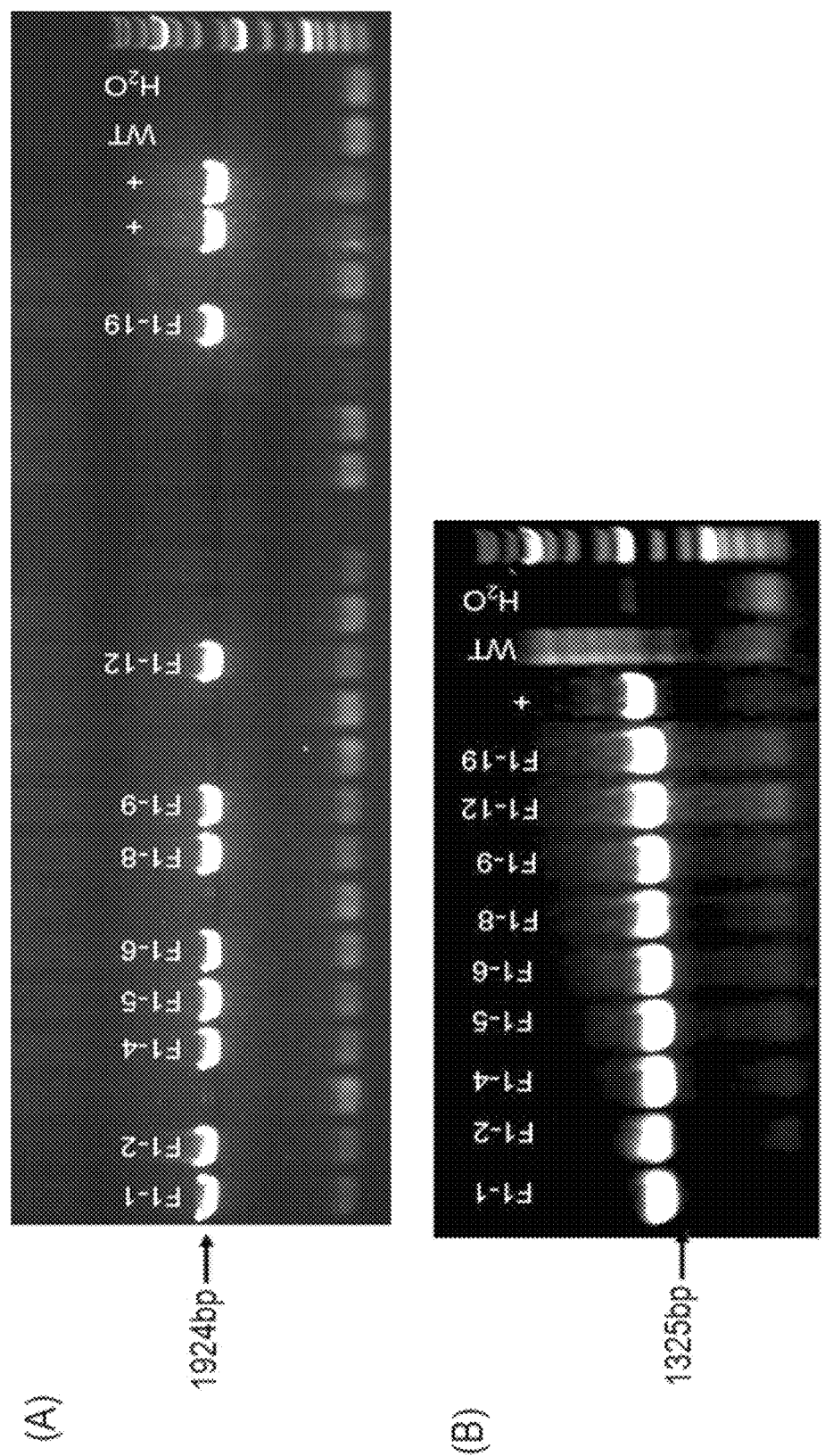
FIGS. 8A and 8B show mouse tail PCR identification result (WT is wild type, M is Marker, F1-1, F1-2, F1-4, F1-5, F1-6, F1-8, F1-9, F1-12, F1-19 are the F1 generation B-hCTLA-4 positive mice).

Furthermore, F1 generation mice were obtained by mating the F0 mice with wild type mice. PCR analysis was then performed on genomic DNA of F1 mice tails. PCR conditions and primers are the same with those used for F0 genotype detection. The results of PCR for F1 mice were shown in FIG. 8, indicating that there were 9 positive F1 mice, and these mice are as follows: F1-1, F1-2, F1-4, F1-5, F1-6, F1-8, F1-9, F1-12, and F1-19.

Nine mice (F1-1, F1-2, F1-4, F1-5, F1-6, F1-8, F1-9, F1-12, and F1-19) that were confirmed by PCR were further examined by Southern blotting to determine whether they had a random insertion. The genomic DNA was extracted from the mouse tail, and SspI and EcoNI were used to digest the genomic DNA, the digestion products were transferred to membrane and hybridized. The probes P1 and P2 were located respectively on the outside of the 5' homologous arm and the humanized fragment. The primers for probe synthesis are as follows:

```
P1-F (SEQ ID NO: 55):
5'-tgtgttaaagcaacacagcgtggtc-3'

P1-R (SEQ ID NO: 56):
5'-aactgttgttgccgtttggtccttg-3'

P2-F (SEQ ID NO: 57):
5'-agaagaccattgcttttggctgttt-3'

P2-R (SEQ ID NO: 58):
5'-acatggaaaagtgcagaactaaaga-3'
```

The genetically engineered mice should have the 5.4 kb or 12.6 kb band with probe hybridization; whereas the wild type C56BL/6 mice would have the 3.6 kb or 6.1 kb band, and no hybrid band should be generated.

Figure 9:
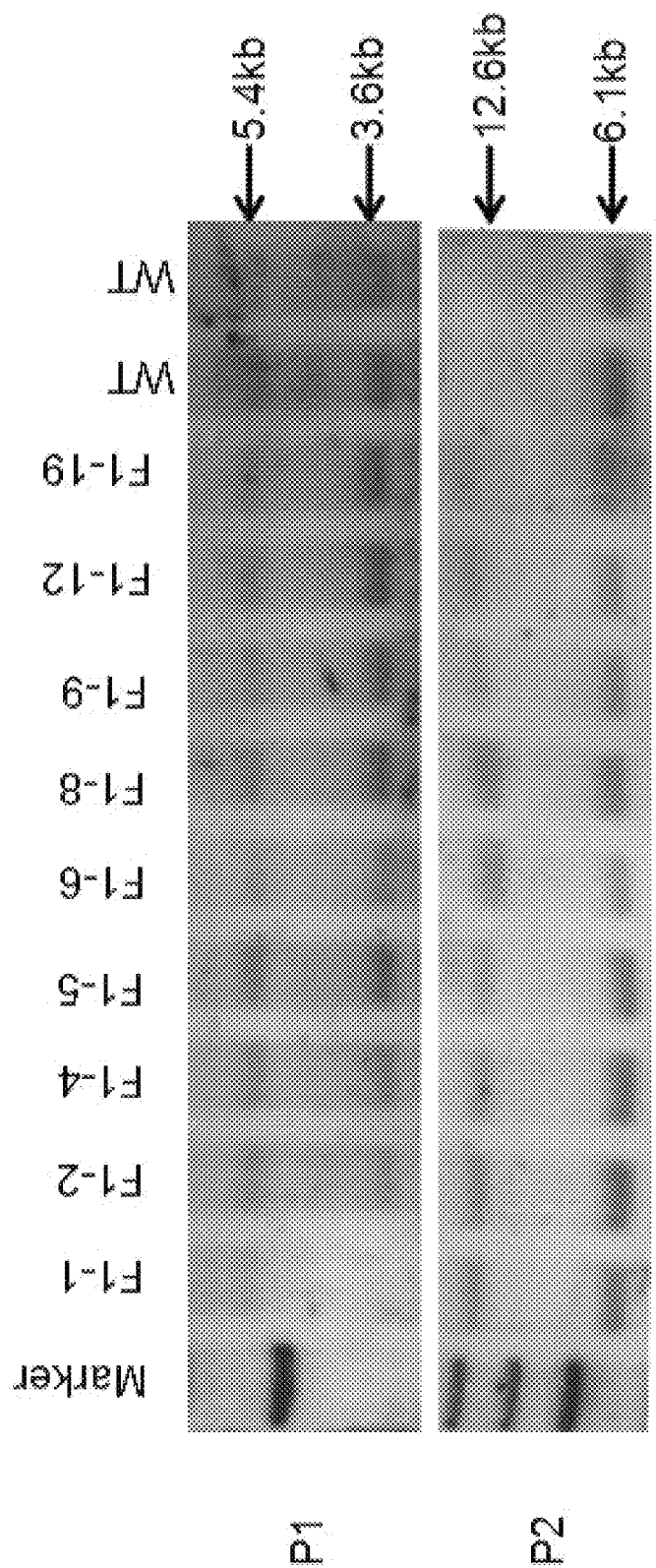
FIG. 9 shows F1 generation mice Southern blot results (WT is wild type, F1-1, F1-2, F1-4, F1-5, F1-6, F1-8, F1-9, F1-12, F1-19 mice have no random insertion).

The results showed that the bands were consistent with the expected results. It was confirmed that the 9 mice were positive hybrids that did not have random insertions. The mice included F1-1, F1-2, F1-4, F1-5, F1-6, F1-8, F1-9, F1-12 and F1-19. Southern blot results are shown in FIG. 9.

It thus shows that this method can be used to construct B-hCTLA-4 humanized genetically engineered mice that have no random insertion.

2. Protein Identification

Figure 10:
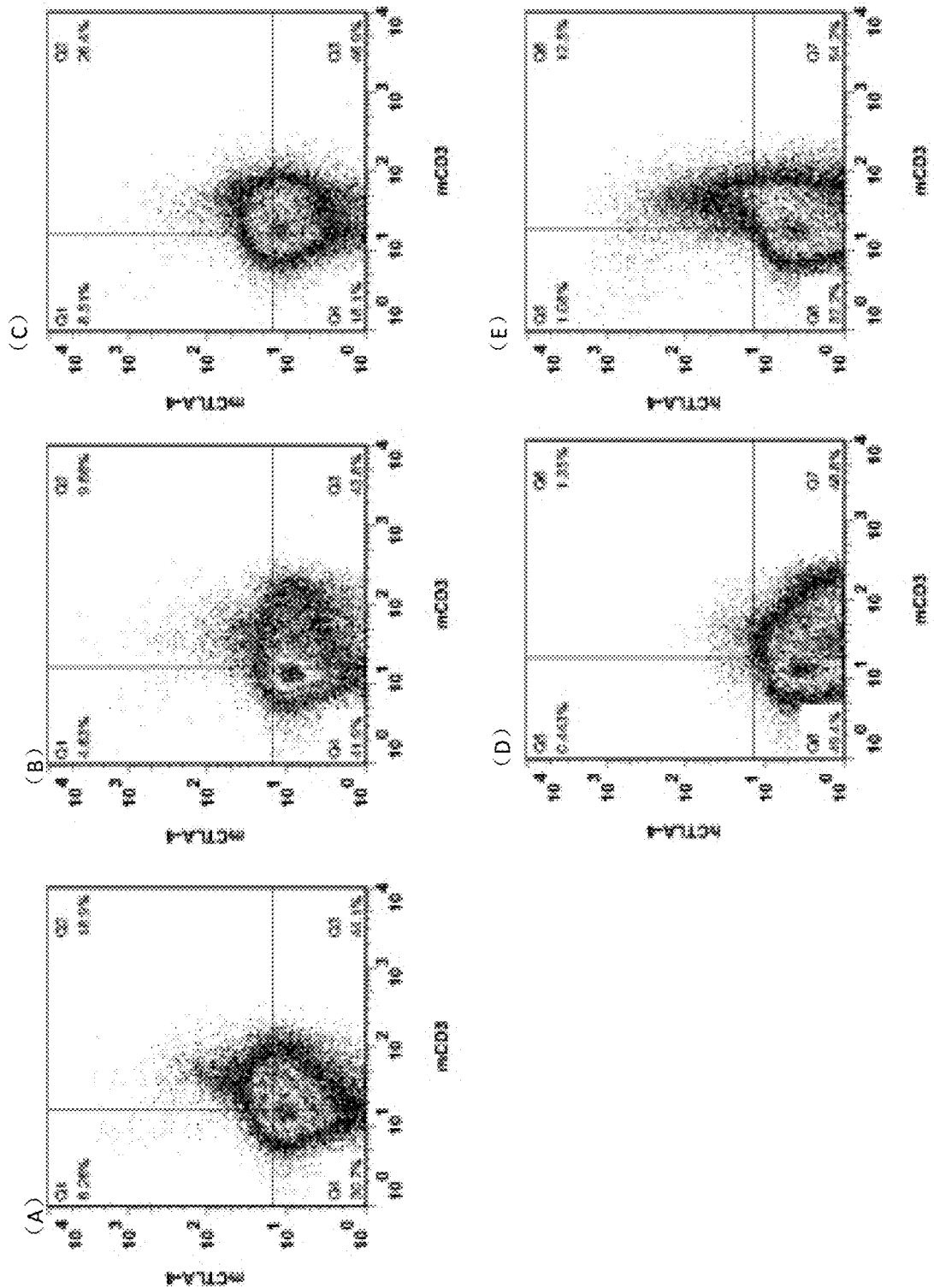
FIG. 10 shows flow cytometry analysis results for C57BL/6 mice and CTLA-4 humanized mice. Anti-mouse CD3 antibody was used to stimulate their T cell activation in the spleen, and then anti-mouse (FIGS. 10B and 10C) and anti-human (FIGS. 10D and 10E) CTLA-4 fluorescent antibodies were used for cell labeling, which were then detected in the flow cytometry analysis. Compared with the control group, the cells with the expression of human CTLA-4 protein can be detected in the spleen of CTLA-4 humanized F1 hybrids; whereas in the spleen of C57BL/6 mice, no cells expressing human CTLA-4 protein were detected.

One of the humanized F0 generation mice identified by PCR was selected for the study. One wild type C57BL/6 mouse was used as the control. 15 μg of CD3 were injected intraperitoneally to the mice, and in 24 h 15 μg of CD3 were further injected intraperitoneally to the mice. The spleens were collected at the end of 39 h, and the spleen samples were grinded. The ground samples were then passed through 70 μm cell mesh, the filtered cell suspensions were centrifuged and the supernatants were discarded; the erythrocyte lysis solution was added for lysis of 5 min, and then PBS solution was added to neutralize the lysis reaction. The solution was centrifuged again and the supernatants were discarded. The cells were washed once with PBS. The antibody staining was performed for 30 to 45 min in darkness; and the cells were washed once again with PBS. Flow cytometry was carried out to detect protein expression. Flow cytometry analysis results (FIG. 10) show when compared with the C57BL/6 mice with or without the stimulation of CD3 antibody for T cell activation in spleen, the humanized mouse spleen has the cells of human CTLA-4 protein expression as detected by anti-human CTLA-4 antibody, while the spleen of the C57BL/6 control mice does not have detectable cells of human CTLA-4 protein expression. The foregoing results indicate that the CTLA-4 genetically modified humanized mouse is able to express human CTLA-4 protein, which can be detected by an anti-human antibody. The model mice will be useful for screening and detection of anti-human CTLA-4 antibodies.

The B-hCTLA-4 humanized genetically engineered homozygous mice were obtained by mating the previously obtained F1 positive mice with each other. Two B-hCTLA-4 mice (one homozygote, one heterozygote, 3-8 weeks old) were selected, and one wild type C57BL/6 mouse was selected as a control. 7.5 µg of mouse CD3 antibody was injected intraperitoneally to the mice, and the spleens of the mice were collected after 28 h. The spleen samples were ground and then filtered through a 70 µm cell filter, the obtained cell suspensions were centrifuged and the resulting supernatants were discarded. The cell samples were added with erythrocyte lysis solution for lysis of 5 min, and then added PBS solution to neutralize the lysis reaction, centrifuged again and the supernatants were discarded, the cells were washed once with PBS. The obtained samples were used in FACS detection and RT-PCR detection.

Figures 11A, 11B, 11C, 11D, 11E, 11F:
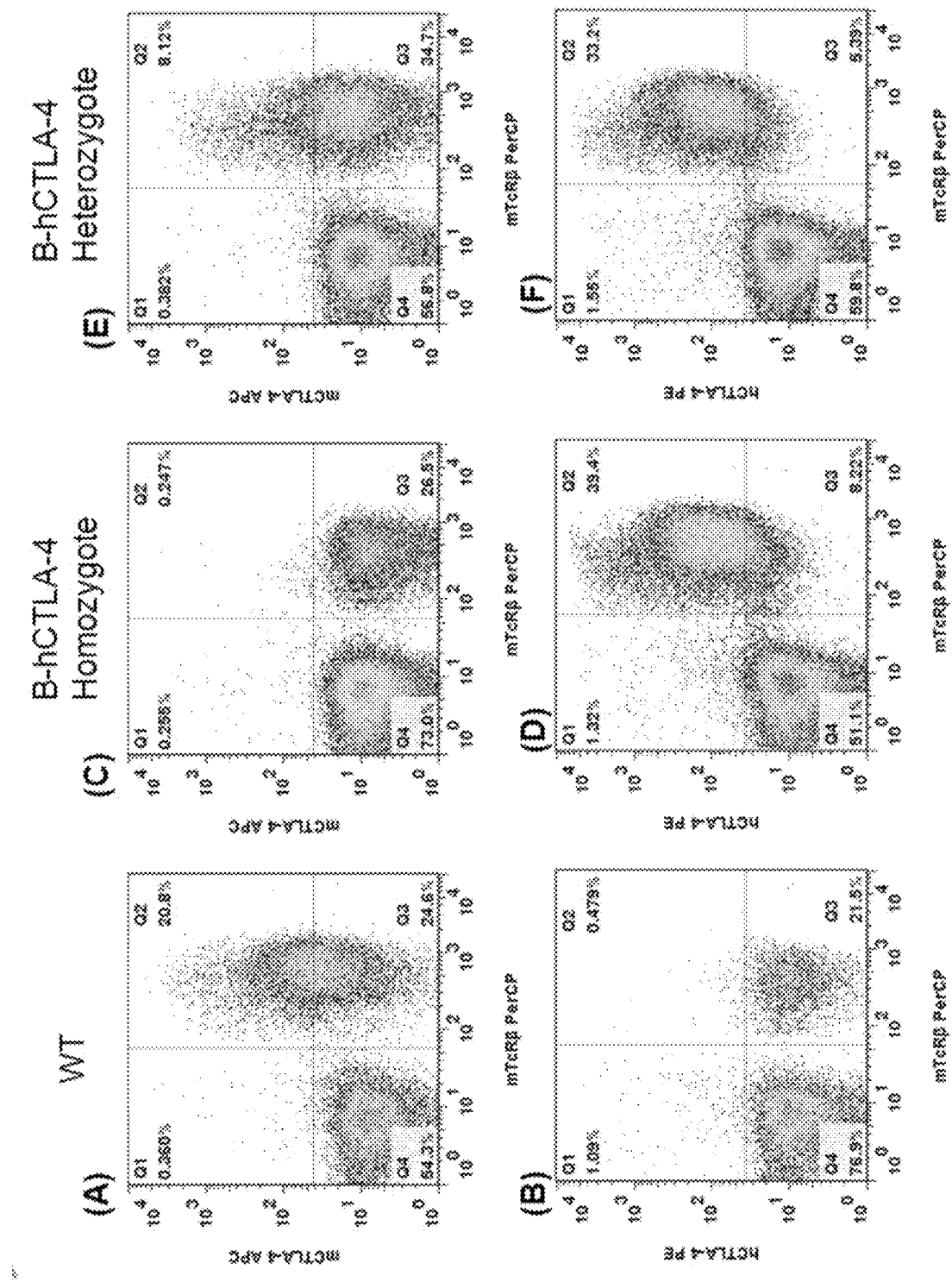
FIGS. 11A-11F show flow cytometry analysis results for a wild type C57BL/6 mouse, a B-hCTLA-4 homozygous mouse, and a B-hCTLA-4 heterozygous mouse, which were respectively stimulated by anti-mouse CD3 antibody to stimulate T cell activation in their spleens, and then anti-mouse Ctla-4 antibody mCtla-4 APC (FIGS. 11A, 11C, 11E) and anti-human CTLA-4 antibody hCTLA-4PE (FIGS. 11B, 11D, 11F) were used for cell labeling, which were then detected in the flow cytometry analysis. Compared with the control group (FIGS. 11A, 11B), the cells with the expression of human CTLA-4 protein can be detected in the spleens of B-hCTLA-4 homozygous mouse and B-hCTLA-4 heterozygous mouse (FIGS. 11D, 11F); whereas in the spleen of C57BL/6 mouse, no cells expressing human CTLA-4 protein were detected.

FACS detection: The T cells extracellular proteins were simultaneously stained with mouse Ctla-4 antibody mCtla-4 APC and mouse T cell surface antibody mTcRβ, as well as human CTLA-4 antibody hCTLA-4PE and mouse T cell surface antibody mTcRβ; the cells were then washed with PBS and then detected for protein expression by FACS detection. Flow cytometry analysis results are shown in FIG. 11, when compared with the C57BL/6 mice with or without the stimulation of CD3 antibody for T cell activation in spleen, the mouse Ctla-4 antibody is able to detect the cells expressing mouse CTLA-4 protein in the spleen samples from B-hCTLA-4 heterozygote and the C57BL/6 control mice (FIGS. 11A and 11E); while the mouse Ctla-4 antibody is unable to detect the cells expressing mouse CTLA-4 protein in the spleen samples from B-hCTLA-4 homozygote (FIG. 11C). Moreover, the human CTLA-4 antibody is able to detect the cells expressing human CTLA-4 protein in the spleen samples from B-hCTLA-4 heterozygote and homozygote (FIGS. 11D and 11F); while the human Ctla-4 antibody is unable to detect the cells expressing human CTLA-4 protein in the spleen samples from the C57BL/6 control mice (FIG. 11B).

RT-PCR detection: total RNA was extracted from the spleen cells of wild-type C57BL/6 mice and B-hCTLA-4 homozygotes and heterozygotes, and cDNA were then obtained by reverse transcription using a reverse transcription kit.

Primers for mCTLA-4 RT-PCR:
F1:
(SEQ ID NO: 59)
5'-ACCCCTTGAGGTTAGCCCT-3',
and

R1:
(SEQ ID NO: 60)
5'-TTGTAGAACAGCTATACGACCCA-3'
were used to amplify mouse Ctla-4 fragment of 122 bp.

Primers for hCTLA-4 RT-PCR:
F1:
(SEQ ID NO: 61)
5'-ATACTGTGCTAACAGGCCTCA-3',
and R1:
(SEQ ID NO: 62)
5'-ACCCATTGTCATTAGGAAGCACT-3'
were used to amplify human CTLA-4 fragment of 152 bp.

PCR reaction system was 20 µL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 12A:
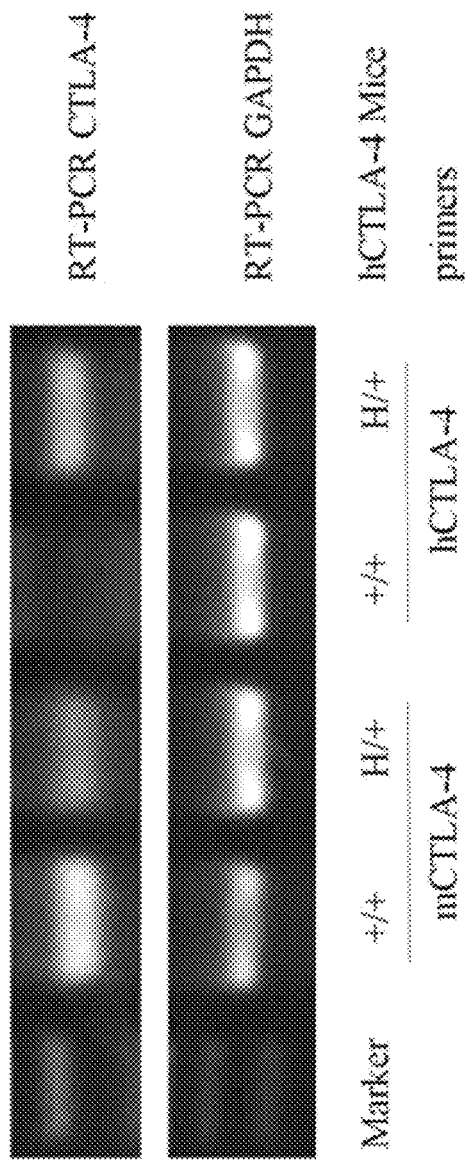
FIGS. 12A and 12B show RT-PCR detection results, wherein +/+ is wild type C57BL/6 mouse; H/+ is B-hCTLA-4 heterozygous mouse; H/H is B-hCTLA-4 homozygous mouse; and GAPDH is an internal control.
Figure 12B:
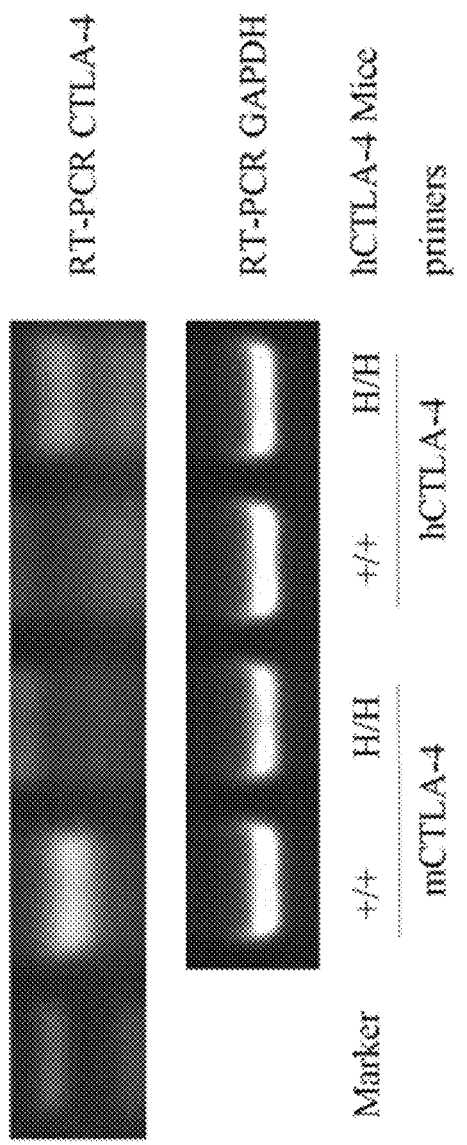

The results are shown in FIG. 12. The mRNA expression of mouse Ctla-4 could be detected in the activated cells of wild-type C57BL/6 mice and B-hCTLA-4 heterozygous mice (FIG. 12A); while the mRNA expression of human CTLA-4 could be detected in the activated cells of B-hCTLA-4 homozygous and heterozygous mice (FIG. 12B).

Example 6. Identification of Gene Knockout Mice

Since the cleavage of Cas9 results in DNA double strands break, and the homologous recombination repair may result in insertion/deletion mutations, it is possible to obtain CTLA-4 gene-disrupted gene knockout mouse while preparing the CTLA-4 gene humanized mouse. A pair of primers was thus designed. They are located on the left side of the 5' end target site, and to the right side of the 3' end target site, which are shown as follows:

(SEQ ID NO: 63)
5'-GCATCAAGCTTGGTACCGATACAGCTGAAAGATGGGAAGTGGAGT-3';

(SEQ ID NO: 64)
5'-ACTTAATCGTGGAGGATGATCACATCCCCAAATGCGTTTCATTGC-3'

Figure 13:
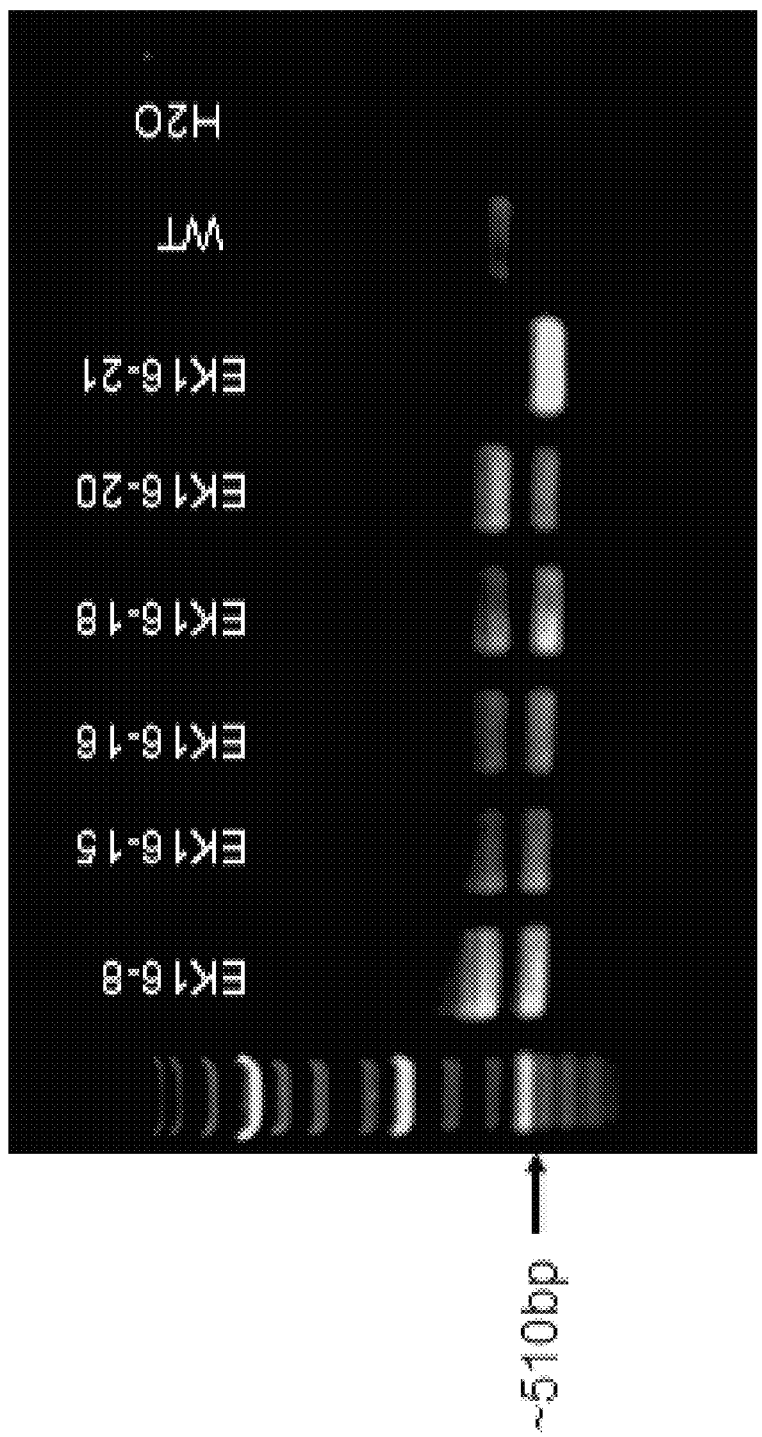
FIG. 13 shows PCR identification results for gene knockout mice, wherein WT is wild type, the mice with no. EK16-8, EK16-15, EK16-16, EK16-18 and EK16-20 are heterozygous mice, while EK16-21 may be a homozygous mouse.

The wild-type mice should have only one PCR band, and the product length should be 790 bp; the heterozygous mice should have another PCR band, and the product length should be about 510 bp; the homozygous mice should also have only one 510 bp PCR band. The PCR reaction system and conditions were identical to those of Example 5, the obtained mice were identified as knockout mice, and the PCR results are shown in FIG. 13.

Example 7. Pharmacological Validation of B-hCTLA-4 Gene Humanized Animal Model

Yervoy (ipilimumab) is an anti-CTLA-4 complete human monoclonal antibody that is able to block the interaction of CTLA-4 with its ligand (CD80/CD85). It was developed by Bristol-Myers Squibb, and was approved by FDA in 2011 for the treatment of advanced melanoma. It is the first approved anti-human CTLA-4 antibody. Thus, in this example, the in vivo efficacy validation study on the humanized animal model was carried out using Yervoy (ipilimumab), a commercially available drug that has been widely confirmed for its function on regulating the human CTLA-4 signaling pathway.

The specific method was as follows: B-hCTLA-4 homozygous mice (6-8 weeks) were subcutaneously injected with mouse colon cancer cell MC38 ($5\times10^5$/100 μl PBS), and when the tumor volume grew to about 100 mm$^3$, the mice were divided to a control group and a treatment group based on tumor size (n=5/group). The treatment group was randomly selected from different doses of Yervoy (1 to 10 mg/kg) injection treatment; the control group was injected with an equal volume of blank solvent. The frequency of administration was once every 3 days. A total of 6 times of administrations were provided. The tumor volume was measured twice a week and the body weight of the mice was weighed as well. Moreover, euthanasia was performed when the tumor volume of a single mouse reached 3000 mm$^3$.

Figure 14:
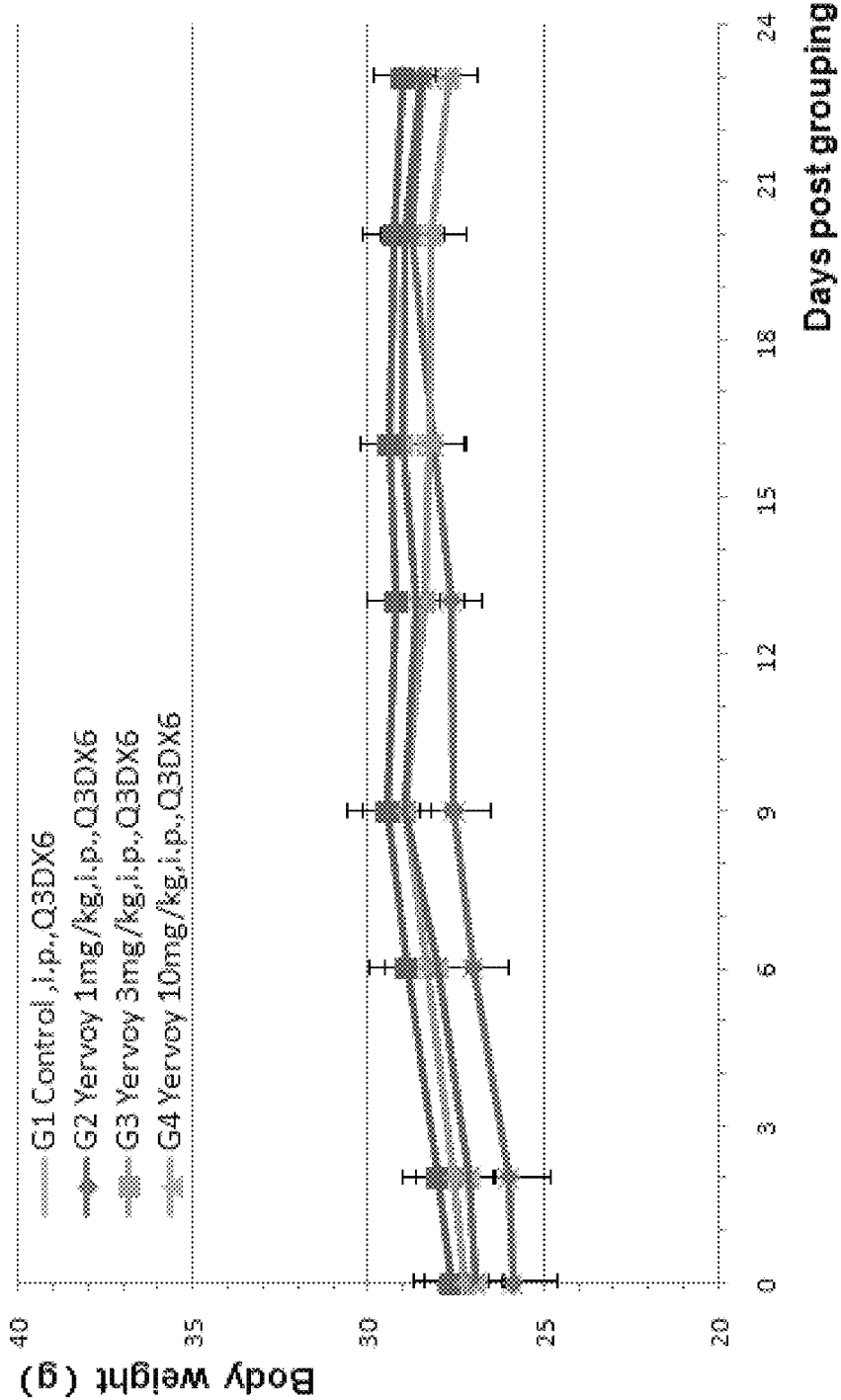
FIG. 14. Mouse colon cancer cells MC38 were implanted into B-hCTLA-4 mice and antitumor efficacy studies were performed using different doses of human CTLA-4 antibody Yervoy (1 mg/kg, 3 mg/kg and 10 mg/kg). There was no significant difference in mean weight gain between experimental groups G1 to G4.
Figure 15:
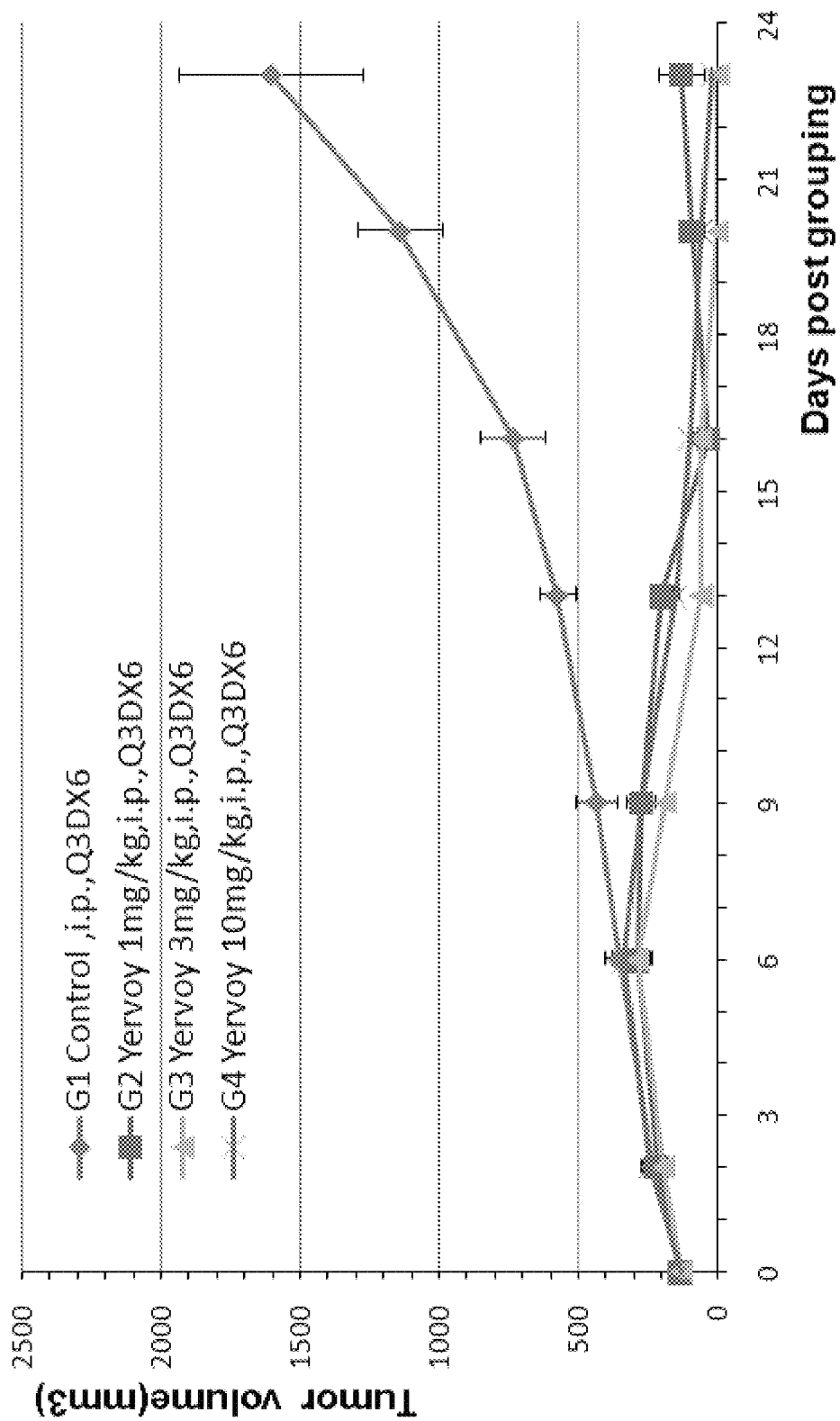
FIG. 15. Mouse colon cancer cells MC38 were implanted into B-hCTLA-4 mice and antitumor efficacy studies were performed using different doses of human CTLA-4 antibody Yervoy (1 mg/kg, 3 mg/kg and 10 mg/kg). The average volume of tumor in the experimental group was significantly smaller than that in G1 control group, and the differences were significant.

Overall, the animals in each group were healthy, and the body weights of all the treatment and control mice were not significantly changed throughout the experimental period (FIG. 14). The tumor in the control group continued growing during the experimental period; when compared with the control group mice, the tumor volumes in the treatment group were smaller by a certain degree and/or disappeared (FIG. 15). It thus can be determined that the use of different doses of Yervoy for human CTLA-4 signaling pathway is able to significantly inhibit the tumor growth in mice.

Table 7 shows the tumor volumes at day 16 days after the grouping, the tumor volumes at the end of the experiment, the survival of the mice, the condition of tumor free mice, the tumor (volume) inhibition rate ($TGI_{TV}$), and the statistical differences (P value) in mouse body weights and tumor volume between the treatment and control groups.

At the end of the experiment (on the 23rd day after the grouping), the body weight of each group increased and there was no significant difference between the groups (p>0.05), indicating that the animals were well tolerated with Yervoy. Concerning tumor volume, in the control group (G1), the average tumor volume was 1608±741 mm$^3$. Nine mice in the treatment group had their tumors disappeared (60%) at the end of the experiment. The specific results were as follows: at the doses of 1 mg/kg (G2), 3 mg/kg (G3) and 10 mg/kg (G4), the average tumor volumes were 133±180 mm$^3$, 0±0 mm$^3$ and 23±20 mm$^3$, respectively. The tumor volumes of all the treated mice were significantly smaller than those in the control group, and the differences between the treatment group and the control group were statistically significant (p<0.5).

Overall, the best treatment effects were reached after 3 weeks of administration. Moreover, after the administration was terminated, the low dose treatment group showed significant tumor growth, and the $TGI_{TV}$ values were 99.8%, 109.1% and 97.4%, respectively.

The results show that different doses of anti-human CTLA-4 antibody Yervoy have a significant inhibitory effect and/or elimination effect (TGItv>60%) on the tumors in B-hCTLA-4 mice. In addition, various doses show different effects in vivo. This demonstrates that the B-hCTLA-4 mouse model can be used to assess the effectiveness of drugs targeting human CTLA-4 in vivo and to assess the therapeutic effect as well.

TABLE 7

| | | Tumor volume (mm$^3$) | | | | Tumor-free | $TGI_{TV}$ % | P value | |
|---|---|---|---|---|---|---|---|---|---|
| | | Day 0 | Day 16 | Day 23 | Survival | | | Body weight | Tumor volume |
| Control group | G1 | 131 ± 37 | 738 ± 265 | 1608 ± 741 | 100% | 0/5 | N/A | N/A | N/A |
| Treatment group | G2 | 130 ± 31 | 33 ± 10 | 133 ± 180 | 100% | 1/5 | 99.8 | 0.639 | 0.003 |
| | G3 | 135 ± 37 | 62 ± 20 | 0 ± 0 | 100% | 5/5 | 109.1 | 0.531 | 0.001 |
| | G4 | 134 ± 42 | 97 ± 90 | 23 ± 22 | 100% | 5/5 | 97.4 | 0.953 | 0.001 |

The above example has demonstrated that the B-hCTLA-4 mouse model responds to a widely validated inhibitor of human CTLA-4 and exhibits a dose-dependent correlation of tumor growth inhibition. The following examples used multiple anti-human CTLA-4 antibodies to further validate the B-hCTLA-4 mouse as an in vivo animal model for screening, evaluation and study of human CTLA-4 signaling pathway regulators.

Example 8. Use of b-hctla-4 Gene Humanized Animal Model for Screening Anti-Human ctla-4 Regulator Experiment 1: $5\times10^5$ mice colon cancer cell MC38 were injected subcutaneously on right body side of B-hCTLA-4 homozygous mice (4-8 weeks old). When the tumor volume reached about 100 mm$^3$, the mice were randomly divided into control group and treatment group (n=5/group). The treatment group mice were randomly selected to receive the positive control Yervoy or one of the three types of anti-human CTLA-4 antibodies in a dose of 3 mg/kg. The control group was injected with blank solvent. Dosage: intraperitoneal injection, once every 3 days, a total of 6 times of administration. The tumor volume was measured twice a week and euthanasia was performed when the tumor volume of a single mouse reached 3000 mm$^3$ after cancer cell injection.

Table 8 lists the main data and analysis results for each experiment, including the tumor volume at the time of grouping and at 20 days after the grouping, the tumor volume at the end of the experiment (28 days after the grouping), the survival of the mice, the Tumor Growth Inhibition value ($TGI_{TV}$) and the difference between the body weight and the tumor volume of the treatment group and the control group (P value).

TABLE 8

| | | Tumor volume (mm$^3$) | | | | | P value | |
|---|---|---|---|---|---|---|---|---|
| | | Day 0 | Day 20 | Day 28 | Survival | Tumor-free | TGI$_{TV}$% | Body weight | Tumor volume |
| Control group | G1 | 131 ± 37 | 1142 ± 341 | 2914 ± 1429 | 5/5 | 0/5 | N/A | N/A | N/A |
| Treatment group | G2 (Yervoy) | 135 ± 37 | 5 ± 8 | 6 ± 13 | 5/5 | 4/5 | 104.6 | 0.416 | 0.002 |
| | G3 (Ab-A) | 134 ± 33 | 47 ± 41 | 3 ± 7 | 5/5 | 4/5 | 104.7 | 0.100 | 0.002 |
| | G4 (Ab-B) | 135 ± 33 | 586 ± 487 | 1767 ± 2302 | 5/5 | 0/5 | 41.4 | 0.324 | 0.371 |
| | G5 (Ab-C) | 133 ± 37 | 771 ± 634 | 1800 ± 1527 | 5/5 | 0/5 | 40.1 | 0.595 | 0.268 |

Figure 16:
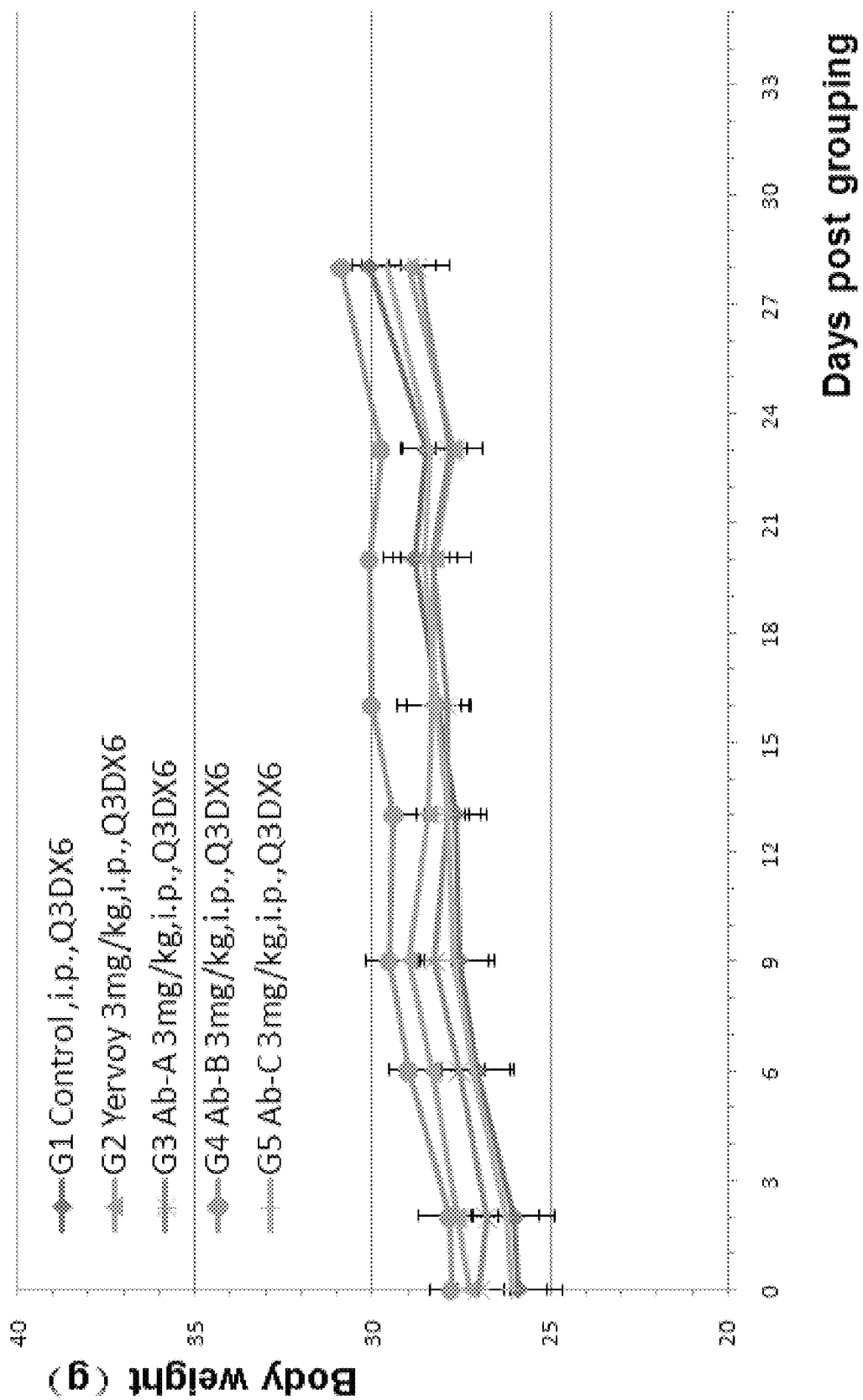
FIG. 16. Mouse colon cancer cells MC38 were implanted into B-hCTLA-4 mice. The anti-tumor efficacy test was performed using the positive control drugs Yervoy or one of the three anti-human CTLA-4 antibodies Ab-A, Ab-B and Ab-C. There was no significant difference in the average body weight the experimental animals in groups G1 to G5.
Figure 17:
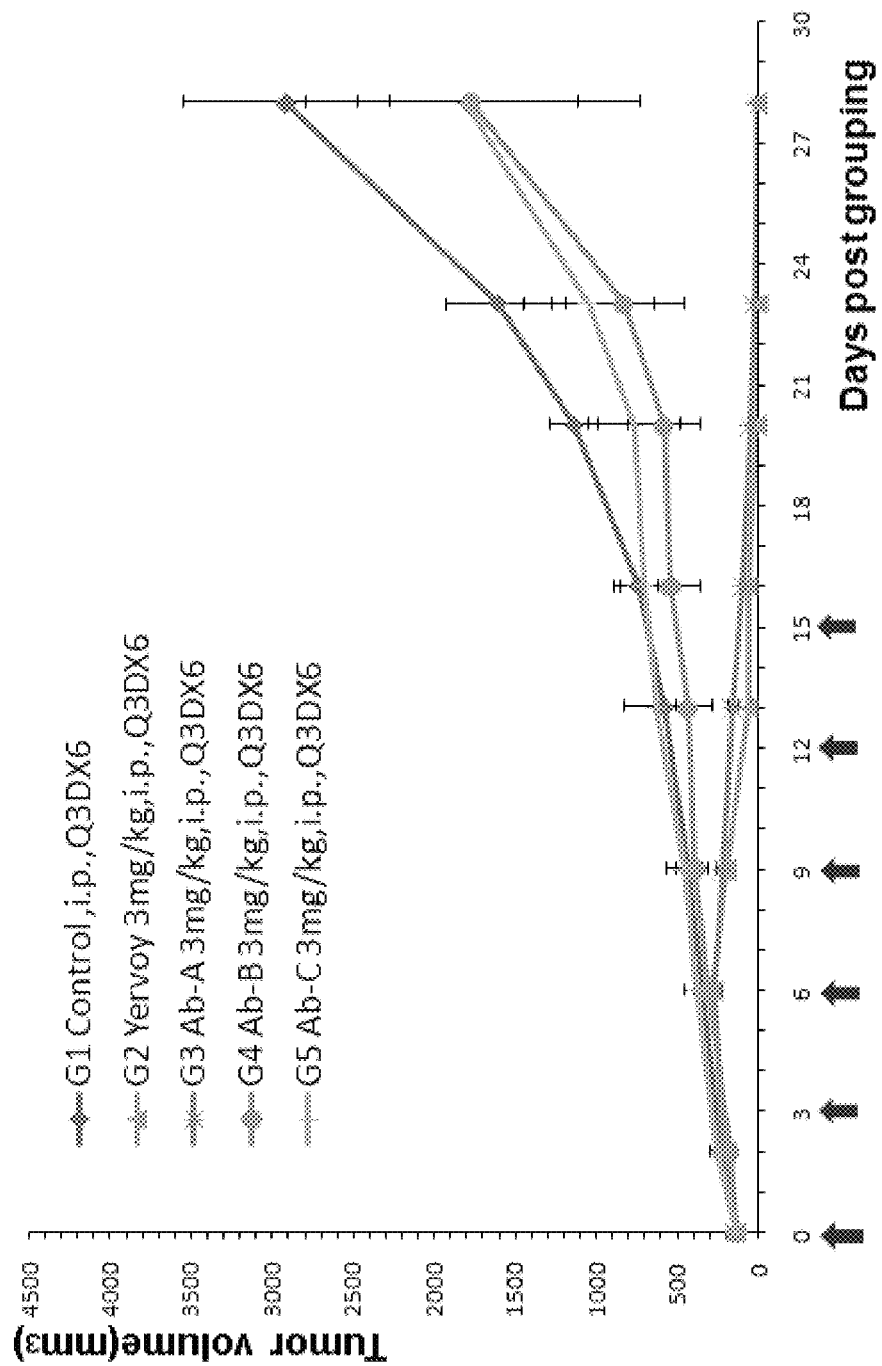
FIG. 17. Mouse colon cancer cells MC38 were implanted into B-hCTLA-4 mice. The anti-tumor efficacy test was performed using the positive control drugs Yervoy or one of the three anti-human CTLA-4 antibodies Ab-A, Ab-B and Ab-C. There was no significant difference in tumor volume between the treatment group with the Ab-A antibody (G3) and the treatment group with Yervoy (G2), and there were significant differences between the G2, G3 groups and the control group (G1) ($P<0.05$). In addition, the tumor volumes of mice treated with Ab-B and Ab-C antibodies (G4, G5) were significantly larger than that of Yervoy treatment group (G2) and Ab-A antibody treatment group (G3), indicating that under the condition of the same dose and frequency, anti-human Ab-A antibody and the positive reference Yervoy have similar treatment efficacy; they have equivalent effects on the inhibition of tumor growth, while the effects of anti-human CTLA-4 antibody Ab-B and Ab-C are not as good as that of Yervoy or Ab-A antibody.

Overall, during the experiment, the animals were in good health condition. At the end of the experiment, the weight gains of the animals in each group were good. There was no significant difference in body weight between the treatment group mice and the control group mice (P>0.05), indicating that the animals had good tolerance to positive control Yervoy and the three anti-human CTLA-4 antibodies. There was no significant difference in the body weight of all experimental and control mice (FIG. 16) throughout the entire experimental period. However, concerning the tumor volume (FIG. 17), the tumors of all of the control mice were growing continuously during the experimental period. When compared with the control group mice, the tumor volumes in the treatment group were smaller by a certain degree and/or disappeared, indicating that the four anti-human CTLA-4 antibodies have various anti-tumor effects. In addition, they do not produce significant toxic effects on the animals, thus are safe.

At the end of the experiment, the average tumor volume was 2914±1429 mm$^3$ in the control group (G1), 6±13 mm$^3$ in the Yervoy treatment group, 3±7 mm$^3$ in the Ab-A antibody treatment group (G3), 1767±2302 mm$^3$ in the Ab-B antibody treatment group (G5), and 1800±1527 mm$^3$ in the Ab-C antibody treatment group (G5). In addition, the tumor volumes of the mice treated with Ab-A antibody (G3) and with Yervoy (G2) were not significantly different; the tumor volumes of the G2, G3 groups were significantly different when compared with that of the control group (G1), (P<0.05), the TGI$_{TV}$ were 104.6%, 104.7%. At the end of the experiment (on the 28th day after the grouping), 4 mice of the 5 mice in each group had their tumors disappeared (80%). On the other hand, the tumor volumes of the mice in the groups treated with Ab-B or Ab-C antibody (G4, G5) were significantly larger than those in the Yervoy treatment group (G2) and the Ab-A antibody treatment group (G3). No tumor free mice were present in the groups treated with Ab-B or Ab-C antibody at the end of the experiment. The results show that under the condition of same dose and administration frequency, the anti-human CTLA-4 antibody Ab-A was similar in treatment effect to the positive control Yervoy; they have similar inhibitory effects on tumor growth. The effect of anti-human CTLA-4 antibodies Ab-B and Ab-C are not as good as those of Yervoy and the antibody Ab-A. This experiment has showed that the B-hCTLA-4 mice can be used in screening anti-human CTLA-4 drugs (for example, antibodies) and in vivo efficacy tests.

Experiment 2: 5×10$^5$ mice colon cancer cell were injected subcutaneously on right body side with MC38 B-hCTLA-4 homozygous mice (4-8 weeks old). When the tumor volume has reached about 100 mm$^3$, the mice were randomly divided into control group and treatment group (n=5/group). The treatment group mice received the treatment of various doses of anti-human CTLA-4 antibody Ab-A (0.3 to 3 mg/kg). The control group was injected with blank solvent. Dosage: intraperitoneal injection, once every 3 days, a total of 6 times of administration. The tumor volume was measured twice a week and euthanasia was performed when the tumor volume of a single mouse reached 3000 mm$^3$ after cancer cell injection.

Table 9 lists the main data and analysis results for each experiment, including the tumor volume at the time of grouping and at 15 days after the grouping, the tumor volume at the end of the experiment (22 days after the grouping), the survival of the mice, the Tumor Growth Inhibition value (TGI$_{TV}$) and the difference between the body weight and the tumor volume of the treatment group and the control group (P value).

TABLE 9

| | | Tumor volume (mm$^3$) | | | | | P value | |
|---|---|---|---|---|---|---|---|---|
| | | Day 0 | Day 15 | Day 22 | Survuval | Tumor free | TGI$_{TV}$% | Body weight | Tumor volume |
| Control group | G1 | 131 ± 22 | 933 ± 371 | 2879 ± 1141 | 5/5 | 0/5 | N/A | N/A | N/A |
| Treatment group | G2 (3 mg/kg) | 131 ± 27 | 119 ± 86 | 49 ± 66 | 5/5 | 2/5 | 103.0 | 0.452 | 0.001 |
| | G3 (1 mg/kg) | 131 ± 25 | 289 ± 425 | 601 ± 1178 | 5/5 | 1/5 | 82.9 | 0.679 | 0.015 |
| | G4 (0.3 mg/kg) | 130 ± 27 | 493 ± 348 | 983 ± 885 | 5/5 | 0/5 | 69.0 | 0.931 | 0.019 |

Figure 18:
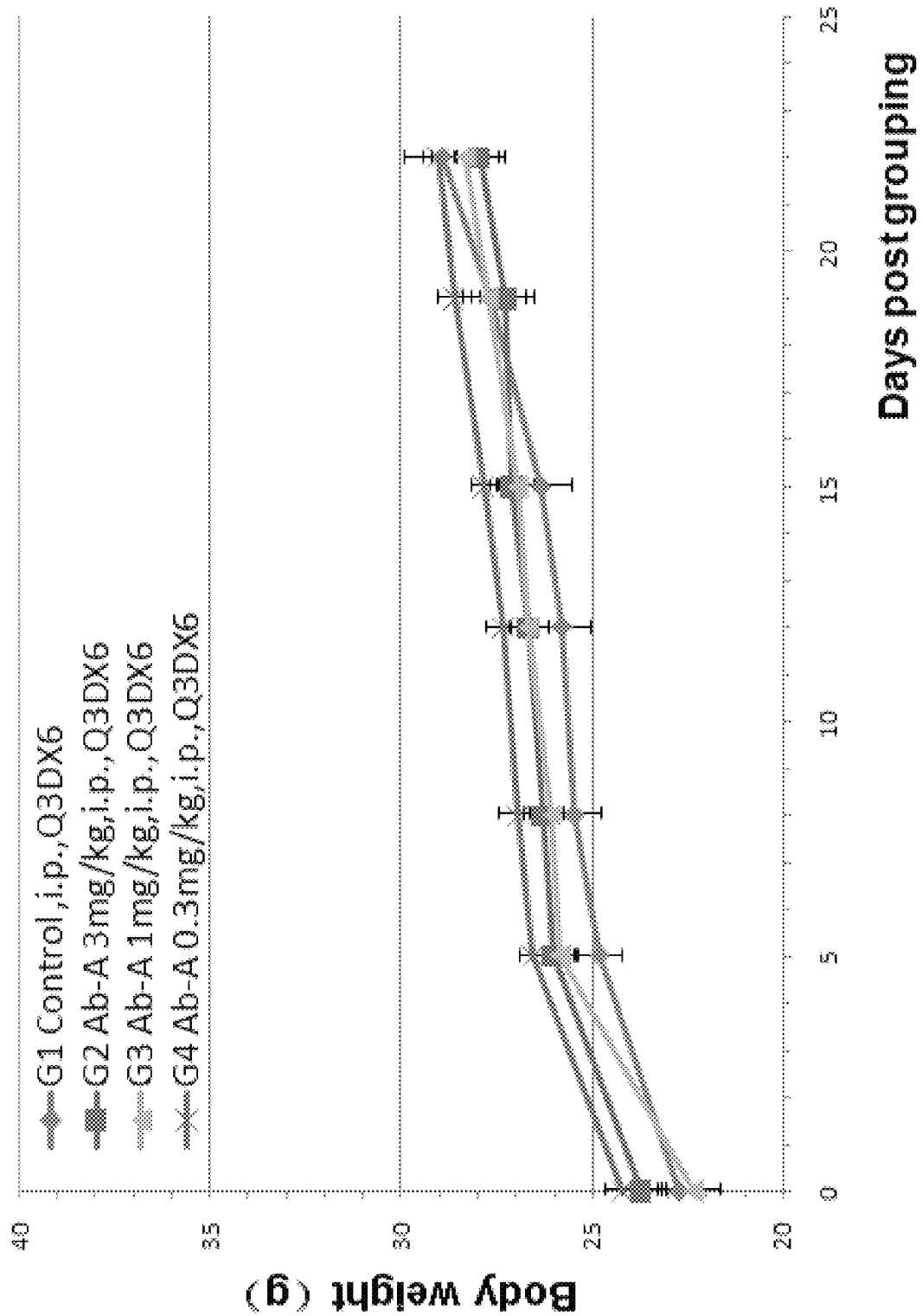
FIG. 18. Mouse colon cancer cells MC38 were implanted into B-hCTLA-4 mice and antitumor efficacy studies were performed using different doses of anti-human CTLA-4 antibody Ab-A (3 mg/kg, 1 mg/kg and 0.3 mg/kg). There was no significant difference in mean weight gain between experimental groups G1 to G4.
Figure 19:
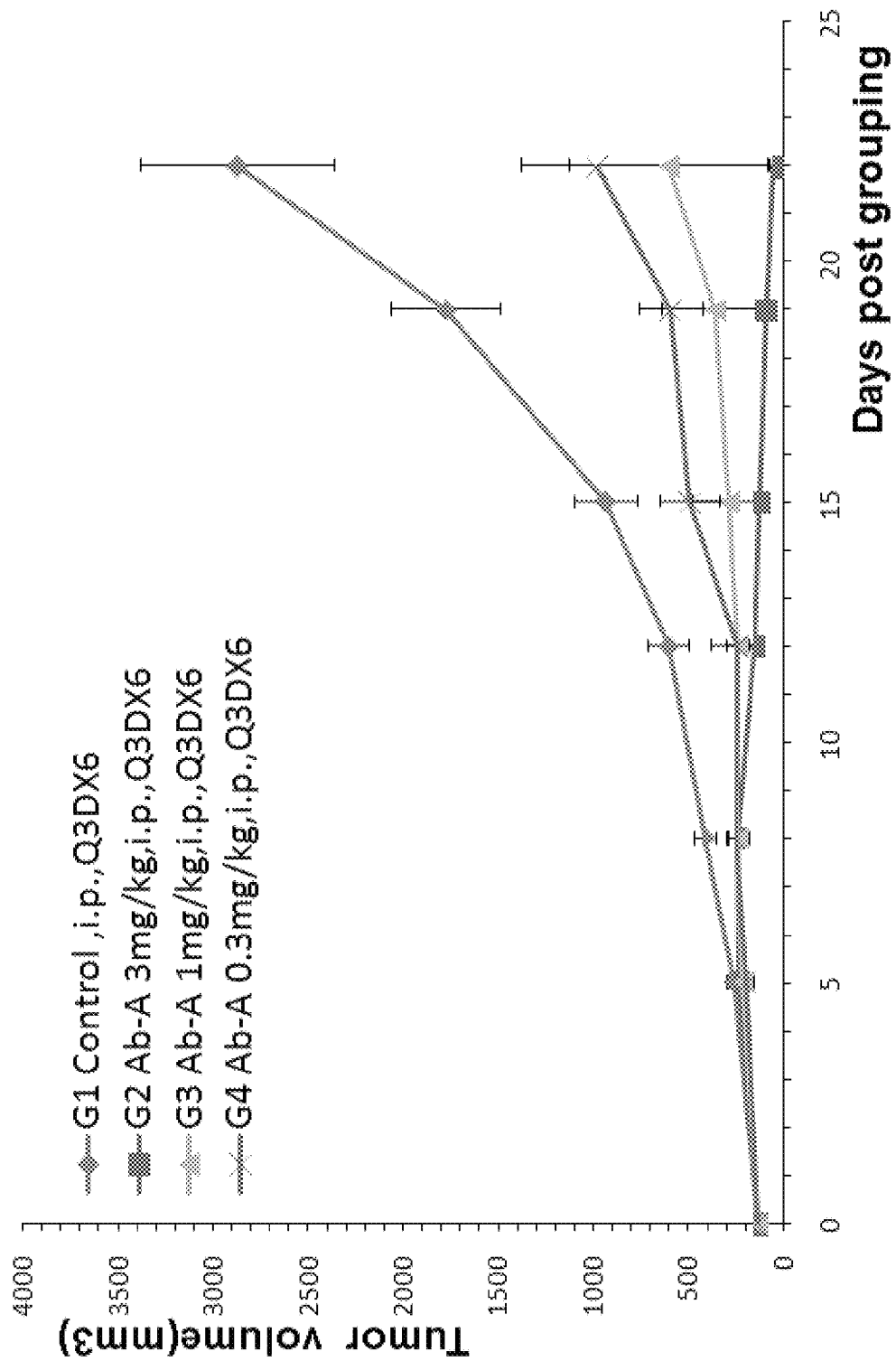
FIG. 19. Mouse colon cancer cells MC38 were implanted into B-hCTLA-4 mice and antitumor efficacy studies were performed using different doses of anti-human CTLA-4 antibody Ab-A (3 mg/kg, 1 mg/kg and 0.3 mg/kg). The average volume of the tumor in the G2 to G4 groups was significantly smaller than those in the G1 control group, and there was significant difference and dose-correlation.

During the experiment the animals were in good health condition. At the end of the experiment, the weight gains of the animals in each group were good. There was no significant difference in body weight between the treatment group mice and the control group mice (P>0.05), confirming that the animals had good tolerance to the anti-human CTLA-4 antibody Ab-A. There was no significant difference in the body weight of all experimental and control mice (FIG. 18) throughout the entire experimental period. However, concerning the tumor volume (FIG. 19), the tumors of all of the control mice were growing continuously during the experimental period. In the three treatment groups, among the 15 mice, the tumors of 3 mice disappeared at the end of the experiment. Overall the best treatment effect has been reached after 3 weeks of treatment. In addition, after the treatment is terminated for each group, the low dose treatment group showed significant tumor growth. At the end of the experiment, the average tumor volume in the control group was 2879±1141 mm³, the average tumor volumes at the dose level of 3 mg/kg (G2), 1 mg/kg (G3), and 0.3 mg/kg (kg) were 49±66 mm³, 601±1178 mm³, and 983±885 mm³, respectively. Moreover, the tumor volumes of all the treated mice were significantly smaller than that of the control group, and the $TGI_{TV}$ were 103.0%, 82.9% and 69.0% respectively, which indicated that various doses of Ab-A antibody had significant inhibitory effect on the tumor ($TGI_{TV}$>60%). The higher the dose of treatment, the better the effect of treatment, indicating different doses of anti-human CTLA-4 antibody Ab-A in B-hCTLA-4 mice showed different efficacies, and also indicating the tumor growth inhibition is dose related.

Example 9. Preparation and Identification of Double Humanized or Multiple Humanized Mice Mice containing the human CTLA-4 gene (such as the B-hCTLA-4 animal model prepared using the methods as described in the present disclosure) can also be used to prepare a double-humanized or multi-humanized animal model. For example, in Example 4, the fertilized egg cells used in the microinjection and embryo transfer process can be selected from the fertilized egg cells of other genetically modified mice or the fertilized egg cells of B-hCTLA-4 mice, so as to obtain CTLA-4 humanized and other gene modified double or multiple gene modified mouse models.

In addition, the B-hCTLA-4 animal model homozygote or heterozygote can be mated with other genetically modified homozygous or heterozygous animal models, and the progeny is then screened; according to the Mendelian law, there is a chance to obtain the CTLA-4 humanized and other gene modified double genes or multiple genes modified heterozygous animal models, and then the obtained heterozygous can be mated with each other to finally obtain the double genes or multiple genes modified homozygote.

In the case of the generating double humanized CTLA-4/PD-1 mouse, since the mouse Ctla-4 gene and Pd-1 gene are located on the same chromosome, when carrying out the microinjection as shown in Example 4, the fertilized egg cells of B-hPD-1 mouse were used to replace the fertilized egg cells of wild-type mouse for gene editing. The double humanized CTLA-4/PD-1 mouse was obtained by screening the progeny mice.

Figure 20:
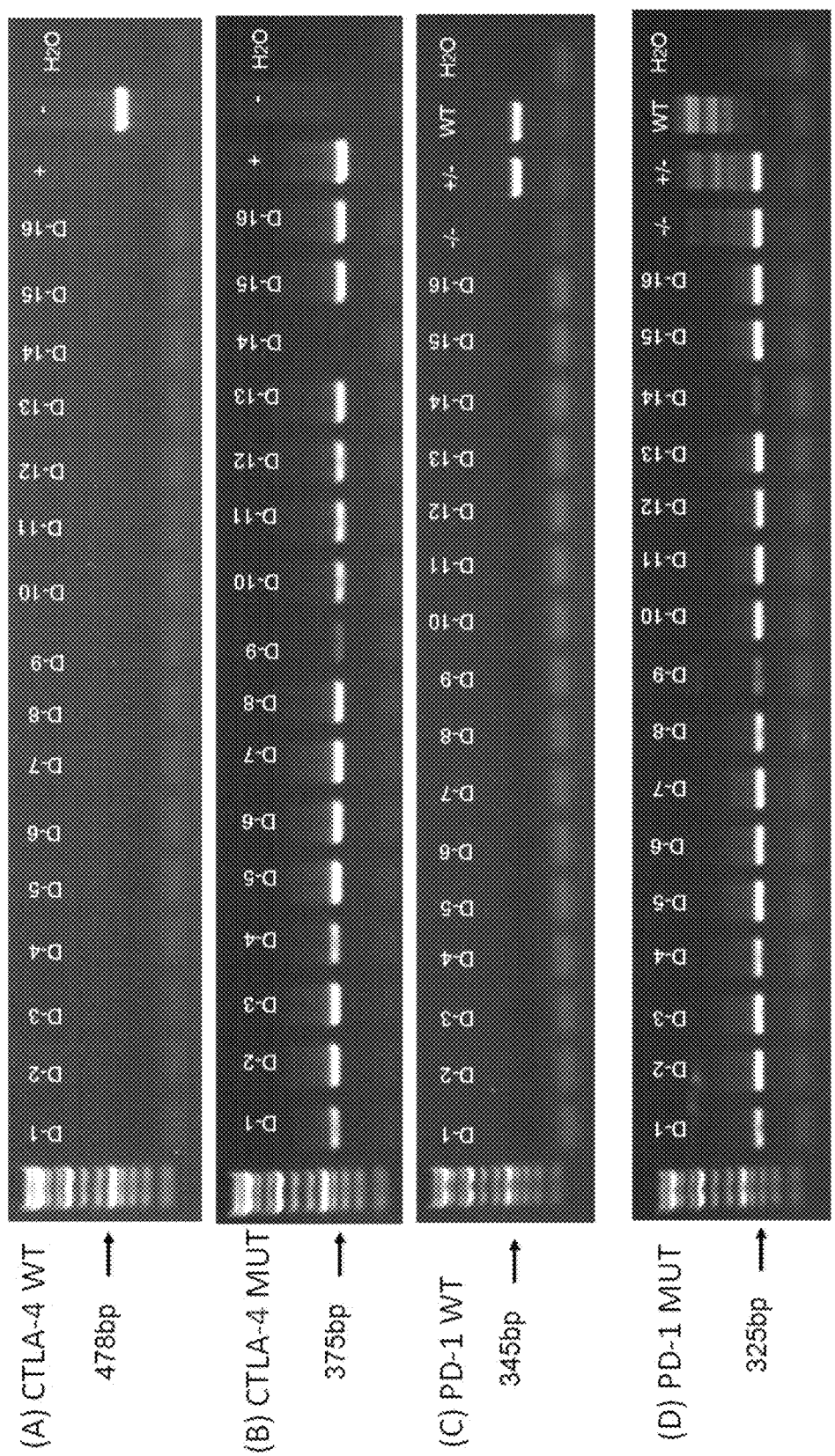
FIG. 20. Mouse tail PCR identification result, where + is positive control, − is negative control (FIGS. 20A, 20B); WT is wild type, −/− is PD-1 gene humanized homozygous mouse, +/− is PD-1 gene humanized heterozygous mouse (FIGS. 20C, 20D).

PCR analysis was performed on the mouse tail genomic DNA of double humanized CTLA-4/PD-1 mice using four pairs of primers. The specific sequences and product lengths are shown in Table 10. The reaction system and reaction conditions are shown in Tables 9 and 10. The results for a number of humanized CTLA-4/PD-1 mice are shown in FIG. 20, wherein FIGS. 20A and 20B show that the mice numbered D-1 to D-13 and D-15 to D-16 are CTLA 4 homozygous mice, FIGS. 20C and 20D show that the mice numbered D-1 to D-16 are PD-1 homozygous mice. The results of the two groups indicate that the 15 mice of D-1 to D-13, and D-15 to D-16 were double gene homozygotes.

TABLE 10

Primer sequences

| Primer | Sequence | Product length |
|---|---|---|
| CTLA-4 WT | F: 5'-ccatcacacaacactgatgaggtcc-3' (SEQ ID NO: 65) R: 5'-cacatccccaaatgcgtttcattgc-3' (SEQ ID NO: 66) | WT: 478 bp |
| CTLA-4 MUT | F: 5'-acagctgaaagatgggaagtggagt-3' (SEQ ID NO: 67) R: 5'-tcaactcattccccatcatgtaggttgc-3' (SEQ ID NO: 52) | Mut: 375 bp |
| PD-1 MUT | F: 5'-cttccacatgagcgtggtcagggcc-3' (SEQ ID NO: 68) R: 5'-ccaagggactattttagatgggcag-3' (SEQ ID NO: 69) | Mut: 325 bp |
| PD-1 WT | F: 5'-gaagctacaagctcctaggtaggggg-3' (SEQ ID NO: 70) R: 5'-acgggttggctcaaaccattaca-3' (SEQ ID NO: 71) | WT: 345 bp |

TABLE 11

PCT reaction system (20 μL) system is shown below:

| | |
|---|---|
| 2x Master Mix | 10 μL |
| Upstream primer (10 μM) | 0.5 μL |
| Downstream primer (10 μM) | 0.5 μL |
| Mouse tail genomic DNA | 200 ng |
| KOD-Plus-(1 U/μL) | 0.6 μL |
| ddH₂O | Add to 20 μL |

TABLE 12

PCR amplification reaction condition is shown below:

| Temperature | Time | Cycles |
|---|---|---|
| 95° | 5 min | 1 |
| 95° | 30 sec | 30 |
| 59° | 30 sec | |
| 72° | 30 sec | |
| 72° | 10 min | 1 |
| 4° | 10 min | 1 |

Figures 21A, 21B, 21C, 21D, 21E, 21F:
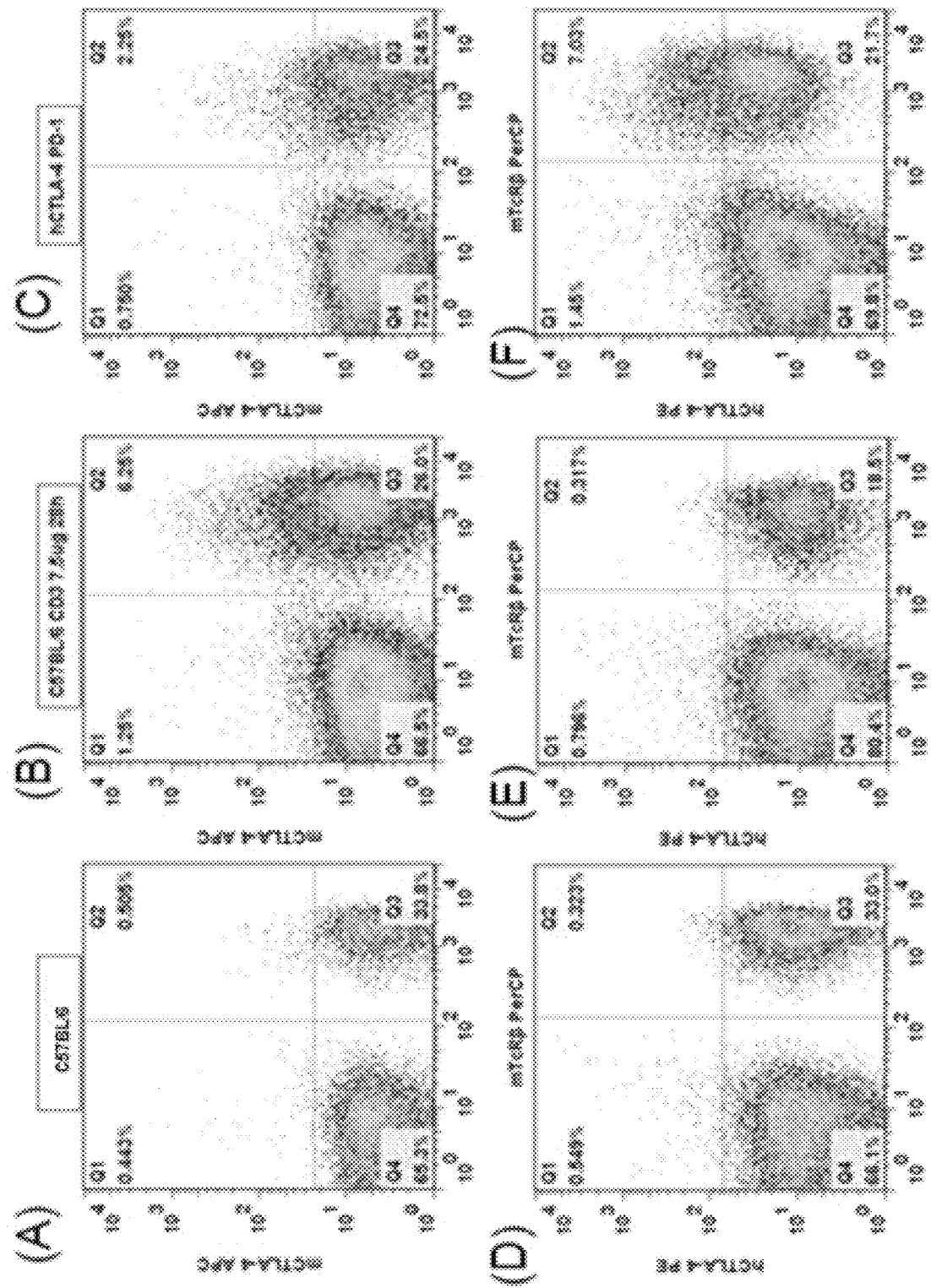
FIGS. 21A-21L show flow cytometry analysis results, wherein C57BL/6 mice and humanized CTLA-4/PD-1 heterozygous mice were used. Anti-mouse CD3 antibody was used to stimulate T cell activation in the spleens of the mice, and then the mouse CTLA-4 antibody mCTLA-4 APC (FIGS. 21A, 21B, 21C), human CTLA-4 antibody hCTLA-4 PE (FIGS. 21D, 21E, 21F), mouse PD-1 antibody mPD-1 PE (FIGS. 21G, 21H, 21I), or human PD-1 antibody hPD-1 FITC hPD-1 FITC (FIGS. 21J, 21K, 21L), and mouse T cell surface antibody mTcRβ were used to label T cell proteins. The result show that the cells expressing human CTLA-4 and PD-1 proteins were detected in the spleens of hybrid mice of heterozygous double humanized CTLA-4/PD-1, while no cells expressing human CTLA-4 or PD-1 protein were detected in the spleen of C57BL/6 control mice.
Figures 21G, 21H, 21I, 21J, 21K, 21L:
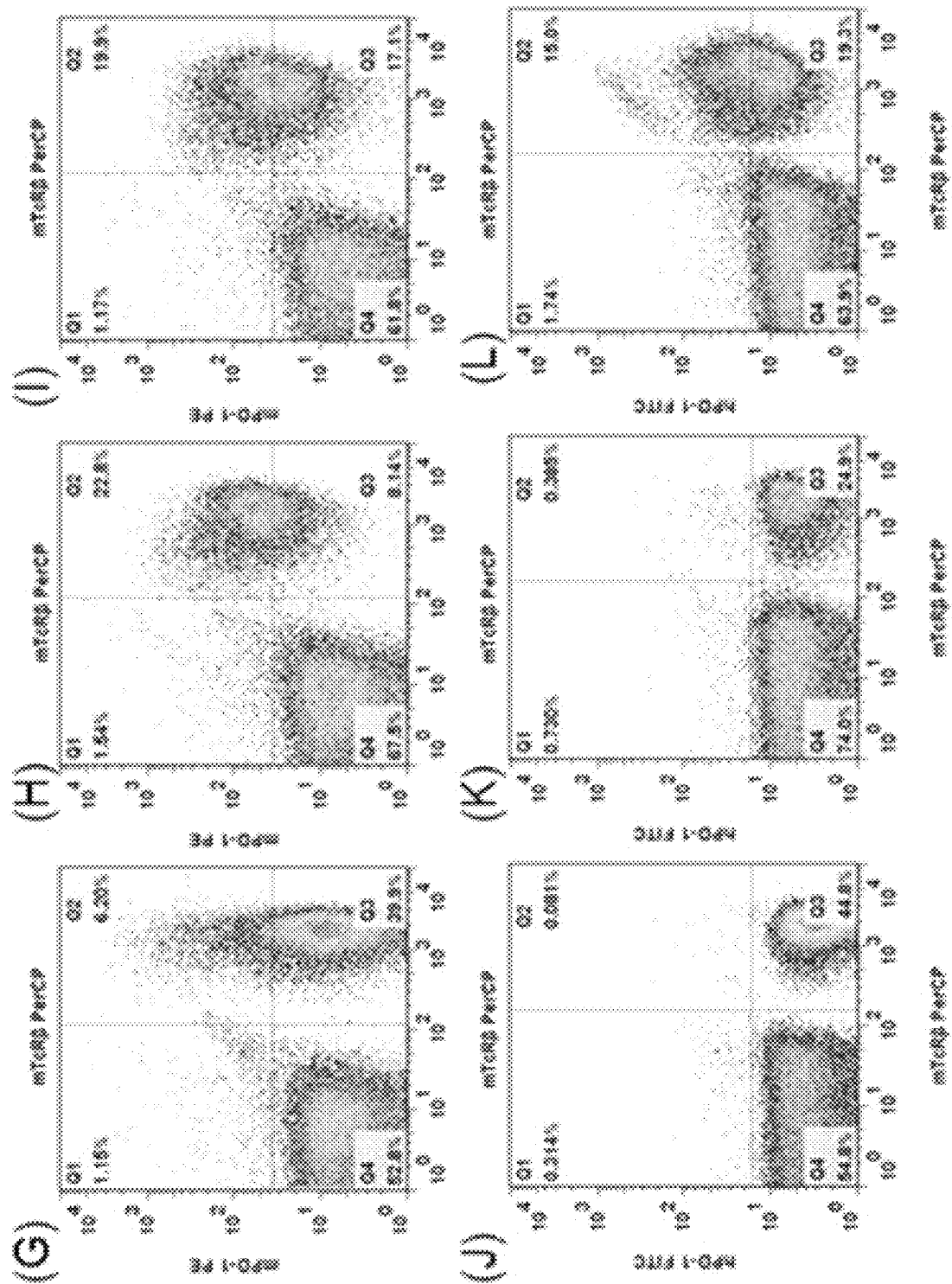

The expression of the double humanized CTLA-4/PD-1 mice was further examined. A double humanized CTLA-4/PD-1 heterozygote (6 weeks old) was selected for the study. Two wild type C57BL/6 mice were selected as control. Mice were injected with 7.5 μg of mouse CD3 antibody intraperitoneally. After 28 days, the mice were euthanized, and then the spleens of the mice were collected. The spleen samples were ground and the ground samples were filtered through a 70 μm cell mesh. The filtered cell suspensions were centrifuged and the supernatants were discarded; erythrocyte lysis solution was added for lysis for 5 min, and then PBS solution was added to neutralize the lysis reaction. The solution was centrifuged again and the supernatants were discarded, the cells were washed once with PBS. The obtained spleen cell samples were next stained for T cell extracellular protein with the mouse CTLA-4 antibody mCTLA-4APC (FIGS. 21A, 21B, 21C), or human CTLA-4 antibody hCTLA-4 PE (FIGS. 21D, 21E, 21F), or murine PD-1 antibody mPD-1 PE (FIGS. 21G, 21H, 21I), or human PD-1 antibody hPD-1 FITC (FIGS. 21J, 21K, 21L), and the mouse T cell surface antibody mTcRβ. The cells were subsequently washed with PBS. The protein expressions in the cells were detected by flow cytometry. The results of flow cytometry detection were shown in FIGS. 21A-21L. Flow cytometry analysis results show when compared with the C57BL/6 mice with or without the stimulation of CD3 antibody for T cell activation in spleen, the human CTLA-4 antibody and human PD-1 antibody can detect the cells expressing human CTLA-4 and PD-1 proteins in the spleen of humanized CTLA-4/PD-1 heterozygous mice; whereas in the spleen of the control C57BL/6 mice, no cells expressing human CTLA-4 or PD-1 protein were detected in the control mice.

Example 10. Pharmacological Validation of Animal Models with Double or Multiple Humanized Genes Experiments were performed on hCTLA-4/hPD-1 mice to illustrate how to use animal models with double or multiple humanized or partially humanized genes to determine drug efficacy. Keytruda (pembrolizumab) and Yervoy (ipilimumab) were used in this example. Keytruda (pembrolizumab) is a humanized anti-PD-1 antibody and Yervoy (ipilimumab) is an anti-CTLA-4 complete human monoclonal antibody.

CTLA-4/PD-1 homozygous mice (6-8 weeks) were subcutaneously injected with mouse colon cancer cell MC38 ($5\times10^5$/100 μl PBS), and when the tumor volume grew to about 100 mm$^3$, the mice were divided to a control group and a treatment group based on tumor size (n=5/group). The treatment group was randomly selected to receive one or both of pembrolizumab and ipilimumab. The control group was treated with human IgG antibody. The dose and frequency of administration is listed in Table 13. The tumor volume was measured twice a week and the body weight of the mice was weighed as well. Euthanasia was performed when the tumor volume of a single mouse reached 3000 mm$^3$.

TABLE 13-continued

| Group | Drug | Dosage/route of administration/administration frequency |
|---|---|---|
| G4 | Yervoy + Keytruda | Yervoy: 0.3 mg/kg; intraperitoneal injection; once every 3 days (6 administrations in total) Keytruda: 0.1 mg/kg; intraperitoneal injection; once every 3 days (6 administrations in total) |

Figure 22:
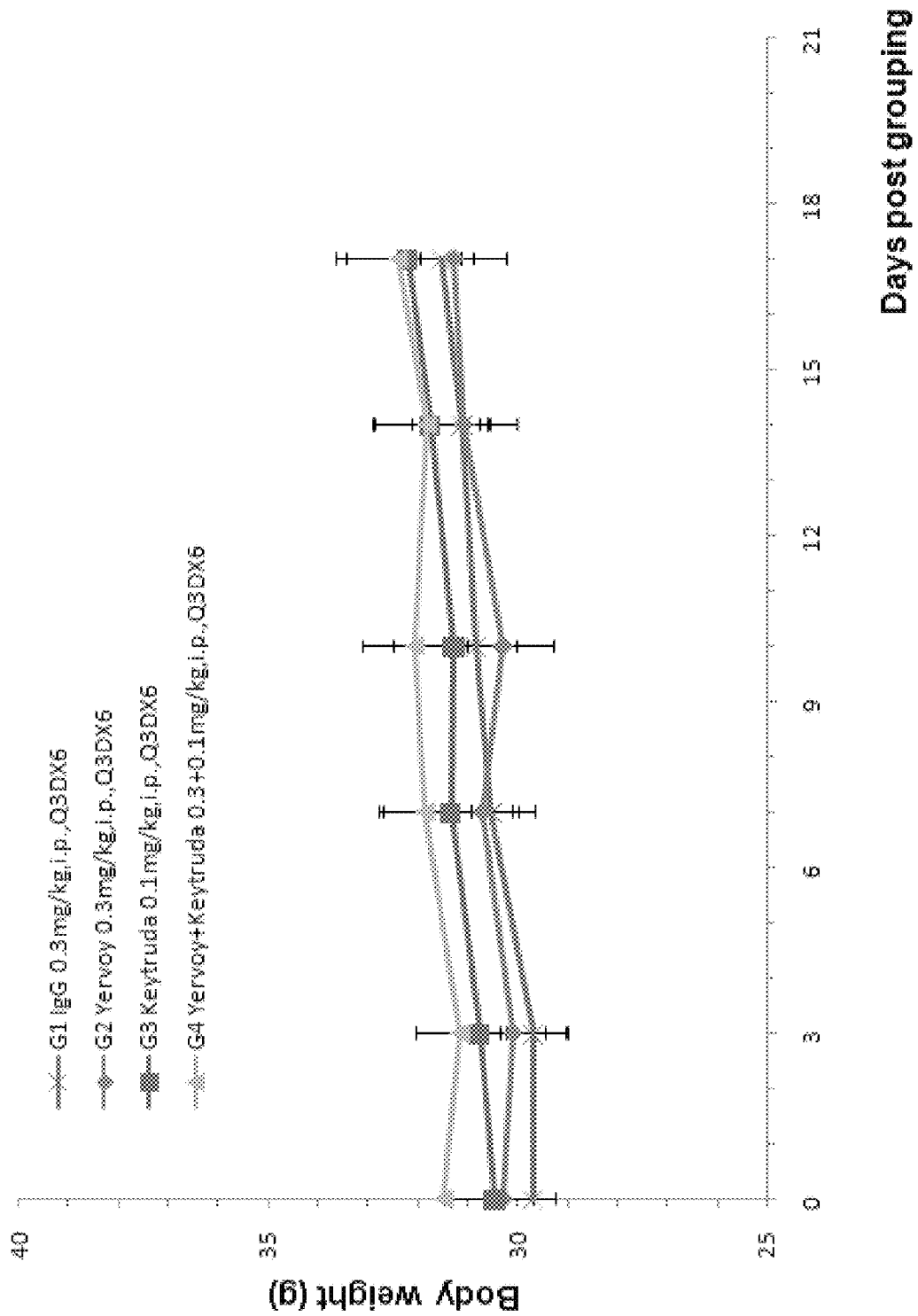
FIG. 22 shows there was no significant difference in mean weight gain between experimental groups G1 (control; IgG), G2 (Yervoy), G3 (Keytruda), G4 (Yervoy+Keytruda) in CTLA-4/PD-1 homozygous mice implanted with mouse colon cancer cells MC38.
Figure 23:
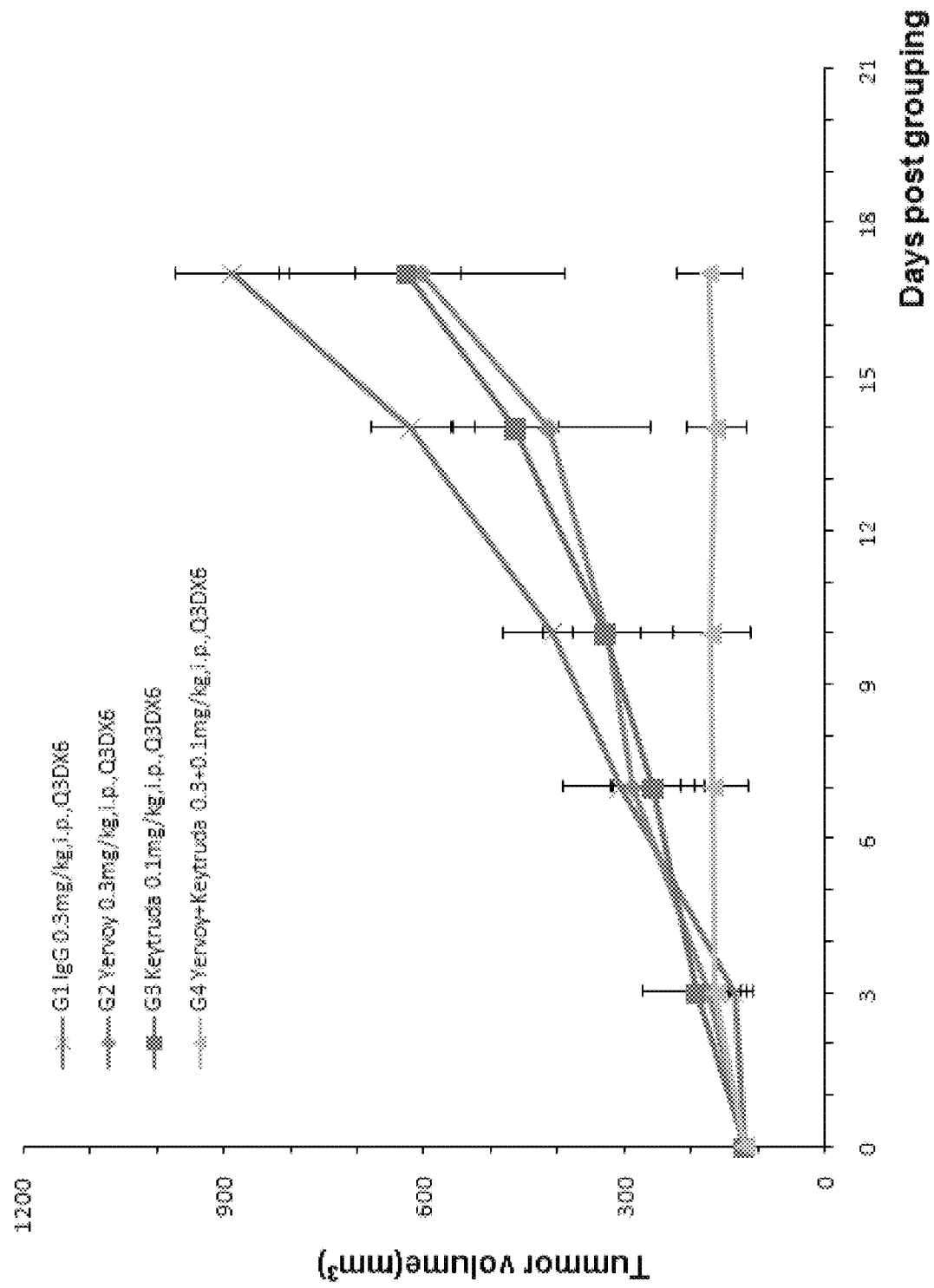
FIG. 23 shows the tumor volume in CTLA-4/PD-1 homozygous mice treated with Yervoy, Keytruda, or the combination of Yervoy and Keytruda was significantly smaller than the control group, and the tumor volume in mice treated with the combination of Yervoy and Keytruda was significantly smaller than the group treated with Yervoy alone or Keytruda alone.

Overall, the animals in each group were healthy, and the body weights of mice in the treatment group and the control group did not significantly change throughout the experimental period (FIG. 22). The tumor in the control group (G1) continued growing during the experimental period; when compared with the control group mice, the tumor volumes in the treatment group (G2-G4) were smaller by a certain degree (FIG. 23). It thus can be determined that the use of Yervoy, Keytruda, and the combination of Yervoy and Keytruda can significantly inhibit the tumor growth in mice.

Table 14 shows the tumor volumes at the day of grouping and at 10 days after the grouping, the tumor volumes at the end of the experiment (17 days after grouping), the survival of the mice, the tumor (volume) inhibition rate (TGITV), and the statistical differences (P value) in mouse body weights and tumor volume between the treatment and control groups.

At the end of the experiment (17 days after the grouping), the body weight of each group increased and there was no significant difference between the groups (p>0.05), indicating that the animals were well tolerated with Yervoy, Keytruda, or the combination of Yervoy and Keytruda. Regarding the tumor volume, in the control group (G1), the average tumor volume was 888±333 mm$^3$. In G2 (Yervoy), the average tumor volume was 605±479 mm$^3$. In G3 (Keytruda), the average tumor volume was 626±174 mm$^3$. In G4 (Yervoy and Keytruda), the average tumor volume was 175±110 mm$^3$.

The tumor volumes of all the treated mice were significantly smaller than those in the control group, and the differences between the treatment group and the control group were different. Furthermore, the tumor volume in the group (G4) receiving the combination of Yervoy and Keytruda is significantly smaller than the tumor volume in the group receiving Yervoy alone or Keytruda alone. Thus, the results show that combination treatment may have better efficacy than using Yervoy or Keytruda alone in terms of inhibiting tumor growth.

TABLE 14

| | | Tumor volume (mm3) | | | | | P value | |
|---|---|---|---|---|---|---|---|---|
| | | Day 0 | Day 10 | Day 17 | Survival | TGI$_{TV}$% | Weight | Tumor volume |
| Control | G1 | 121 ± 17 | 407 ± 137 | 888 ± 333 | 100% | N/A | N/A | N/A |
| Treatment | G2 | 121 ± 12 | 327 ± 217 | 605 ± 479 | 100% | 36.8 | 0.844 | 0.310 |
| | G3 | 120 ± 27 | 329 ± 112 | 626 ± 174 | 100% | 34.1 | 0.687 | 0.157 |
| | G4 | 120 ± 24 | 171 ± 128 | 175 ± 110 | 100% | 92.8 | 0.547 | 0.002 |

TABLE 13

| Group | Drug | Dosage/route of administration/administration frequency |
|---|---|---|
| G1 (Control) | Human IgG | 0.3 mg/kg; intraperitoneal injection; once every 3 days (6 administrations in total) |
| G2 | Yervoy | 0.3 mg/kg; intraperitoneal injection; once every 3 days (6 administrations in total) |
| G3 | Keytruda | 0.1 mg/kg; intraperitoneal injection; once every 3 days (6 administrations in total) |

Example 11. Preparation Method Based on Embryonic Stem Cells

Figure 24:
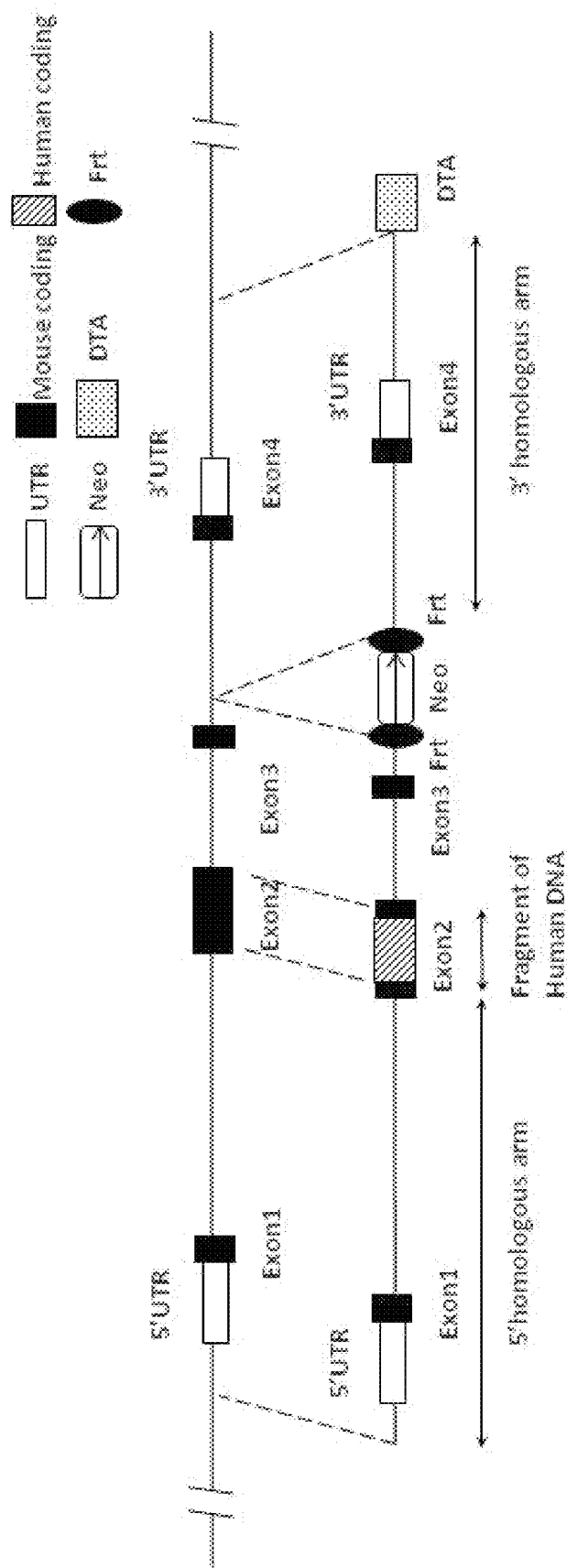
FIG. 24 is a schematic diagram of the targeting strategy for embryonic stem cells.

The non-human mammals can also be prepared through other gene editing systems and approaches, which includes, but is not limited to, gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other molecular biology techniques. In this example, the conventional ES cell gene homologous recombination technique is used as an example to describe how to obtain a CTLA-4 gene humanized mouse by other methods. According to the gene editing strategy of the methods described herein and the humanized mouse CTLA-4 gene map (FIG. 4), a targeting strategy has been developed as shown in FIG. 24. FIG. 24 shows the design of the recombinant vector. In view of the fact that one of the objects is to replace the exon 2 of the mouse Ctla-4 gene in whole or in part with the human CTLA-4 gene fragment, a recombinant vector that contains a 5' homologous arm (4291 bp), a 3' homologous arm (3979 bp) and a humanized gene fragment (312 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wild type mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the CTLA-4 gene humanized homozygous mice can be obtained by mating these mice with each other. The methods of genotyping and phenotypic detection of the obtained F1 heterozygous mice or F2 homozygous mice are similar to those used in Example 5 described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of evaluating an anti-cytotoxic T-lymphocyte associated protein 4 (CTLA-4) antibody for the treatment of cancer, the method comprising:
   a) administering an anti-CTLA-4 antibody to a genetically modified mouse that has a tumor, and
   b) determining whether the antibody inhibits the tumor, wherein the genetically modified mouse has a genome comprising a nucleic acid sequence encoding a chimeric CTLA-4 comprising an amino acid sequence that is at least 95% identical to the, amino acid sequence of SEQ ID NO: 41, wherein the nucleic acid sequence: i) comprises exons 1, 3, 4, of a mouse CTLA-4 gene and a humanized exon 2 of the CTLA-4 gene, and ii) is operably linked to an endogenous promoter of the mouse CTLA-4 gene, and wherein the mouse functionally expresses the chimeric CTLA-4.

2. The method of claim 1, wherein the chimeric CTLA-4 comprises the amino acid sequence of SEQ ID NO: 41.

3. The method of claim 1, wherein the mouse does not express endogenous CTLA-4.

4. The method of claim 1, wherein the mouse is homozygous with respect to the nucleic acid sequence encoding the chimeric CTLA-4.

5. The method of claim 1, wherein the mouse further comprises a nucleic acid sequence encoding an additional human or humanized protein.

6. The method of claim 5, wherein the additional human or humanized protein is programmed cell death protein 1

(PD-1), TNF Receptor Superfamily Member 4 (OX40), Lymphocyte Activating 3 (LAG-3), Programmed Cell Death 1 Ligand 1 (PD-L1), CD47, or T-cell Immunoreceptor With Ig and ITIM Domains (TIGIT).

7. The method of claim 1, wherein the tumor comprises human cancer cells.

8. The method of claim 1, wherein the anti-CTLA-4 antibody is an anti-human CTLA-4 antibody.

9. A method of evaluating an anti-cytotoxic T-lymphocyte associated protein 4 (CTLA-4) antibody for the treatment of cancer, the method comprising:
 a) administering an anti-CTLA-4 antibody to a genetically modified mouse that has a tumor, and
 b) determining whether the antibody inhibits the tumor, wherein the genetically modified mouse has a genome comprising exon 1, exon 3, and exon 4 of an endogenous CTLA-4 gene and a modification of endogenous exon 2 comprising a replacement of 50-330 nucleotides of endogenous exon 2 with 50-330 nucleotides from exon 2 of a human CTLA-4 gene, wherein the mouse functionally expresses a chimeric CTLA-4 protein.

10. The method of claim 9, wherein the tumor comprises human cancer cells.

11. The method of claim 9, wherein the anti-CTLA-4 antibody is an anti-human CTLA-4 antibody.

12. The method of claim 9, wherein the mouse further comprises a nucleic acid sequence encoding an additional human or humanized protein.

13. The method of claim 12, wherein the additional human or humanized protein is programmed cell death protein 1 (PD-1), TNF Receptor Superfamily Member 4 (OX40), Lymphocyte Activating 3 (LAG-3), Programmed Cell Death 1 Ligand 1 (PD-L1), CD47 or T-cell Immunoreceptor With Ig and ITIM Domains (TIGIT).

* * * * *

UNITED STATES PATENT AND TRADEMARK OFFICE
CERTIFICATE OF CORRECTION

PATENT NO. : 11,096,383 B2
APPLICATION NO. : 16/329275
DATED : August 24, 2021
INVENTOR(S) : Shen et al.

Page 1 of 1

It is certified that error appears in the above-identified patent and that said Letters Patent is hereby corrected as shown below:

In the Claims

Column 81, Line 64 Claim 1, delete "the," and insert -- the --, therefor.

Column 84, Line 15 Claim 13, delete "CD47" and insert -- CD47, --, therefor.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*